US009259000B2

(12) United States Patent
Shimada et al.

(10) Patent No.: US 9,259,000 B2
(45) Date of Patent: Feb. 16, 2016

(54) AUXIN BIOSYNTHESIS INHIBITOR

(75) Inventors: Yukihisa Shimada, Kanagawa (JP); Ko Kikuzato, Kanagawa (JP); Megumi Narukawa, Kanagawa (JP); Tadao Asami, Saitama (JP); Kazuo Soeno, Kagawa (JP)

(73) Assignees: Riken, Saitama (JP); Public University Corporation Yokohama City University, Yokohama-shi (JP)

( * ) Notice: Subject to any disclaimer, the term of this patent is extended or adjusted under 35 U.S.C. 154(b) by 151 days.

(21) Appl. No.: 13/261,726

(22) PCT Filed: Feb. 28, 2012

(86) PCT No.: PCT/JP2012/055498

§ 371 (c)(1), (2), (4) Date: Aug. 27, 2013

(87) PCT Pub. No.: WO2012/118216

PCT Pub. Date: Sep. 7, 2012

(65) Prior Publication Data

US 2014/0031230 A1 Jan. 30, 2014

(30) Foreign Application Priority Data

Feb. 28, 2011 (JP) ................................ 2011-043277

(51) Int. Cl.
*A01N 43/60* (2006.01)
*A01N 43/42* (2006.01)
(Continued)

(52) U.S. Cl.
CPC ................ *A01N 43/60* (2013.01); *A01N 37/10* (2013.01); *A01N 37/28* (2013.01); *A01N 37/36* (2013.01); *A01N 37/38* (2013.01); *A01N 37/44* (2013.01); *A01N 43/20* (2013.01); *A01N 43/38* (2013.01); *A01N 43/42* (2013.01); *C07C 239/20* (2013.01);
(Continued)

(58) Field of Classification Search
None
See application file for complete search history.

(56) References Cited

U.S. PATENT DOCUMENTS

2009/0163595 A1 6/2009 Yang et al.

FOREIGN PATENT DOCUMENTS

EP 0 008 494 A1 3/1980
EP 0008494 A1 * 3/1980 ............ A01N 33/16
(Continued)

OTHER PUBLICATIONS

RN 5060-36-6, etc., STN Registry; Nov. 24, 2008; 29 pages.
(Continued)

*Primary Examiner* — Sue Liu
*Assistant Examiner* — Erin Hirt
(74) *Attorney, Agent, or Firm* — Foley & Lardner LLP

(57) ABSTRACT

An object of the present invention is to provide an auxin biosynthesis inhibitor superior to L-AOPP. The object can be attained by a compound represented by general formula (I): wherein, $R^1$ to $R^5$ and X are the same as defined in the specification or a salt or solvate thereof.

(I)

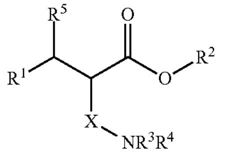

7 Claims, 43 Drawing Sheets
(20 of 43 Drawing Sheet(s) Filed in Color)

(51) Int. Cl.

| | |
|---|---|
| ***A01N 43/38*** | (2006.01) |
| ***A01N 43/20*** | (2006.01) |
| ***A01N 43/28*** | (2006.01) |
| ***A01N 37/10*** | (2006.01) |
| ***A01N 37/36*** | (2006.01) |
| ***C07C 239/20*** | (2006.01) |
| ***C07C 243/38*** | (2006.01) |
| ***C07C 251/60*** | (2006.01) |
| ***C07C 259/06*** | (2006.01) |
| ***C07C 259/10*** | (2006.01) |
| ***C07D 207/46*** | (2006.01) |
| ***C07D 209/48*** | (2006.01) |
| ***A01N 37/38*** | (2006.01) |
| ***A01N 37/28*** | (2006.01) |
| ***A01N 37/44*** | (2006.01) |

(52) U.S. Cl.

CPC ............. *C07C 243/38* (2013.01); *C07C 251/60* (2013.01); *C07C 259/06* (2013.01); *C07C 259/10* (2013.01); *C07D 207/46* (2013.01); *C07D 209/48* (2013.01)

(56) References Cited

FOREIGN PATENT DOCUMENTS

| | | | | |
|---|---|---|---|---|
| GB | 1 394 170 | | 5/1975 | |
| JP | S57-169464 | A | 10/1982 | |
| JP | 2004-300036 | A | 10/2004 | |
| JP | 2004300036 | A * | 10/2004 | ............ C07C 227/04 |
| WO | WO 2008-150031 | A1 | 11/2008 | |
| WO | WO 2010/128685 | A1 | 11/2010 | |

OTHER PUBLICATIONS

The State Intellectual Property Office of the People's Republic of China, Second Office Action on application 201280010682.3 issued Mar. 2, 2015; pp. 1-4.

Amrhein, Nikolaus, et al.; α-aminooxy-β-phenylpropionic acid—a potent inhibitor of L-phenylalanine ammonia-lyase in vitro and in vivo; pp. 313-317; Plant Science Letters, vol. 8, No. 4 (1977), Elsevier/North-Holland Scientific Publishers, Ltd.

European Patent Office supplemental search report on application 12752248.0 dated Jul. 17, 2015; 5 pages.

Geng, Xue-Li, et al.; Kinetic Resolution of Racemic Alcohols Using Thiomide Modified 1-Methyl-histidine Methyl Ester; Journal of Organic Chemistry, vol. 73, No. 21; 2008; pp. 8558-8562.

Dixon, Richard A.; An Affinity Matrix for the Isolation of L-Pheynlalanine Ammonia-Lyase; Phytochemistry, vol. 26, No. 3; 1987; pp. 659-661.

PCT International Search Report on application PCT/JP2012/055498 mailed Jun. 5, 2012; 6 pages.

* cited by examiner

Fig. 1

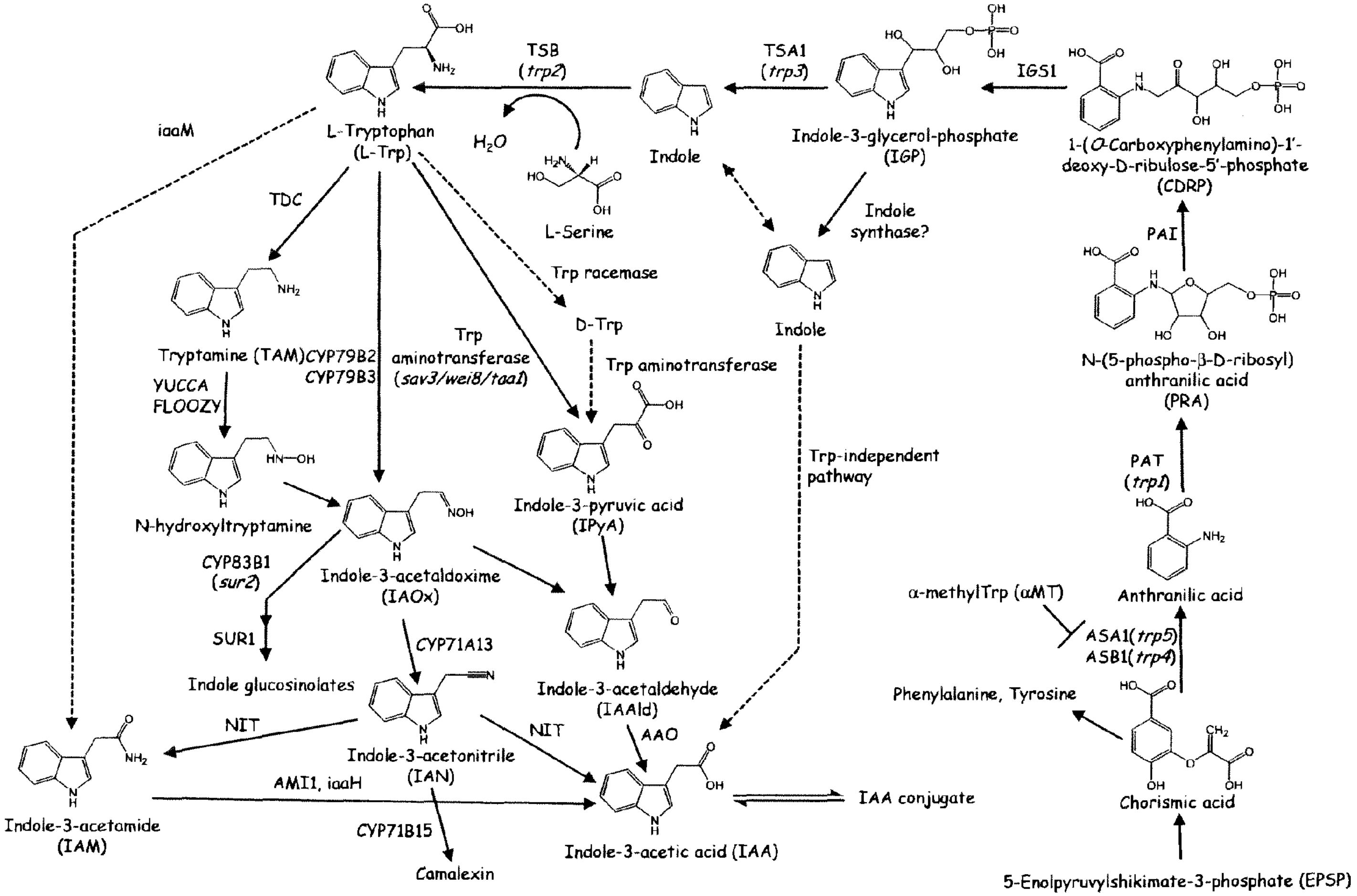

L-Tryptophan (L-Trp)
Indole
Indole-3-glycerol-phosphate (IGP)
1-(O-Carboxyphenylamino)-1'-deoxy-D-ribulose-5'-phosphate (CDRP)
L-Serine
Indole
D-Trp
Tryptamine (TAM)
N-(5-phospho-β-D-ribosyl) anthranilic acid (PRA)
N-hydroxyltryptamine
Indole-3-pyruvic acid (IPyA)
Indole-3-acetaldoxime (IAOx)
Anthranilic acid
Indole glucosinolates
Indole-3-acetaldehyde (IAAld)
Phenylalanine, Tyrosine
Indole-3-acetonitrile (IAN)
Indole-3-acetamide (IAM)
Indole-3-acetic acid (IAA)
IAA conjugate
Chorismic acid
Camalexin
5-Enolpyruvylshikimate-3-phosphate (EPSP)

KOK-1089

KOK-1090

KOK-1101

KOK-1101

KOK-1108

KOK-1114

L-AOPP

KOK-1188

KOK-1190

KOK-2022

KOK-2036

KOK-2066

KOK-2067

KOK-2110

KOK-2111

KOK-2157

KOK-2166

KOK-2168

KOK-2169

KOK-2172

KOK-2173

KOK-3034

KOK-3035

KOK-3045

KOK-3049

KOK-3050

KOK-3052

KOK-3053

KOK-2165

Fig. 4-2
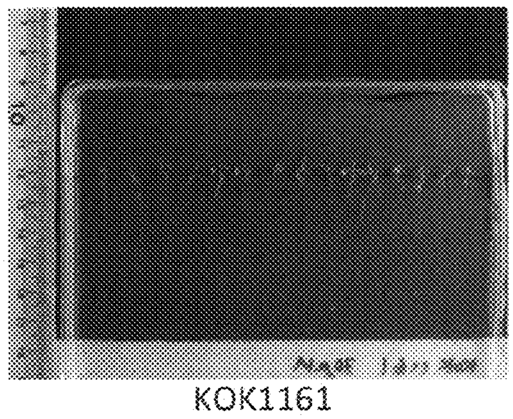
KOK1161
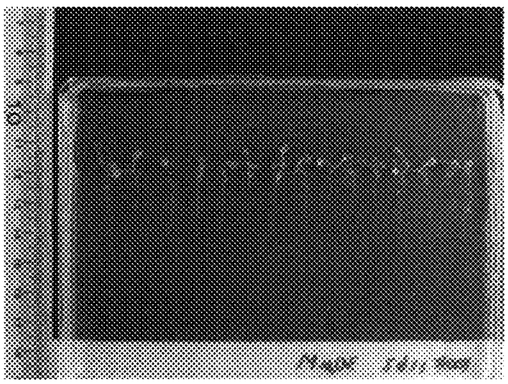
KOK1162
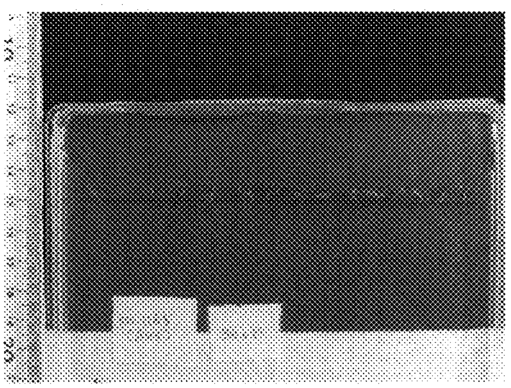
KOK1165
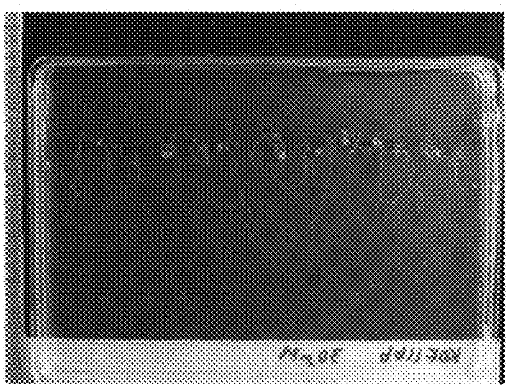
KOK1166
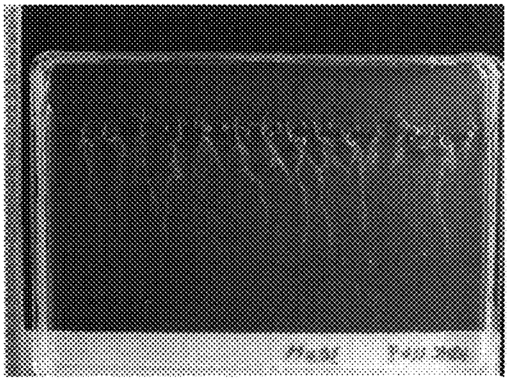
KOK1167
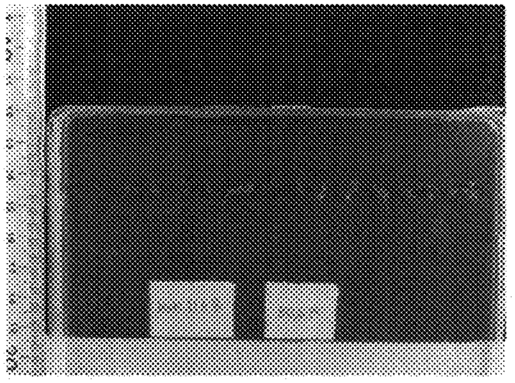
KOK1168

Fig. 4-3
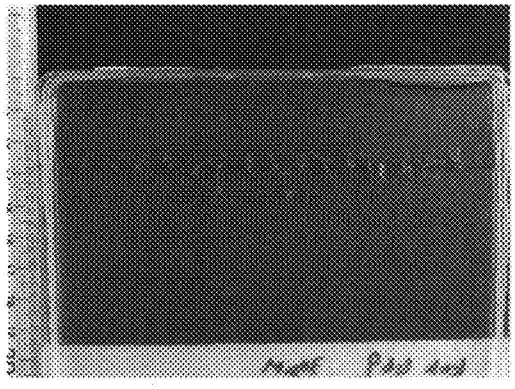
KOK1169
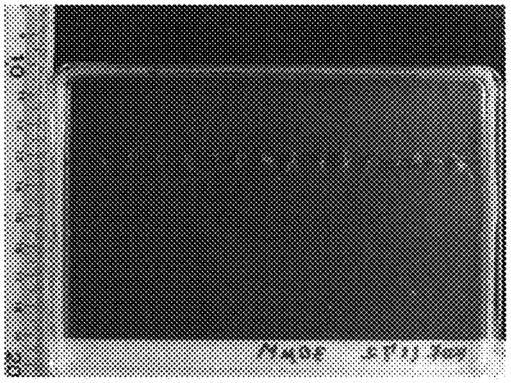
KOK1172
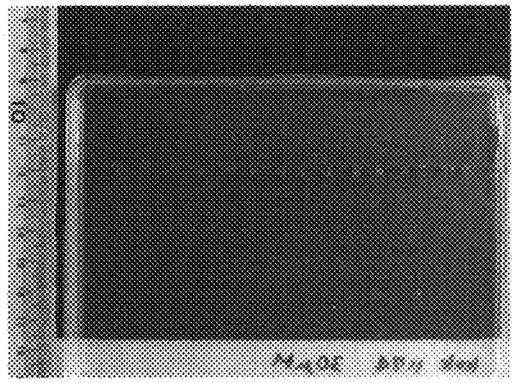
KOK1174
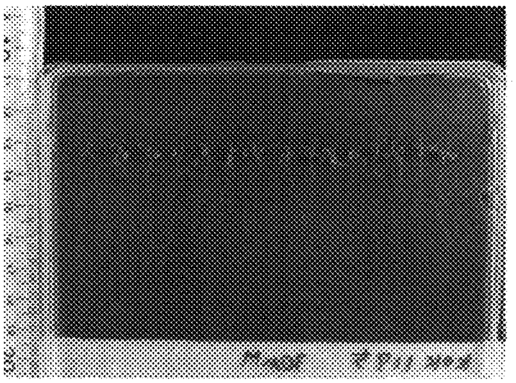
KOK1175
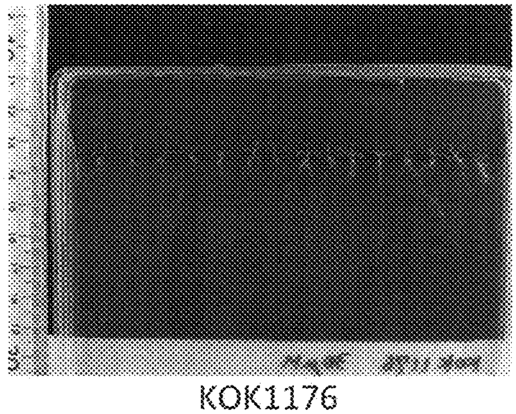
KOK1176
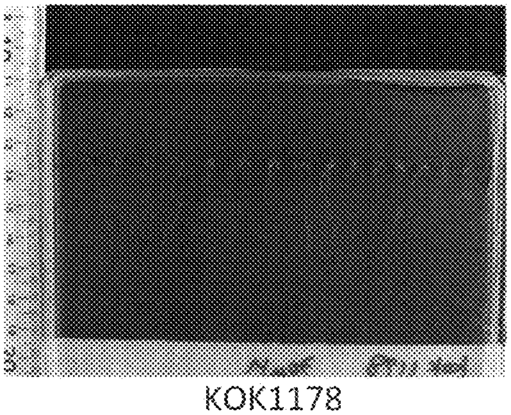
KOK1178

Fig. 4-5
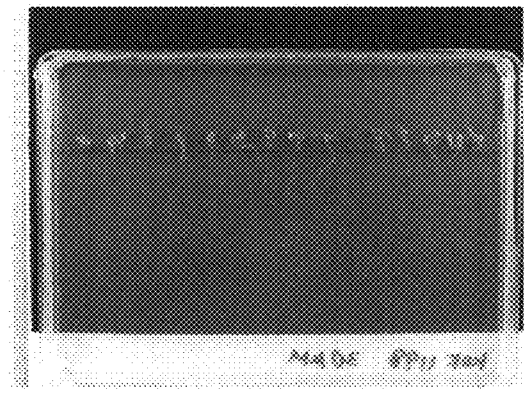
KOK1198
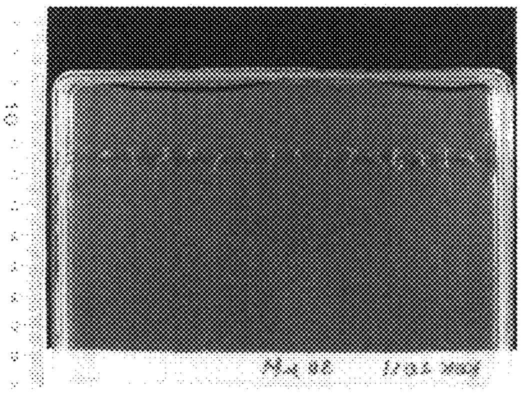
KOK2011
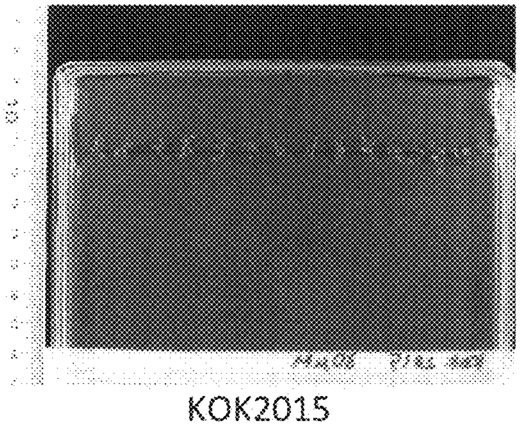
KOK2015
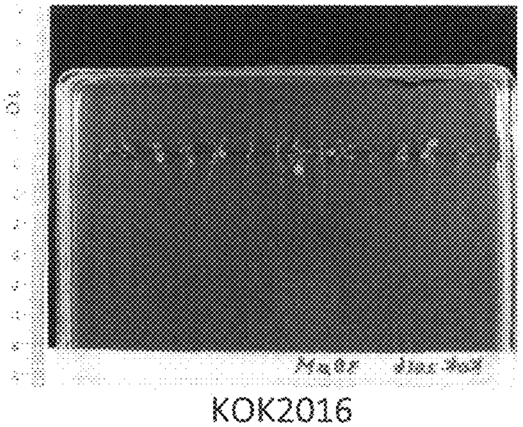
KOK2016
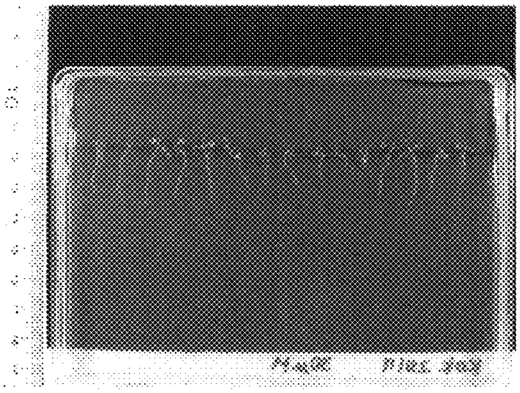
KOK2017
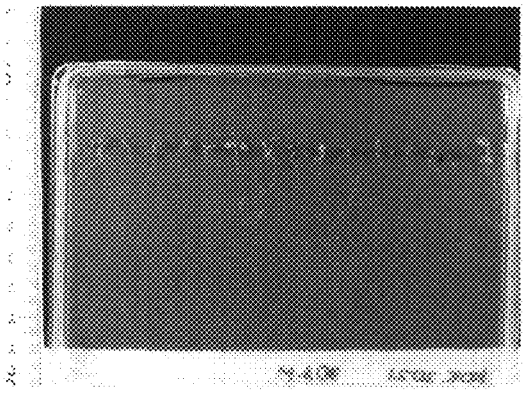
KOK2021

Fig. 4-6
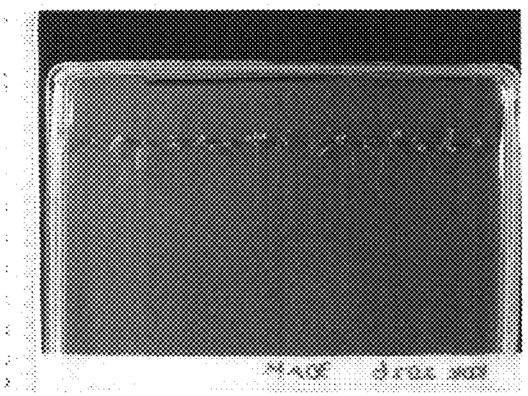
KOK2026
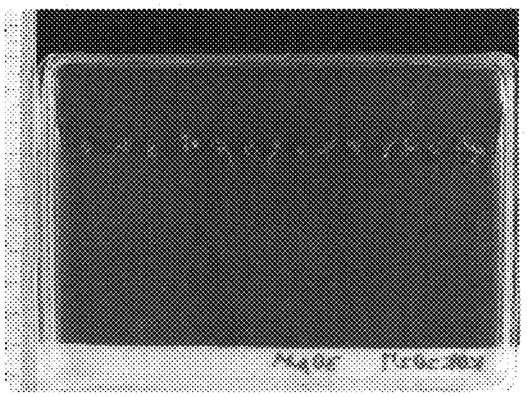
KOK2027
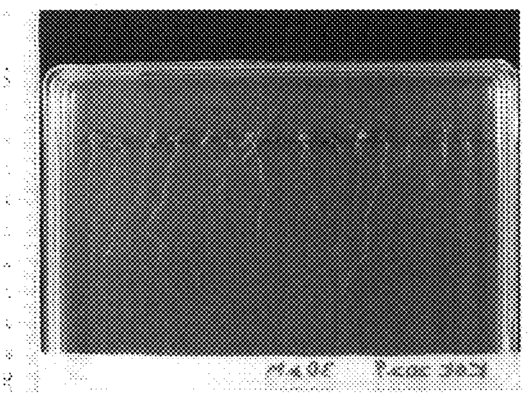
KOK2029
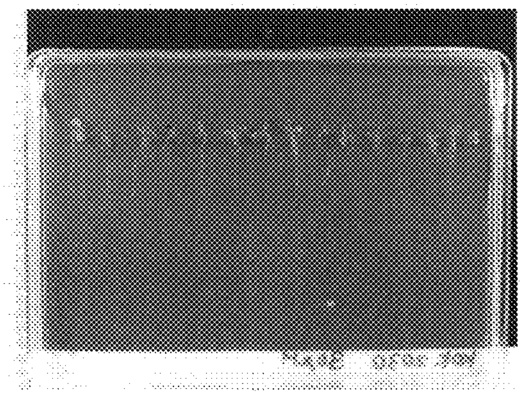
KOK2030
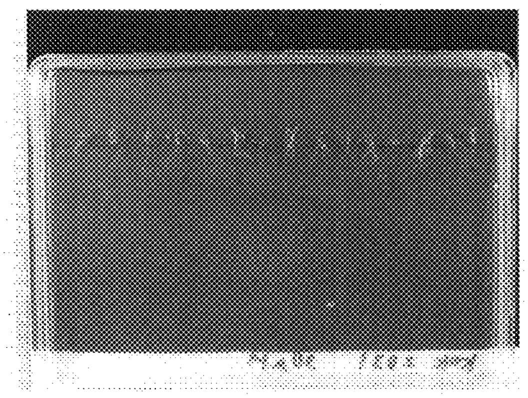
KOK2031
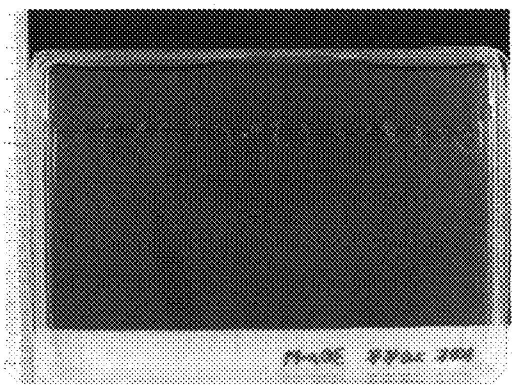
KOK2044

Fig. 4-7
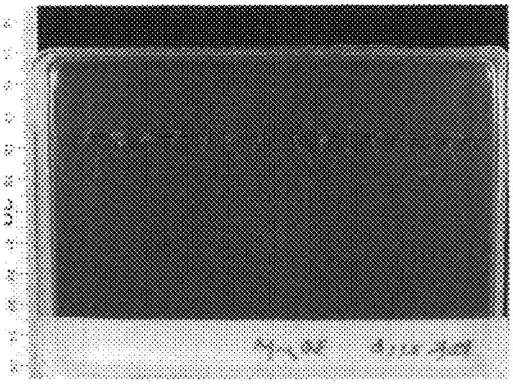
KOK2116
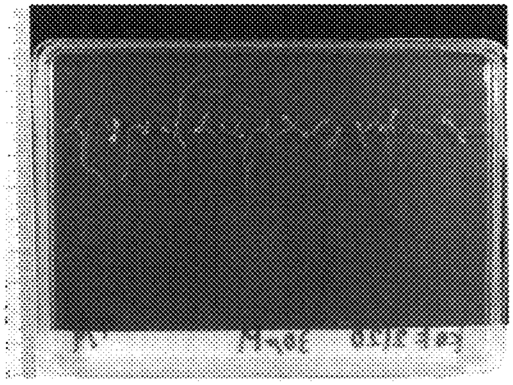
KOK2120
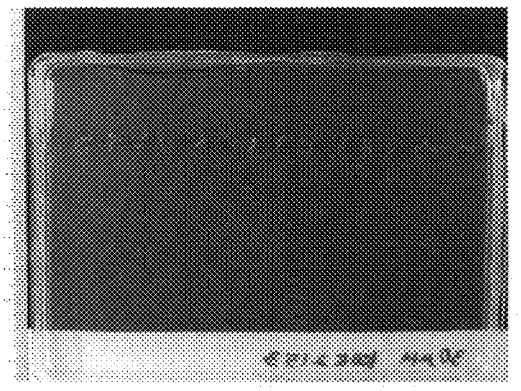
KOK2153
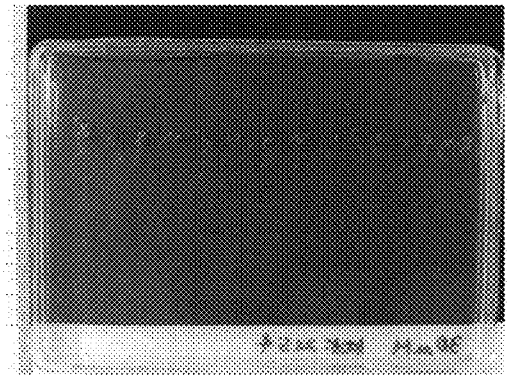
KOK2154
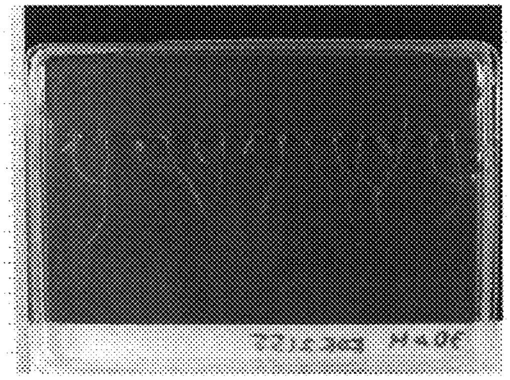
KOK2155
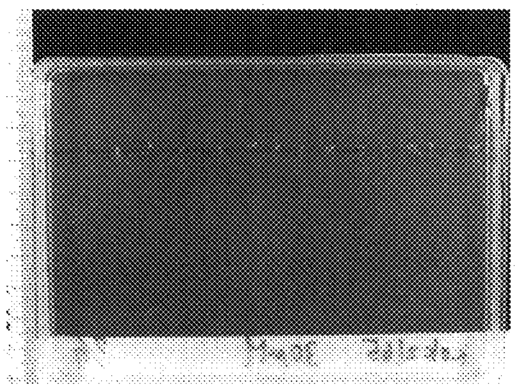
KOK2165

Fig. 4-8
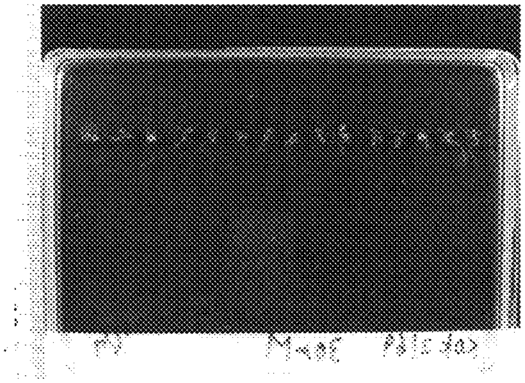
KOK2169
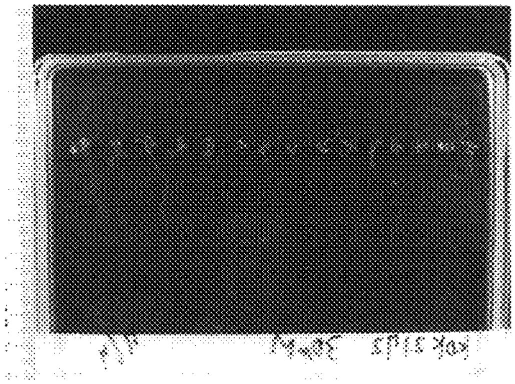
KOK2172
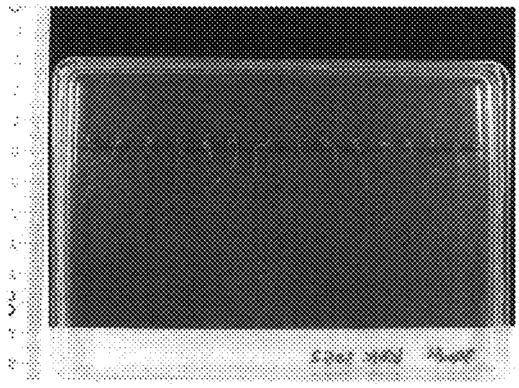
KOK3052
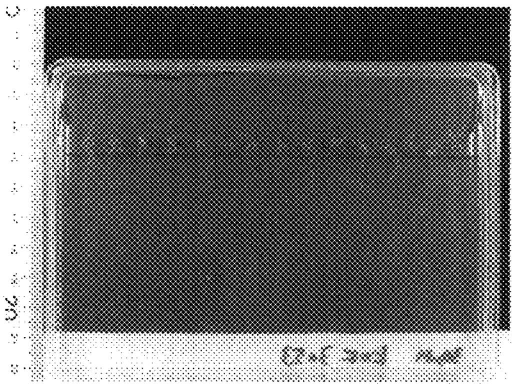
KOK3053

Fig. 5-2
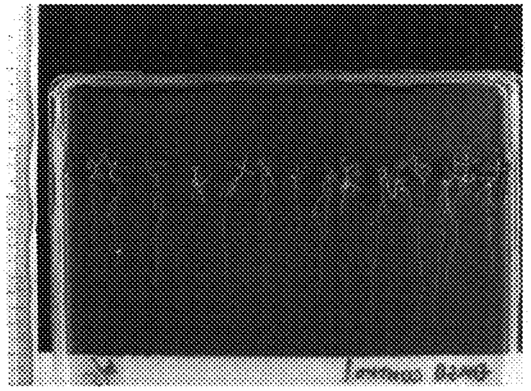
DMSO control
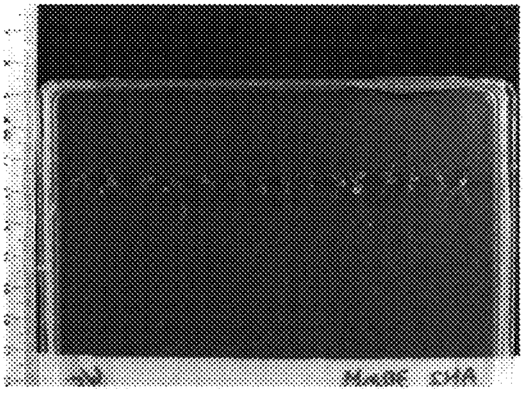
30 μM KOK1160
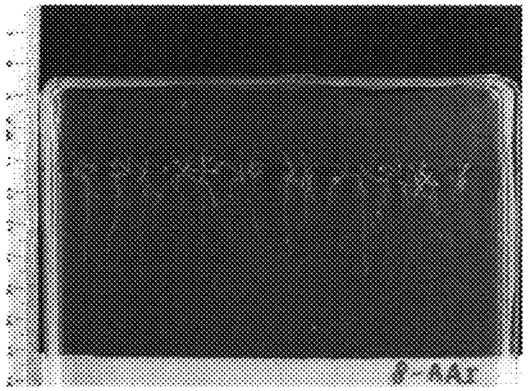
10 nM IAA
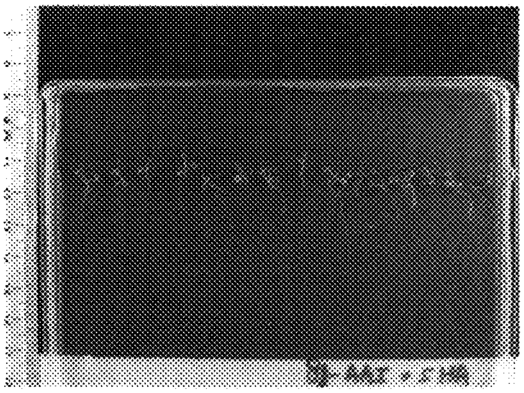
30 μM KOK1160 + 10 nM IAA Fig. 5-3
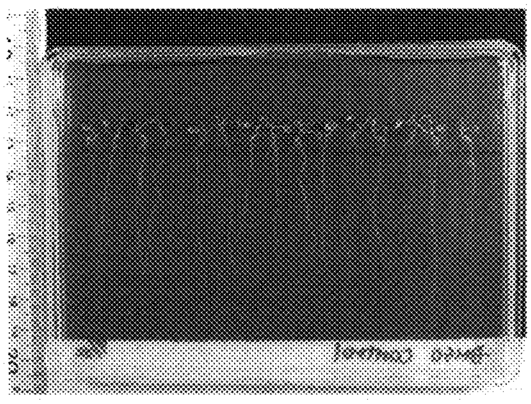
DMSO control
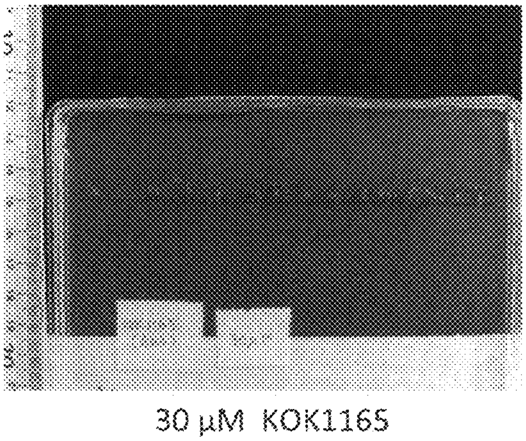
30 μM KOK1165
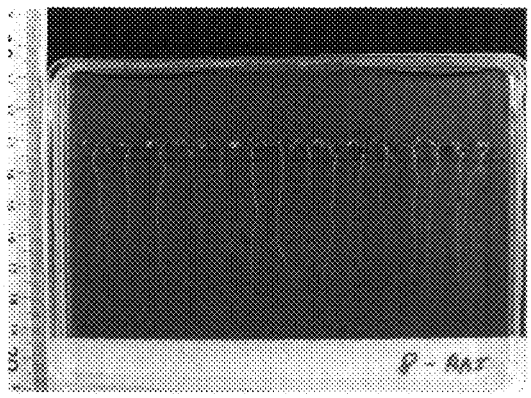
10 nM IAA
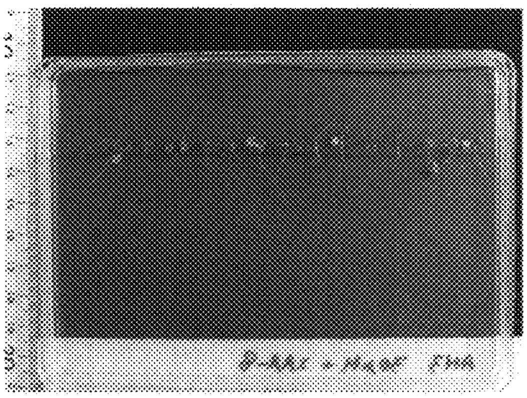
30 μM KOK1165 + 10 nM IAA Fig. 5-4
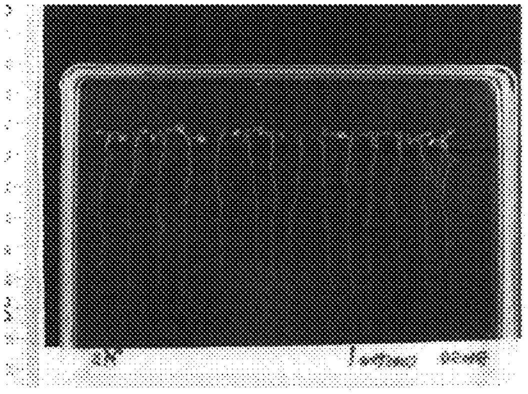
DMSO control
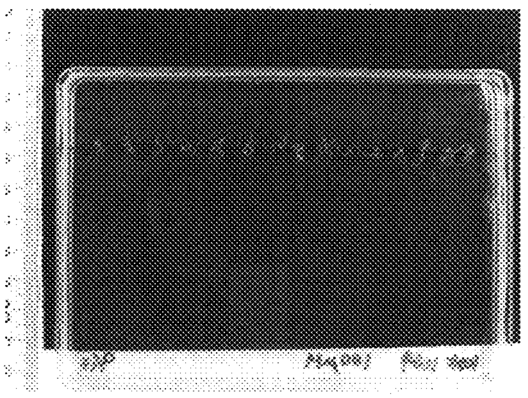
100 μM KOK1169
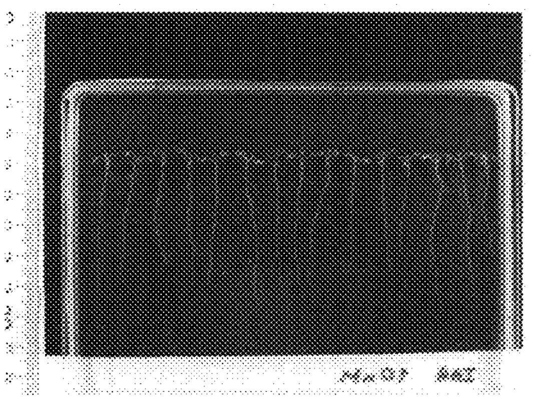
10 nM IAA
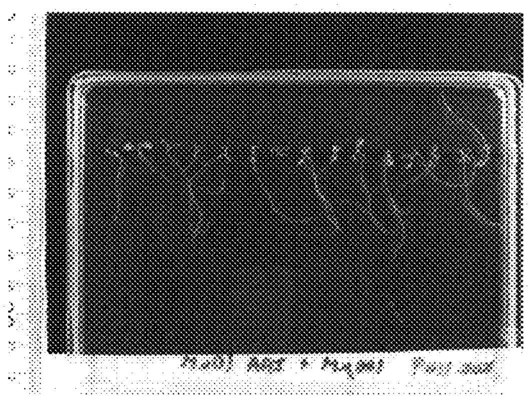
100 μM KOK1169 + 10 nM IAA Fig. 6-1
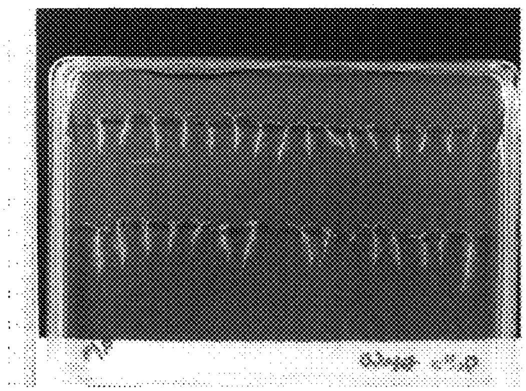
Preculture
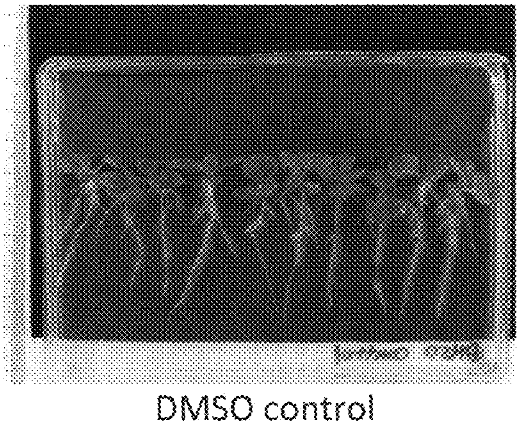
DMSO control
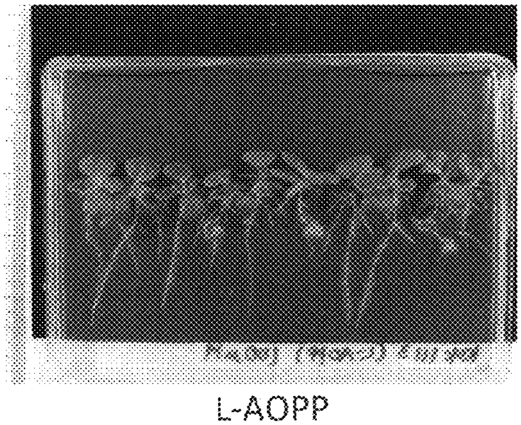
L-AOPP
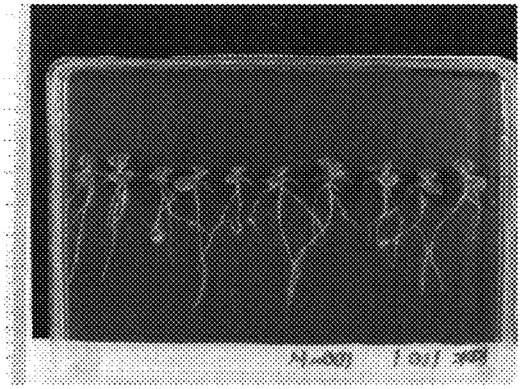
KOK1101
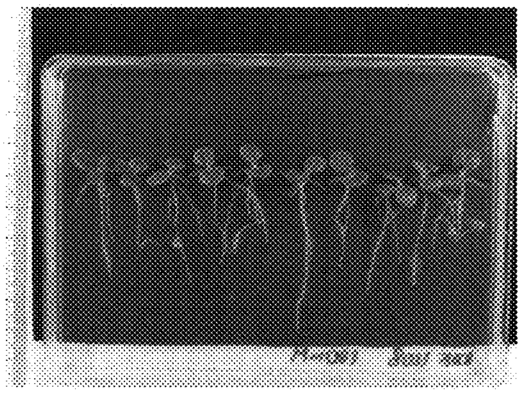
KOK1108

Fig. 6-2
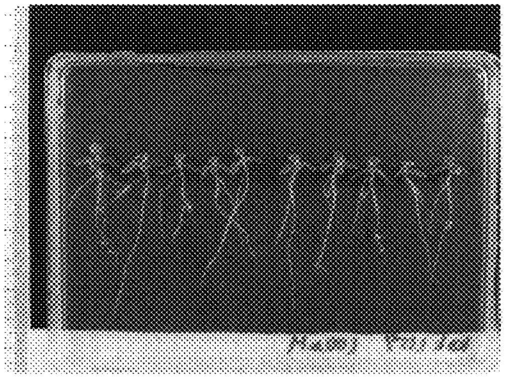
KOK1157
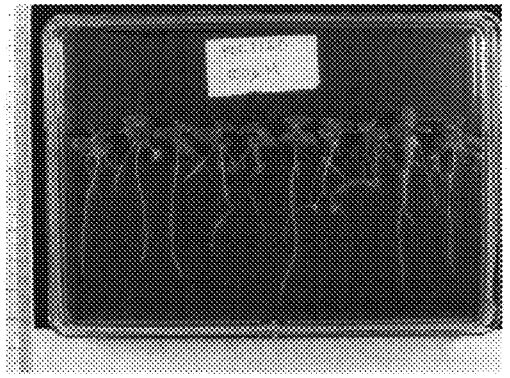
KOK1160
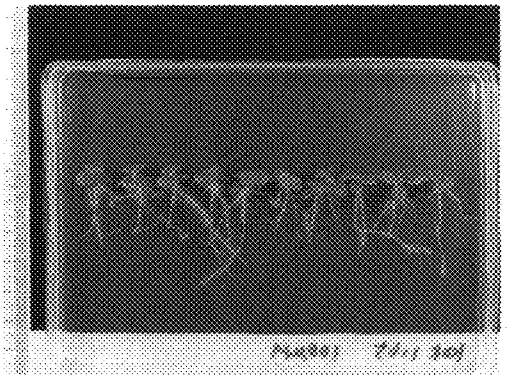
KOK1165
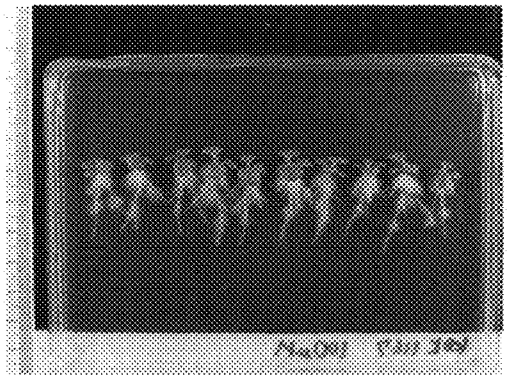
KOK1167
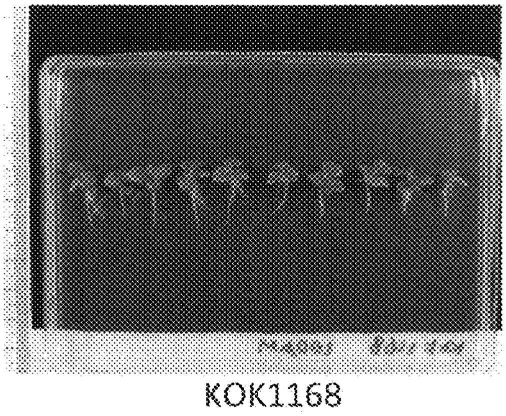
KOK1168
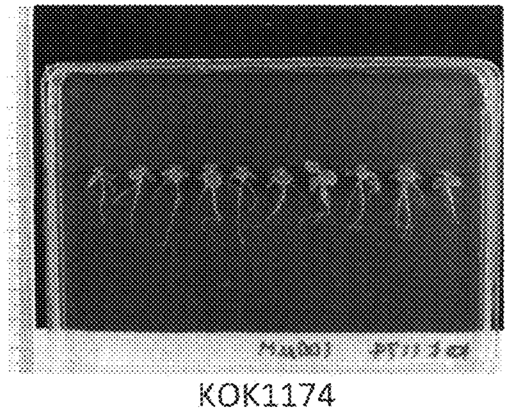
KOK1174

Fig. 6-3
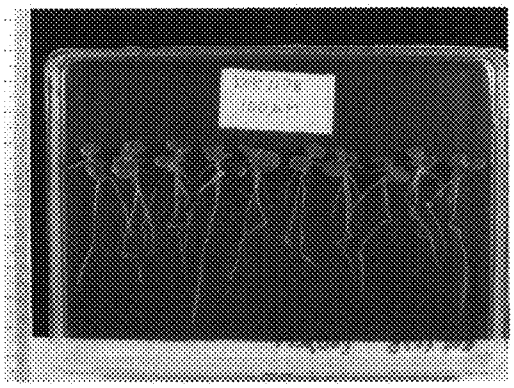
KOK1178
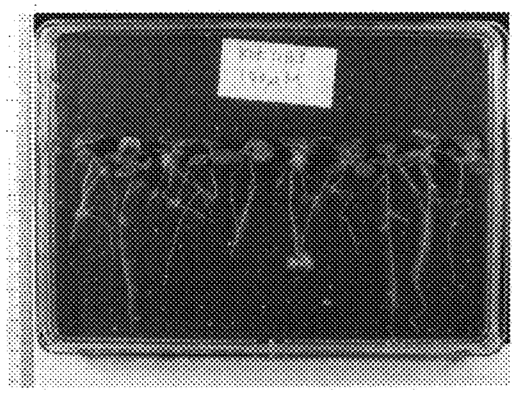
KOK1183
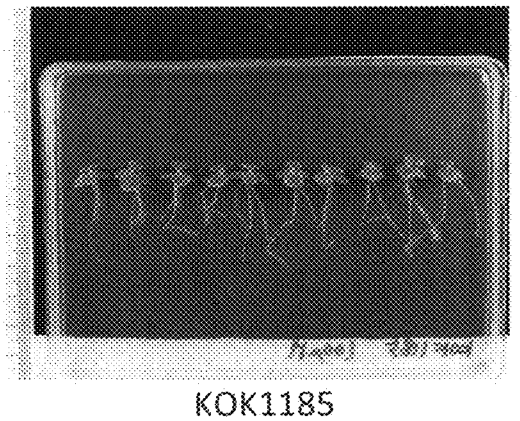
KOK1185
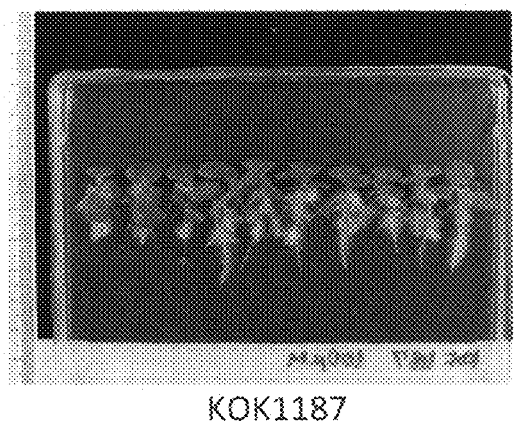
KOK1187
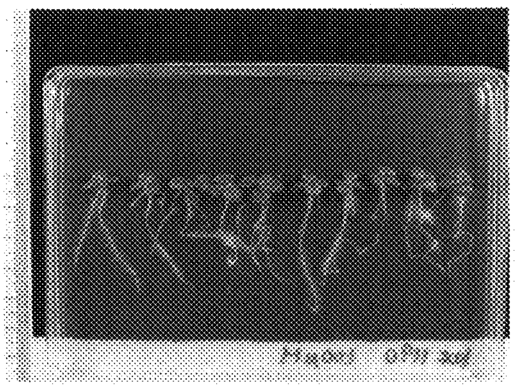
KOK1190
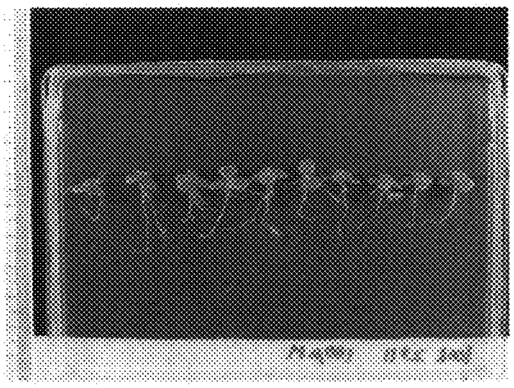
KOK2011

KOK2031

DMSO control

KOK1101

DMSO control 100 µM KOK1168

AUXIN BIOSYNTHESIS INHIBITOR

TECHNICAL FIELD

The present invention relates to an auxin biosynthesis inhibitor, and an inhibitor of tryptophan aminotransferase working in the auxin biosynthetic pathway, as well as methods for using the inhibitors.

BACKGROUND ART

Auxin is a class of plant hormones and involved in various phases such as development, growth and environmental responses of plants. The substance most ubiquitously present as a natural auxin is indole acetic acid (IAA) and natural auxins such as indolebutyric acid (IBA) and 4-chloroindoleacetic acid are also known. In contrast, as synthetic auxins, p-chlorophenoxyacetic acid, 2,4-dichlorophenoxyacetic acid (2,4-D), 2-methyl-4-chlorophenoxybutyric acid (MCPB) and the like are known.

IAA, a natural auxin, is instable. In addition, a plant has a decomposition pathway thereof within the body. Therefore, a synthetic auxin is generally used for agriculture. For example, p-chlorophenoxyacetic acid is used as a fruit set accelerator for tomatoes and eggplants. Furthermore, 2,4-D is used as a herbicide and an agent for culturing a plant tissue, and MCPB is a selective herbicide used in rice paddies.

Auxins are biologically synthesized through complicated pathways. To be more specific, the presence of two pathways through or not through L-tryptophan has been confirmed. The pathway through L-tryptophan is further branched in 4 or more pathways, which are separately catalyzed by different enzymes (FIG. 1). Up to present, as substances inhibiting biosynthesis of auxin, L-α-(2-aminoethoxyvinyl)glycine (AVG), L-aminooxyphenylpropionic acid (L-AOPP), aminooxyacetic acid (AOA) and 2-aminooxyisobutyric acid (AOIBA) are known (Patent Literature 1).

CITATION LIST

Patent Literature

Patent Literature 1: International Publication WO2008-150031

SUMMARY OF INVENTION

L-AOPP known as an auxin biosynthesis inhibitor has low stability. Therefore, even if it is used in a medium, a growth inhibitory effect on plants is rarely observed. In addition, L-AOPP has so far been long used as an inhibitor of phenylalanineammonia-lyase (PAL). Since L-AOPP inhibits PAL, synthesis of important secondary metabolites, such as anthocyanin, flavonoid and lignin, is inhibited and synthesis of a plant hormone, i.e., salicylic acid, is further inhibited. Such side effects occur.

Accordingly, an object of the present invention is to provide an auxin biosynthesis inhibitor superior to L-AOPP.

The present inventors conducted intensive studies. As a result, they found that by modifying a phenyl group, a carboxyl group and an aminooxy group of L-AOPP the substrate specificity, permeability and stability of the resulting compound can be improved and the side effects can be reduced.

To describe more specifically, the present invention include the followings.

(1) A compound represented by general formula (I):

Formula 1

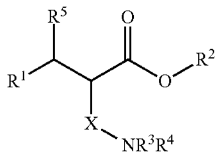

(I)

wherein, $R^1$ is a substituted or unsubstituted aryl group (provided that unsubstituted phenyl is excluded), a substituted or unsubstituted heteroaryl group, a substituted or unsubstituted heterocycloalkyl group, a substituted or unsubstituted aryl-fused cycloalkyl group, or a substituted or unsubstituted aryl-fused heterocycloalkyl group;

$R^2$ is hydrogen or a substituted or unsubstituted alkyl group;

$R^3$ and $R^4$, which are the same or different, are each hydrogen or a substituted or unsubstituted acyl group, or $R^3$ and $R^4$ together form a substituted or unsubstituted alkylidene group or, together with a nitrogen atom to which $R^3$ and $R^4$ are bound, form a substituted or unsubstituted cyclic imide group;

$R^5$ is hydrogen or a substituted or unsubstituted alkyl; and

X is O, NH or $CH_2$, or a salt or solvate thereof.

(2) The compound, or a salt or solvate thereof according to (1), wherein $R^1$ is chlorophenyl, bromophenyl, biphenyl, phenoxyphenyl, 4-chloro-3-methylphenyl, 4-chloro-2-methylphenyl, dichlorophenyl, 6-methoxy-2-naphthyl, naphthyl or quinolinyl;

$R^2$ is $C_{1-6}$ alkyl;

$R^3$ is hydrogen and $R^4$ is acetyl or benzoyl, or $R^3$ and $R^4$ together form propan-2-ylidene or, together with a nitrogen atom to which $R^3$ and $R^4$ are bound, form phthalimide or succinimide;

$R^5$ is hydrogen; and

X is O.

(3) An auxin biosynthesis inhibitor comprising a compound represented by general formula (I'):

Formula 2

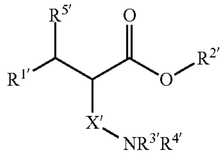

(I')

wherein, $R^{1'}$ is a substituted or unsubstituted aryl group, a substituted or unsubstituted heteroaryl group, a substituted or unsubstituted heterocycloalkyl group, a substituted or unsubstituted aryl-fused cycloalkyl group, or a substituted or unsubstituted aryl-fused heterocycloalkyl group;

$R^{2'}$ is hydrogen or a substituted or unsubstituted alkyl group;

$R^{3'}$ and $R^{4'}$, which are the same or different, are each hydrogen or a substituted or unsubstituted acyl group, or $R^{3'}$ and $R^{4'}$ together form a substituted or unsubstituted alkylidene group or, together with a nitrogen atom to which $R^{3'}$ and $R^{4'}$ are bound, form a substituted or unsubstituted cyclic imide group;

$R^{5'}$ is hydrogen or a substituted or unsubstituted alkyl; and

X' is O, NH or $CH_2$ provided that when $R^{1'}$ is unsubstituted phenyl, $R^{2'}$, $R^{3'}$ and $R^{4'}$ are not hydrogen at the same time), or a salt or solvate thereof.

(4) The auxin biosynthesis inhibitor according to (3), wherein $R^{1'}$ is chlorophenyl, bromophenyl, biphenyl, phenoxyphenyl, 4-chloro-3-methylphenyl, 4-chloro-2-methylphenyl, dichlorophenyl, 6-methoxy-2-naphthyl, naphthyl or quinolinyl;

$R^{2'}$ is $C_{1-6}$ alkyl;

$R^{3'}$ is hydrogen and $R^{4'}$ is acetyl or benzoyl, or $R^{3'}$ and $R^{4'}$ together form propan-2-ylidene or, together with a nitrogen atom to which $R^{3'}$ and $R^{4'}$ are bound, form phthalimide or succinimide;

$R^{5'}$ is hydrogen; and

X' is O.

(5) A tryptophan aminotransferase inhibitor comprising a compound represented by general formula (I"):

Formula 3

(I")

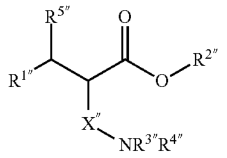

wherein, $R^{1''}$ is a substituted or unsubstituted aryl group (provided that unsubstituted phenyl is excluded), a substituted or unsubstituted heteroaryl group, a substituted or unsubstituted heterocycloalkyl group, a substituted or unsubstituted aryl-fused cycloalkyl group, or a substituted or unsubstituted aryl-fused heterocycloalkyl group;

$R^{2''}$ is hydrogen;

$R^{3''}$ and $R^{4''}$ are each hydrogen;

$R^{5''}$ is hydrogen; and

X" is O, NH or $CH_2$, or a salt, solvate or a prodrug thereof.

(6) The tryptophan aminotransferase inhibitor according to (5), wherein $R^{1''}$ is bromophenyl, biphenyl, phenoxyphenyl, 4-chloro-3-methylphenyl, 6-methoxy-2-naphthyl, naphthyl or quinolinyl;

$R^{2''}$ is hydrogen;

$R^{3''}$ and $R^{4''}$ are each hydrogen;

$R^{5''}$ is hydrogen; and

X" is O, NH or $CH_2$.

(7) A method for inhibiting biosynthesis of auxin in a plant, comprising applying the auxin biosynthesis inhibitor according to (3) or (4) to the plant.

(8) A method for inhibiting tryptophan aminotransferase in a plant, comprising applying the tryptophan aminotransferase inhibitor according to (5) or (6) to the plant.

(9) A method for inhibiting tryptophan aminotransferase, comprising bringing the tryptophan aminotransferase inhibitor according to (5) or (6) into contact with the tryptophan aminotransferase in vitro.

(10) A method for regulating growth of a plant, comprising applying the compound according to (1) or (2), the auxin biosynthesis inhibitor according to (3) or (4), or the tryptophan aminotransferase inhibitor according to (5) or (6) to the plant.

(11) A method for weeding a plant, comprising applying the compound according to (1) or (2), the auxin biosynthesis inhibitor according to (3) or (4), or the tryptophan aminotransferase inhibitor according to (5) or (6) to the plant.

The specification incorporates the content of the specification and/or the drawings of JP Patent Application No. 2011-43277 upon which the priority right of the present application is based.

BRIEF DESCRIPTION OF DRAWINGS

The patent or application file contains at least one drawing executed in color. Copies of this patent or patent application publication with color drawing(s) will be provided by the Office upon request and payment of necessary fee.

FIG. 1 shows auxin biosynthetic pathways.

FIG. 2-1 shows synthetic pathways of the compounds of the present invention.

FIG. 2-2 shows synthetic pathways of the compounds of the present invention.

FIG. 2-3 shows synthetic pathways of the compounds of the present invention.

FIG. 2-4 shows synthetic pathways of the compounds of the present invention.

FIG. 2-5 shows a synthetic pathway of the compounds of the present invention.

FIG. 2-6 shows a synthetic pathway of the compounds of the present invention.

FIG. 2-7 shows synthetic pathways of the compounds of the present invention.

FIG. 2-8 shows synthetic pathways of the compounds of the present invention.

FIG. 2-9 shows synthetic pathways of the compounds of the present invention.

FIG. 2-10 shows a synthetic pathway of the compounds of the present invention.

FIG. 2-11 shows a synthetic pathway of the compound of the present invention.

FIG. 2-12 shows a synthetic pathway of the compounds of the present invention.

FIG. 2-13 shows a synthetic pathway of the compounds of the present invention.

FIG. 2-14 shows a synthetic pathway of the compounds of the present invention.

FIG. 2-15 shows a synthetic pathway of the compounds of the present invention.

FIG. 2-16 shows a synthetic pathway of the compounds of the present invention.

FIG. 2-17 shows a synthetic pathway of the compounds of the present invention.

FIG. 2-18 shows a synthetic pathway of the compounds of the present invention.

FIG. 2-19 shows a synthetic pathway of the compound of the present invention.

FIG. 3 shows endogenous amounts (relative value) of IAA in *arabidopsis* treated with the compound of the present invention.

FIG. 4-1 shows morphology of *arabidopsis* cultured with the compound of the present invention.

FIG. 4-2 shows morphology of *arabidopsis* cultured with the compound of the present invention.

FIG. 4-3 shows morphology of *arabidopsis* cultured with the compound of the present invention.

FIG. 4-4 shows morphology of *arabidopsis* cultured with the compound of the present invention.

FIG. 4-5 shows morphology of *arabidopsis* cultured with the compound of the present invention.

FIG. 4-6 shows morphology of *arabidopsis* cultured with the compound of the present invention.

FIG. 4-7 shows morphology of *arabidopsis* cultured with the compound of the present invention.

FIG. 4-8 shows morphology of *arabidopsis* cultured with the compound of the present invention.

FIG. 5-1 shows morphology of *arabidopsis* cultured with the compound of the present invention and IAA.

FIG. 5-2 shows morphology of *arabidopsis* cultured with the compound of the present invention and IAA.

FIG. 5-3 shows morphology of *arabidopsis* cultured with the compound of the present invention and IAA.

FIG. 5-4 shows morphology of *arabidopsis* cultured with the compound of the present invention and IAA.

FIG. 6-1 shows morphology of tobacco cultured with the compound of the present invention.

FIG. 6-2 shows morphology of tobacco cultured with the compound of the present invention.

FIG. 6-3 shows morphology of tobacco cultured with the compound of the present invention.

FIG. 6-4 shows morphology of tobacco cultured with the compound of the present invention.

FIG. 7 shows morphology of lettuce cultured with the compound of the present invention.

FIG. 8 shows the results of TAA1 inhibitory test.

FIG. 9 shows the results of PAL2 inhibitory test.

FIG. 10 shows morphology of rice treated with the compound of the present invention.

FIG. 11 shows morphology of tomato treated with the compound of the present invention.

FIG. 12 shows morphology of *Physcomitrella patens* subsp. *Patens* treated with the compound of the present invention.

DESCRIPTION OF EMBODIMENTS

Figures 1, 2:
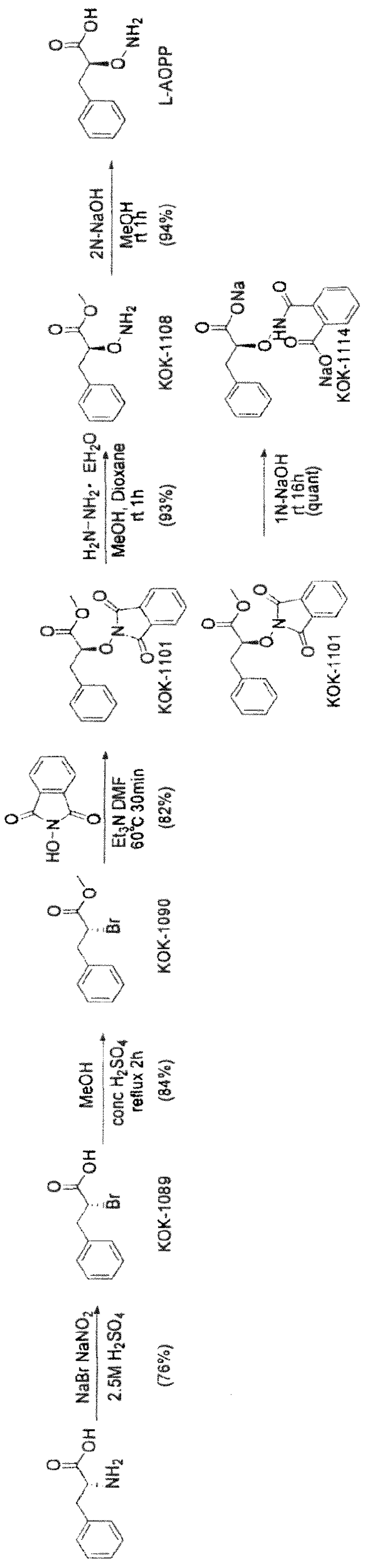
Figure 2:
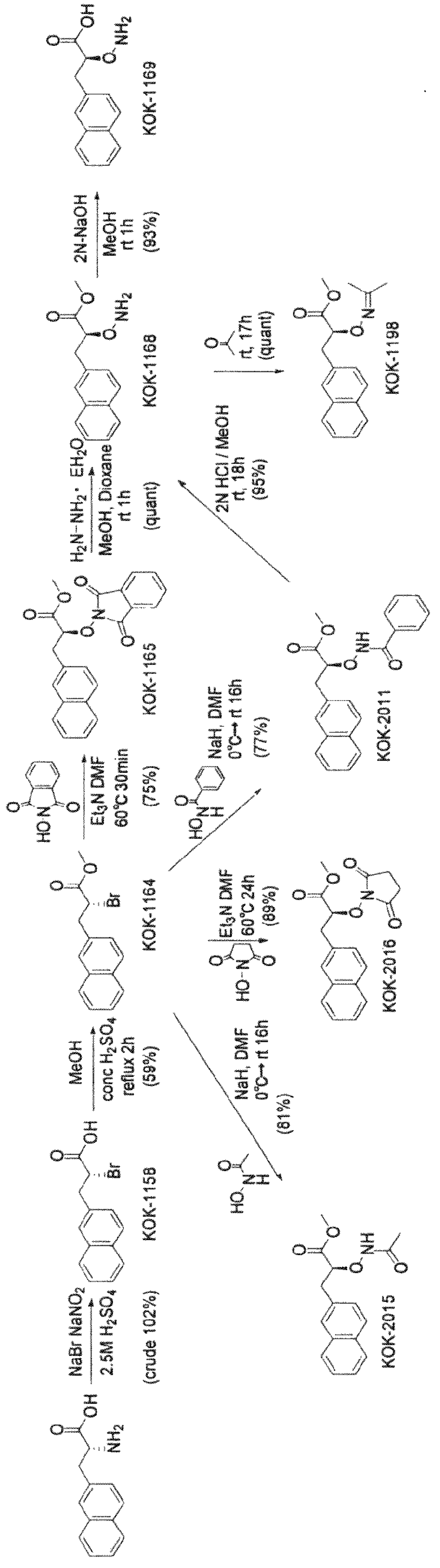

Now, the present invention will be more specifically described below.

1. Compound

The present invention relates to a compound represented by general formula (I):

Formula 4

(I)

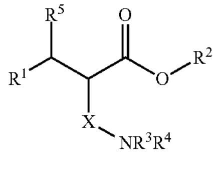

wherein, $R^1$ to $R^5$ and X are the same as defined below, or a salt or solvate thereof.

If the compound of the present invention has a single or a plurality of chiral centers, individual enantiomers and diastereomers as well as racemates are included in the present invention. The same applies to the auxin biosynthesis inhibitor and tryptophan aminotransferase inhibitor described below.

In general formula (I), $R^1$ is a substituted or unsubstituted aryl group (provided that unsubstituted phenyl is excluded), a substituted or unsubstituted heteroaryl group, a substituted or unsubstituted heterocycloalkyl group, a substituted or unsubstituted aryl-fused cycloalkyl group, or a substituted or unsubstituted aryl-fused heterocycloalkyl group. Preferably, $R^1$ is a substituted or unsubstituted aryl group (provided that unsubstituted phenyl is excluded), a substituted or unsubstituted heteroaryl group or a substituted or unsubstituted heterocycloalkyl group. More preferably, $R^1$ is a substituted aryl group, a substituted or unsubstituted heteroaryl group or a substituted or unsubstituted heterocycloalkyl group. Particularly preferably, $R^1$ is a substituted aryl group or a substituted or unsubstituted heteroaryl group.

Each of the groups represented by $R^1$ may be substituted with substituents such as halogen (for example, fluorine, chlorine, bromine, iodine), an alkyl group (for example, $C_{1-6}$ alkyl, $C_{1-3}$ alkyl), a haloalkyl group (for example, $C_{1-3}$ haloalkyl, trifluoromethyl), a cycloalkyl group (for example, $C_{3-7}$ cycloalkyl, $C_{5-6}$ cycloalkyl), an alkoxy group (for example, $C_{1-6}$ alkoxy, $C_{1-3}$ alkoxy), a haloalkoxy group (for example, $C_{1-6}$ haloalkoxy, $C_{1-3}$ haloalkoxy, trifluoromethoxy), an aryl group (for example, $C_{6-10}$ aryl, phenyl), an aryl-substituted phenyl group (for example, $C_{6-10}$ aryl-substituted phenyl, biphenyl), a heteroaryl group (for example, thiophene), an aryl-substituted heteroaryl group (for example, $C_{6-10}$ aryl-substituted heteroaryl, phenylthiophene), an aryloxy group (for example, $C_{6-10}$ aryloxy, phenyloxy), an oxo group, an amino group, a nitro group and a cyano group.

Examples of the aryl group represented by $R^1$ include $C_{6-14}$ aryl and $C_{6-10}$ aryl. Particularly, chlorophenyl, bromophenyl, biphenyl, phenoxyphenyl, 4-chloro-3-methylphenyl, 4-chloro-2-methylphenyl, dichlorophenyl, 6-methoxy-2-naphthyl, 4-(4'-chlorophenyl)phenyl and naphthyl are preferable. Particularly, naphthyl is preferable.

Examples of the heteroaryl group represented by $R^1$ include a 5 to 10 membered heteroaryl and 5 or 6-membered heteroaryl having 1 to 3 hetero atoms selected from nitrogen, oxygen and sulfur as ring member(s). Particularly, indolyl, quinolinyl, isoquinolinyl, quinoxalinyl, cinnolinyl, benzothiazolyl, thiazolyl, benzoxazolyl and benzothiophene are preferable.

Examples of the heterocycloalkyl group represented by $R^1$ include a 5 to 10 membered heterocycloalkyl and 5 or 6-membered heterocycloalkyl having 1 to 3 hetero atoms selected from nitrogen, oxygen and sulfur as ring member(s). Particularly, phenylpiperidinyl is preferable.

Examples of the aryl-fused cycloalkyl group represented by $R^1$ include groups in which phenyl is fused to $C_{5-6}$ cycloalkyl. Particularly, groups having a structure shown below are preferable:

Formula 5

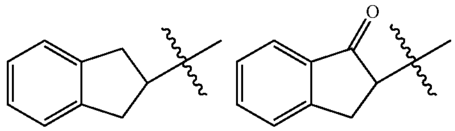

Examples of the aryl-fused heterocycloalkyl group represented by $R^1$ include groups in which phenyl is fused to a 5 or 6-membered heterocycloalkyl having 1 to 3 hetero atoms selected from nitrogen, oxygen and sulfur as ring member(s). Particularly, groups having a structure shown below are preferable:

Formula 6

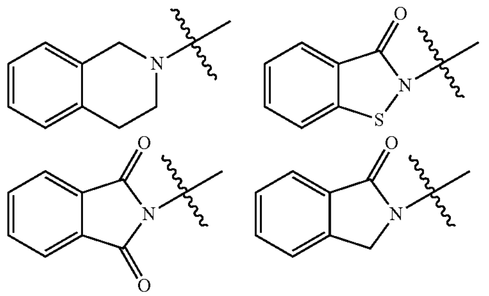

In general formula (I), $R^2$ is hydrogen or a substituted or unsubstituted alkyl group. Preferably, $R^2$ is a substituted or unsubstituted alkyl group.

The alkyl group represented by $R^2$ may be substituted with halogen (for example, fluorine, chlorine, bromine, iodine), a cycloalkyl group (for example, $C_{3-7}$ cycloalkyl, $C_{5-6}$ cycloalkyl), an alkoxy group (for example, $C_{1-6}$ alkoxy, $C_{1-3}$ alkoxy).

Examples of the alkyl group represented by $R^2$ include $C_{1-6}$ alkyl and $C_{1-4}$ alkyl. Particularly, methyl, ethyl and butyl are preferable.

In general formula (I), $R^3$ and $R^4$, which are the same or different, are each hydrogen or a substituted or unsubstituted acyl group, or $R^3$ and $R^4$ together form a substituted or unsubstituted alkylidene group or, together with a nitrogen atom to which $R^3$ and $R^4$ are bound, form a substituted or unsubstituted cyclic imide group. Preferably, $R^3$ is hydrogen and $R^4$ is a substituted or unsubstituted acyl group, or $R^3$ and $R^4$ together form a substituted or unsubstituted alkylidene group or, together with a nitrogen atom to which $R^3$ and $R^4$ are bound, form a substituted or unsubstituted cyclic imide group.

Examples of the acyl group represented by $R^3$ and $R^4$ may be substituted with substituents such as halogen (for example, fluorine, chlorine, bromine, iodine), a cycloalkyl group (for example, $C_{3-7}$ cycloalkyl, $C_{5-6}$ cycloalkyl), an alkoxy group (for example, $C_{1-6}$ alkoxy, $C_{1-3}$ alkoxy) and a carboxyl group. Furthermore, if the acyl group has an aromatic moiety, the aromatic moiety may be further substituted with substituents such as an alkyl group (for example, $C_{1-6}$ alkyl, $C_{1-3}$ alkyl), a haloalkyl group (for example, $C_{1-3}$ haloalkyl, trifluoromethyl), an amino group, a nitro group and a cyano group.

The alkylidene group that $R^3$ and $R^4$ form may be substituted with substituents such as halogen (for example, fluorine, chlorine, bromine, iodine), a cycloalkyl group (for example, $C_{3-7}$ cycloalkyl, $C_{5-6}$ cycloalkyl) and an alkoxy group (for example, $C_{1-6}$ alkoxy, $C_{1-3}$ alkoxy).

The cyclic imide group that $R^3$ and $R^4$ form, together with a nitrogen atom, may be substituted with substituents such as halogen (for example, fluorine, chlorine, bromine, iodine), an alkyl group (for example, $C_{1-6}$ alkyl, $C_{1-3}$ alkyl), a haloalkyl group (for example, $C_{1-3}$ haloalkyl, trifluoromethyl), a cycloalkyl group (for example, $C_{3-7}$ cycloalkyl, $C_{5-6}$ cycloalkyl) and an alkoxy group (for example, $C_{1-6}$ alkoxy, $C_{1-3}$ alkoxy).

Examples of the acyl group represented by $R^3$ and $R^4$ include $C_{2-11}$ acyl and $C_{2-7}$ acyl. Particularly, acetyl and benzoyl are preferable.

Examples of the alkylidene group that $R^3$ and $R^4$ form include $C_{3-10}$ alkylidene and $C_{3-6}$ alkylidene. Particularly, propan-2-ylidene is preferable.

Examples of the cyclic imide group that $R^3$ and $R^4$ form, together with nitrogen atom include $C_{4-8}$ cyclic imide. Particularly, phthalimide and succinimide are preferable.

In general formula (I), $R^5$ is hydrogen or a substituted or unsubstituted alkyl. Preferably, $R^5$ is hydrogen.

The alkyl group represented by $R^5$ may be substituted with substituents such as halogen (for example, fluorine, chlorine, bromine, iodine), a cycloalkyl group (for example, $C_{3-7}$ cycloalkyl, $C_{5-6}$ cycloalkyl), and an alkoxy group (for example, $C_{1-6}$ alkoxy and $C_{1-3}$ alkoxy).

Examples of the alkyl group represented by $R^5$ include $C_{1-6}$ alkyl and $C_{1-3}$ alkyl. As the alkyl group, particularly methyl is preferable.

In general formula (I), X is O, $CH_2$ or NH. Preferably, X is O or NH. Particularly preferably, X is O.

The compounds represented by general formula (I) include compounds in which $R^1$ to $R^5$ and X satisfying the aforementioned definitions are arbitrarily employed in combination. Although it is not particularly limited, in view of higher stability, a compound in which $R^2$ to $R^4$ are not hydrogen at the same time, is preferable. For example, a compound, in which $R^2$ is hydrogen; $R^3$ is hydrogen and $R^4$ is a substituted or unsubstituted acyl group, or $R^3$ and $R^4$ together form a substituted or unsubstituted alkylidene group or, together with a nitrogen atom to which $R^3$ and $R^4$ are bound, form a substituted or unsubstituted cyclic imide group, is preferable. Particularly a compound in which $R^2$ is a substituted or unsubstituted alkyl group; $R^3$ is hydrogen and $R^4$ is a substituted or unsubstituted acyl group, or $R^3$ and $R^4$ together form a substituted or unsubstituted alkylidene group or, together with a nitrogen atom to which $R^3$ and $R^4$ are bound, form a substituted or unsubstituted cyclic imide group is particularly preferable.

The salts of a compound represented by general formula (I) are not particularly limited as long as they do not have a negative effect upon the activity of the compound. Examples thereof include salts of an alkaline metal (e.g., a lithium salt, a sodium salt, a potassium salt), salts of an alkaline earth metal (e.g., a magnesium salt, a calcium salt), and acid addition salts (a inorganic acid salt or an organic salt, for example, a hydrochloride, a hydrobromate, a nitrate, a sulfate, a phosphate, an acetate, a phenyl acetate, propionate, butyrate, valerate, maleate, acrylate, fumarate, malate, tartrate, citrate, salicylate, lactate, phthalate, oxalate, succinate, benzoate, formate, ascorbate, palmitate, oleate, benzene sulfonate and tosylate)

The solvates of a compound represented by general formula (I) are not particularly limited as long as they do not have a negative effect upon the activity of the compound. Examples thereof include solvates with an organic solvent such as methanol, ethanol, isopropanol, dimethylsulfoxide (DMSO), acetic acid, ethanolamine and ethyl acetate, and hydrates with water.

An embodiment of the present invention is directed to a compound represented by general formula (I) where $R^1$ is a substituted or unsubstituted aryl group (provided that unsubstituted phenyl is excluded), a substituted or unsubstituted heteroaryl group or a substituted or unsubstituted heterocycloalkyl group; $R^2$ is hydrogen or a substituted or unsubstituted alkyl group; $R^3$ and $R^4$, which are the same or different, are each hydrogen or a substituted or unsubstituted acyl group, or $R^3$ and $R^4$ together form a substituted or unsubstituted alkylidene group or, together with a nitrogen atom to which $R^3$ and $R^4$ are bound, form a substituted or unsubstituted cyclic imide group; $R^5$ is hydrogen or a substituted or unsubstituted alkyl; and X is O or NH; or a salt or solvate thereof.

A preferable embodiment of the present invention is directed to a compound represented by general formula (I) where $R^1$ is a substituted aryl group, a substituted or unsubstituted heteroaryl group or a substituted or unsubstituted heterocycloalkyl group; $R^2$ is hydrogen or a substituted or unsubstituted alkyl group; $R^3$ and $R^4$, which are the same or different, are each hydrogen or a substituted or unsubstituted acyl group, or $R^3$ and $R^4$ together form a substituted or unsubstituted alkylidene group or, together with a nitrogen atom to which $R^3$ and $R^4$ are bound, form a substituted or unsubstituted cyclic imide group; $R^5$ is hydrogen or a substituted or unsubstituted alkyl; and X is O or NH; or a salt or solvate thereof.

Specific examples of the preferable embodiment include a compound represented by general formula (I) where $R^1$ is chlorophenyl, bromophenyl, biphenyl, phenoxyphenyl, 4-chloro-3-methylphenyl, 4-chloro-2-methylphenyl, dichlorophenyl, 6-methoxy-2-naphthyl, naphthyl or quinolinyl; $R^2$ is hydrogen or $C_{1-6}$ alkyl; $R^3$ and $R^4$, which are the same or different, are each hydrogen, acetyl or benzoyl or $R^3$ and $R^4$ together form propan-2-ylidene or, together with a nitrogen atom to which $R^3$ and $R^4$ are bound, form phthalimide or succinimide; $R^5$ is hydrogen or methyl; and X is O or NH; or a salt or solvate thereof.

A further preferable embodiment of the present invention is directed to a compound represented by general formula (I) where $R^1$ is substituted aryl group or a substituted or unsubstituted heteroaryl group; $R^2$ is a substituted or unsubstituted alkyl group; $R^3$ is hydrogen and $R^4$ is a substituted or unsubstituted acyl group, or $R^3$ and $R^4$ together form a substituted or unsubstituted alkylidene group or, together with a nitrogen atom to which $R^3$ and $R^4$ are bound, form a substituted or unsubstituted cyclic imide group; $R^5$ is hydrogen; and X is O or NH; or a salt or solvate thereof.

Specific examples of the further preferable embodiment include a compound represented by general formula (I) where $R^1$ is chlorophenyl, bromophenyl, biphenyl, phenoxyphenyl, 4-chloro-3-methylphenyl, 4-chloro-2-methylphenyl, dichlorophenyl, 6-methoxy-2-naphthyl, naphthyl or quinolinyl; $R^2$ is $C_{1-6}$ alkyl; $R^3$ is hydrogen and $R^4$ is acetyl or benzoyl or $R^3$ and $R^4$ together form propan-2-ylidene or, together with a nitrogen atom to which $R^3$ and $R^4$ are bound, form phthalimide or succinimide; $R^5$ is hydrogen; and X is O or NH; or a salt or solvate thereof.

A particularly preferable embodiment of the present invention is directed to a compound represented by general formula (I) wherein $R^1$ is substituted aryl group or a substituted or unsubstituted heteroaryl group; $R^2$ is a substituted or unsubstituted alkyl group; $R^3$ is hydrogen and $R^4$ is a substituted or unsubstituted acyl group, or $R^3$ and $R^4$ together form a substituted or unsubstituted alkylidene group or, together with a nitrogen atom to which $R^3$ and $R^4$ are bound, form a substituted or unsubstituted cyclic imide group; $R^5$ is hydrogen; and X is O; or a salt or solvate thereof.

Specific examples of the particularly preferable embodiment include a compound represented by general formula (I) where $R^1$ is chlorophenyl, bromophenyl, biphenyl, phenoxyphenyl, 4-chloro-3-methylphenyl, 4-chloro-2-methylphenyl, dichlorophenyl, 6-methoxy-2-naphthyl, naphthyl or quinolinyl; $R^2$ is $C_{1-6}$ alkyl; $R^3$ is hydrogen and $R^4$ is acetyl or benzoyl or $R^3$ and $R^4$ together form propan-2-ylidene or, together with a nitrogen atom to which $R^3$ and $R^4$ are bound, form phthalimide or succinimide; $R^5$ is hydrogen; and X is O; a salt or solvate thereof.

2. Auxin Biosynthesis Inhibitor

The present invention further relates to an auxin biosynthesis inhibitor comprising a compound represented by general formula (I'):

Formula 7

(I')

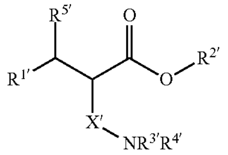

wherein, $R^{1'}$ to $R^{5'}$ and X' are the same as defined below, or a salt or solvate thereof.

In general formula (I'), $R^{1'}$ is a substituted or unsubstituted aryl group, a substituted or unsubstituted heteroaryl group, a substituted or unsubstituted heterocycloalkyl group, a substituted or unsubstituted aryl-fused cycloalkyl group, or a substituted or unsubstituted aryl-fused heterocycloalkyl group. Preferably, $R^{1'}$ is a substituted or unsubstituted aryl group, a substituted or unsubstituted heteroaryl group or a substituted or unsubstituted heterocycloalkyl group. Particularly preferably, $R^{1'}$ is a substituted aryl group or a substituted or unsubstituted heteroaryl group.

In general formula (I'), $R^{2'}$ is hydrogen or a substituted or unsubstituted alkyl group. Preferably, $R^{2'}$ is a substituted or unsubstituted alkyl group.

In general formula (I'), $R^{3'}$ and $R^{4'}$, which are the same or different, are each hydrogen or a substituted or unsubstituted acyl group, or $R^{3'}$ and $R^{4'}$ together form a substituted or unsubstituted alkylidene group or, together with a nitrogen atom to which $R^{3'}$ and $R^{4'}$ are bound, form a substituted or unsubstituted cyclic imide group. Preferably, $R^{3'}$ is hydrogen and $R^{4'}$ is a substituted or unsubstituted acyl group, or $R^{3'}$ and $R^{4'}$ together form a substituted or unsubstituted alkylidene group or, together with a nitrogen atom to which $R^{3'}$ and $R^{4'}$ are bound, form a substituted or unsubstituted cyclic imide group.

In general formula (I'), $R^{5'}$ is hydrogen or a substituted or unsubstituted alkyl. Preferably, $R^{5'}$ is hydrogen.

In general formula (I'), X' is O, $CH_2$ or NH. Preferably, X' is O or NH. Particularly preferably, X' is O.

Specific examples of $R^{1'}$ to $R^{5'}$ of general formula (I') and specific examples of substituents which may substitute for the groups of $R^{1'}$ to $R^{5'}$ are the same as described with respect to $R^1$ to $R^5$ of general formula (I). Note that $R^{1'}$ of general formula (I') may be unsubstituted phenyl; however in this case, $R^{2'}$ to $R^{4'}$ are not hydrogen as the same time.

The compounds represented by general formula (I') include compounds in which $R^{1'}$ to $R^{5'}$ and X' satisfying the aforementioned definitions are arbitrarily employed in combination. Although it is not particularly limited, in view of high stability, a compound in which $R^{2'}$ to $R^{4'}$ are not hydrogen at the same time, is preferable. For example, a compound, in which $R^{2'}$ is hydrogen; $R^{3'}$ is hydrogen and $R^{4'}$ is a substituted or unsubstituted acyl group, or $R^{3'}$ and $R^{4'}$ together form a substituted or unsubstituted alkylidene group or, together with a nitrogen atom to which $R^{3'}$ and $R^{4'}$ are bound, form a substituted or unsubstituted cyclic imide group is preferable. Particularly, a compound, in which $R^{2'}$ is a substituted or unsubstituted alkyl group; $R^{3'}$ is hydrogen and $R^{4'}$ is a substituted or unsubstituted acyl group, or $R^{3'}$ and $R^{4'}$ together form a substituted or unsubstituted alkylidene group or, together with a nitrogen atom to which $R^{3'}$ and $R^{4'}$ are bound, form a substituted or unsubstituted cyclic imide group is particularly preferable.

Specific examples of the salt and solvate of a compound represented by general formula (I') are the same as described with respect to the salt and solvate of a compound represented by general formula (I).

A preferable embodiment of the present invention is directed to an auxin biosynthesis inhibitor containing a compound represented by general formula (I') where $R^{1'}$ is a substituted or unsubstituted aryl group, a substituted or unsubstituted heteroaryl group or a substituted or unsubstituted heterocycloalkyl group; $R^{2'}$ is hydrogen or a substituted or unsubstituted alkyl group; $R^{3'}$ and $R^{4'}$, which are the same or different, are each hydrogen or a substituted or unsubstituted acyl group, or $R^{3'}$ and $R^{4'}$ together form a substituted or unsubstituted alkylidene group or, together with a nitrogen atom to which $R^{3'}$ and $R^{4'}$ are bound, form a substituted or unsubstituted cyclic imide group; $R^{5'}$ is hydrogen or a substituted or unsubstituted alkyl; and X' is O or NH (provided that when R' is unsubstituted phenyl, $R^{2'}$, $R^{3'}$ and $R^{4'}$ are not hydrogen at the same time); or a salt or solvate thereof. The auxin biosynthesis inhibitor of the embodiment has an auxin biosynthesis inhibitory activity equal to or more than that of L-AOPP and high stability.

Specific examples of the preferable embodiment include an auxin biosynthesis inhibitor containing a compound represented by general formula (I') where $R^{1'}$ is phenyl, chlorophenyl, bromophenyl, biphenyl, phenoxyphenyl, 4-chloro-3-methylphenyl, 4-chloro-2-methylphenyl, dichlorophenyl, 6-methoxy-2-naphthyl, naphthyl or quinolinyl; $R^{2'}$ is hydrogen or $C_{1-6}$ alkyl; $R^{3'}$ and $R^{4'}$, which are the same or different, each are hydrogen, acetyl or benzoyl or $R^{3'}$ and $R^{4'}$ together form propan-2-ylidene or, together with a nitrogen atom to which $R^{3'}$ and $R^{4'}$ are bound, form phthalimide or succinimide; $R^{5'}$ is hydrogen or methyl; and X' is O or NH (provided that when $R^{1'}$ is unsubstituted phenyl, $R^{2'}$, $R^{3'}$ and $R^{4'}$ are not hydrogen at the same time); or a salt or solvate thereof.

A further preferable embodiment of the present invention is directed to an auxin biosynthesis inhibitor containing a compound represented by general formula (I') where $R^{1'}$ is a substituted or unsubstituted aryl group or a substituted or unsubstituted heteroaryl group; $R^{2'}$ is a substituted or unsubstituted alkyl group; $R^{3'}$ is hydrogen and $R^{4'}$ is a substituted or unsubstituted acyl group, or $R^{3'}$ and $R^{4'}$ together form a substituted or unsubstituted alkylidene group or, together with a nitrogen atom to which $R^{3'}$ and $R^{4'}$ are bound, form a substituted or unsubstituted cyclic imide group; $R^{5'}$ is hydrogen; and X' is O or NH; or a salt or solvate thereof. The auxin biosynthesis inhibitor of the embodiment has an auxin biosynthesis inhibitory activity equal to or more than that of L-AOPP and extremely high stability.

Specific examples of the further preferable embodiment include an auxin biosynthesis inhibitor containing a compound represented by general formula (I') where $R^{1'}$ is phenyl, chlorophenyl, bromophenyl, biphenyl, phenoxyphenyl, 4-chloro-3-methylphenyl, 4-chloro-2-methylphenyl, dichlorophenyl, 6-methoxy-2-naphthyl, naphthyl or quinolinyl; $R^{2'}$ is $C_{1-6}$ alkyl; $R^{3'}$ is hydrogen and $R^{4'}$ is acetyl or benzoyl or $R^{3'}$ and $R^{4'}$ together form propan-2-ylidene or, together with a nitrogen atom to which $R^{3'}$ and $R^{4'}$ are bound, form phthalimide or succinimide; $R^{5'}$ is hydrogen; and X is O or NH; or a salt or solvate thereof.

The particularly preferable embodiment of the present invention is directed to an auxin biosynthesis inhibitor containing a compound represented by general formula (I') where $R^{1'}$ is substituted aryl group or a substituted or unsubstituted heteroaryl group; $R^{2'}$ is a substituted or unsubstituted alkyl group; $R^{3'}$ is hydrogen and $R^{4'}$ is a substituted or unsubstituted acyl group, or $R^{3'}$ and $R^{4'}$ together form a substituted or unsubstituted alkylidene group or, together with a nitrogen atom to which $R^{3'}$ and $R^{4'}$ are bound, form a substituted or unsubstituted cyclic imide group; $R^{5'}$ is hydrogen; and X' is O; or a salt or solvate thereof. The auxin biosynthesis inhibitor of the embodiment has an auxin biosynthesis inhibitory activity superior to that of L-AOPP and extremely high stability.

Specific examples of the particularly preferable embodiment include an auxin biosynthesis inhibitor containing a compound represented by general formula (I') where $R^1$ is chlorophenyl, bromophenyl, biphenyl, phenoxyphenyl, 4-chloro-3-methylphenyl, 4-chloro-2-methylphenyl, dichlorophenyl, 6-methoxy-2-naphthyl, naphthyl or quinolinyl; $R^{2'}$ is $C_{1-6}$ alkyl; $R^{3'}$ is hydrogen and $R^{4'}$ is acetyl or benzoyl or $R^{3'}$ and $R^{4'}$ together form a substituted or unsubstituted propan-2-ylidene or, together with a nitrogen atom to which $R^{3'}$ and $R^{4'}$ are bound, form phthalimide or succinimide; $R^{5'}$ is hydrogen; and X' is O; or a salt or solvate thereof.

3. Tryptophan Aminotransferase Inhibitor

The present invention further relates to a tryptophan aminotransferase inhibitor comprising a compound represented by general formula (I"):

Formula 8

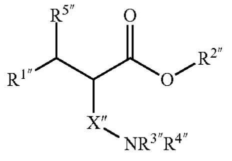

(I")

wherein, $R^{1''}$ to $R^{5''}$ and X" are the same as defined below, or a salt, solvate or a prodrug thereof.

In general formula (I"), $R^{1''}$ is a substituted or unsubstituted aryl group (provided that unsubstituted phenyl is excluded), a substituted or unsubstituted heteroaryl group, a substituted or unsubstituted heterocycloalkyl group, a substituted or unsubstituted aryl-fused cycloalkyl group, or a substituted or unsubstituted aryl-fused heterocycloalkyl group. Preferably, $R^{1''}$ is a substituted aryl group or a substituted or unsubstituted heteroaryl group.

$R^{2''}$ to $R^{5''}$ each are hydrogen.

X" is O, NH or $CH_2$. Preferably, X" is O or NH. Particularly preferably, X" is O.

Specific examples of $R^{1''}$ of general formula (I"), and specific examples of substituents that may be substituted for the group of $R^{1''}$ are the same as described with respect to $R^1$ of general formula (I).

Specific examples of the salt and solvate of a compound represented by general formula (I") are the same as described with respect to the salt and solvate of a compound represented by general formula (I).

Examples of a prodrug of a compound represented by general formula (I") include a prodrug in which the carboxyl group ($COOR^{2''}$) and amino group ($NR^{3''}R^{4''}$) in general formula (I") are protected with protecting groups, which are to be converted to a free carboxylic acid and free amine, respectively in a plant.

Examples of the carboxyl group protected include an ester, a thioester, an amide, and a nitrile. Examples thereof include a $C_{1-6}$ alkyl ester, a $C_{1-4}$ alkyl ester, a $C_{1-6}$ alkylthio ester, a $C_{1-4}$ alkylthio ester, a $—CONR^a_2$ ($R^a$ each independently represent e.g., hydrogen, $C_{1-6}$ alkyl, $C_{1-3}$ alkyl).

Examples of the amino group protected include an amide, an imide and an imine. Examples thereof include —NHCOR$^b$ (R$^b$ is e.g., $C_{1-3}$ alkyl (preferably methyl), aryl (preferably phenyl)), a cyclic imide (preferably phthalimide, succinimide), —N═CR$^c_2$ (R$^c$ each independently represent e.g., $C_{1-3}$ alkyl).

Either one or both of the carboxyl group and amino group may be protected.

An embodiment of the present invention is directed to a tryptophan aminotransferase inhibitor containing a compound represented by general formula (I") where $R^{1"}$ is substituted aryl group or a substituted or unsubstituted heteroaryl group; $R^{2"}$ to $R^{5"}$ each are hydrogen; and X" is O, NH or $CH_2$ (preferably, X" is O); or a salt, solvate or a prodrug thereof.

Examples of the embodiment include a tryptophan aminotransferase inhibitor containing a compound represented by general formula (I") where $R^{1"}$ is chlorophenyl, bromophenyl, biphenyl, phenoxyphenyl, 4-chloro-3-methylphenyl, 4-chloro-2-methylphenyl, dichlorophenyl, 6-methoxy-2-naphthyl, naphthyl or quinolinyl; $R^{2"}$ to $R^{5"}$ each are hydrogen; and X" is O, NH or $CH_2$ (preferably, X" is O); or a salt, solvate or a prodrug thereof. The tryptophan aminotransferase inhibitor of the embodiment has an enzyme inhibitory activity equal to or more than that of L-AOPP.

Preferable examples of the embodiment include tryptophan aminotransferase inhibitor containing a compound represented by general formula (I") where $R^{1"}$ is 4-chlorophenyl, 3-chlorophenyl, biphenyl, 4-chloro-3-methylphenyl or naphthyl; $R^{2"}$ to $R^{5"}$ each are hydrogen; and X" is O; or a salt, solvate or a prodrug thereof. The tryptophan aminotransferase inhibitor of the embodiment has enzyme inhibitory activity superior to that of L-AOPP.

Preferable examples of the embodiment include a tryptophan aminotransferase inhibitor containing a compound represented by general formula (I") where $R^{1"}$ is bromophenyl, biphenyl, phenoxyphenyl, 4-chloro-3-methylphenyl, 6-methoxy-2-naphthyl, naphthyl or quinolinyl; $R^{2"}$ to $R^{5"}$ each are hydrogen; and X" is O; or a salt, solvate or a prodrug thereof. The tryptophan aminotransferase inhibitor of the embodiment has enzyme inhibitory activity equal to or more than that of L-AOPP and further reduced in side effect (PAL inhibitory activity).

Particularly preferable examples of the embodiment include a tryptophan aminotransferase inhibitor containing a compound represented by general formula (I") where $R^{1"}$ is biphenyl, 4-chloro-3-methylphenyl or naphthyl; $R^{2"}$ to $R^{5"}$ each are hydrogen; and X" is O; or a salt, solvate or a prodrug thereof. The tryptophan aminotransferase inhibitor of the embodiment has enzyme inhibitory activity superior to that of L-AOPP and further reduced in side effect (PAL inhibitory activity).

4. Use

The compound of the present invention can be used for inhibiting biosynthesis of auxin, inhibiting tryptophan aminotransferase in vivo (in a plant) and in vitro, and regulating growth of a plant. In inhibiting tryptophan aminotransferase in vitro, an inhibitor, which is not in the form of a prodrug, is preferably used.

The type of plant is not particularly limited as long as the plant biologically synthesizes auxin and as long as the plant has tryptophan aminotransferase.

A method for applying the compound of the present invention to a plant is not particularly limited as long as the method allows the compound to be in contact with the plant. Examples thereof include spraying, dusting, atomizing, soaking and spreading.

The phrase "regulating growth of a plant" refers to exerting some influence on plant growth and include both a promotive effect and an inhibitory effect. Owing to these effects, the compound of the present invention can be used as e.g., a herbicide, a plant growth regulator and a flower keeping agent (freshness-keeping agent).

Now, the present invention will be described in more detail by use of Examples; however, the technical scope of the present invention is not limited to these.

1. Synthesis Examples

Compounds were synthesized in accordance with FIG. 2-2.

Synthesis of KOK1158 (Step 1)

Formula 9

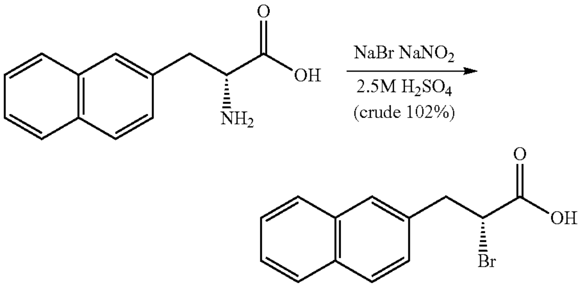

KOK-1158

The titled compound was synthesized by use of a method described in J. Org. Chem. 2006, 71, 3332-3334. 3-(2-Naphthyl)-D-alanine (5.0 g, 23.2 mmol) and sodium bromide (9.7 g, 81.3 mmol) were suspended in 2.5 M sulfuric acid (30 ml) and stirred at 0° C. To the mixture, an aqueous sodium nitrite (2.0 g, 29.0 mmol) solution (10 ml) was added dropwise. After the mixture was stirred at 0° C. for one hour, the temperature of the mixture was returned to room temperature and a reaction was performed for 6 hours. The reaction solution was extracted with ethyl acetate and washed with a saturated aqueous sodium chloride solution. The resultant organic layer was dried over anhydrous sodium sulfate. This was filtered and concentrated under reduced pressure and the residue was purified by silica gel column chromatography (ethyl acetate: acetic acid=100:1) to obtain the titled compound (red-brown oily substance: 6.6 g, crude yield 102%) containing impurities.

$^1$H-NMR ($CDCl_3$, 270 MHz) δ ppm: 3.40 (1H, dd, J=14.2, 7.3 Hz), 3.63 (1H, dd, J=14.2, 8.2 Hz), 4.52 (1H, dd, J=8.2, 7.3 Hz), 7.33 (1H, dd, J=8.6, 1.7 Hz), 7.40-7.51 (2H, m), 7.69 (1H, s), 7.71-7.86 (3H, m).

Synthesis of KOK1164 (Step 2)

Formula 10

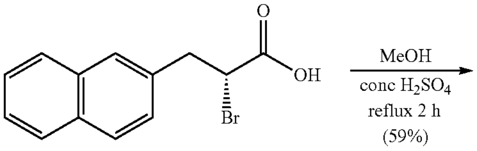

KOK-1158

-continued

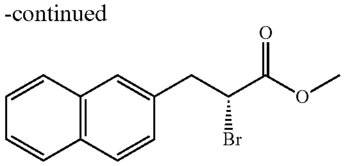

KOK-1164

KOK1158 (6.6 g, 23.6 mmol) obtained in Step 1 was dissolved in methanol (50 ml). To this, concentrated sulfuric acid (0.5 ml) was added and the mixture was refluxed for 2 hours. The reaction solution was concentrated under reduced pressure and the residue was purified by silica gel column chromatography (hexane:ethyl acetate=10:1) to obtain the titled compound (yellow oily substance: 4.1 g, 59%).

$^1$H-NMR ($CDCl_3$, 270 MHz) δ ppm: 3.40 (1H, dd, J=14.3, 7.3 Hz), 3.63 (1H, dd, J=14.3, 8.6 Hz), 3.71 (3H, s), 4.50 (1H, dd, J=8.6, 7.3 Hz), 7.32 (1H, dd, J=8.6, 1.6 Hz), 7.40-7.51 (2H, m), 7.67 (1H, s), 7.72-7.84 (3H, m).

Synthesis of KOK1165 (Step 3)

Formula 11

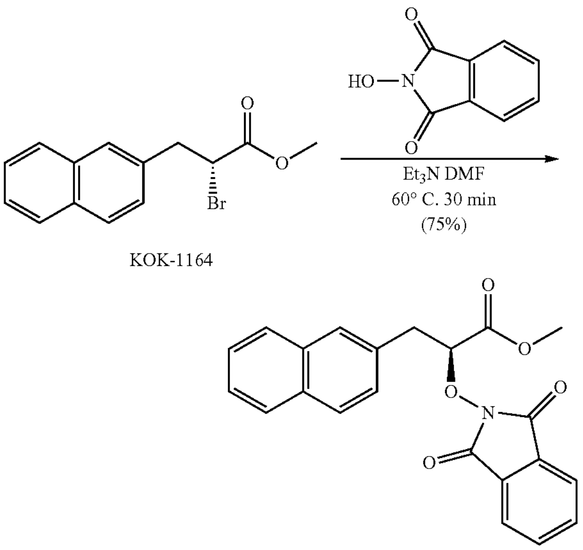

KOK-1164

KOK-1165

N-hydroxyphthalimide (2.5 g, 15.4 mmol) and triethylamine (2.1 ml, 15.4 mmol) were dissolved in N,N-dimethylformamide (10 ml) and stirred at 60° C. To this, an N,N-dimethylformamide solution (5 ml) containing KOK1164 (6.6 g, 23.6 mmol) obtained in Step 2 was added dropwise and stirred at 60° C. for 30 minutes. To the reaction solution, water was added and the mixture was extracted three times with ethyl acetate, washed three times with water and then washed with a saturated aqueous sodium chloride solution. The resultant organic layer was dried over anhydrous sodium sulfate, filtered and concentrated under reduced pressure. Thereafter, the residue was purified by silica gel column chromatography (hexane:ethyl acetate=1:1) to obtain the titled compound (light yellow oily substance: 3.9 g, 75%).

$^1$H-NMR ($CDCl_3$, 270 MHz) δ ppm: 3.41-3.60 (2H, m), 3.72 (3H, s), 5.11 (1H, t, J=6.9 Hz), 7.38-7.50 (3H, m), 7.65-7.83 (8H, m).

Synthesis of KOK1168 (Step 4)

Formula 12

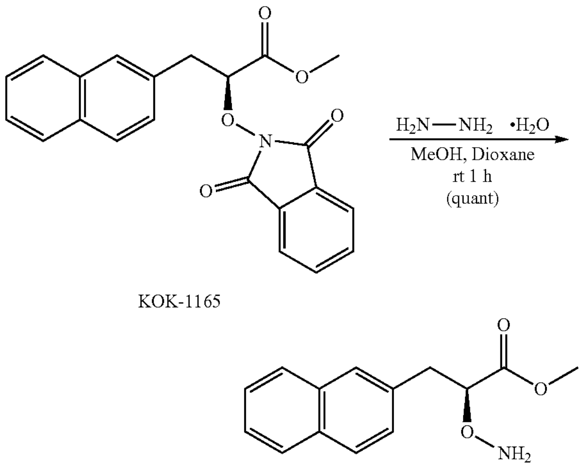

KOK-1165

KOK-1168

KOK1165 (1.3 g, 3.5 mmol) obtained in Step 3 was dissolved in methanol:1,4-dioxane (1:1.8 ml). To the mixture, hydrazine monohydrate (0.2 g, 4.2 mmol) was added and stirred at room temperature for one hour. A saturated aqueous sodium hydrogen carbonate solution (4 ml) was added and concentrated under reduced pressure. To the reaction solution, water was added and the mixture was extracted three times with ethyl acetate, washed with a saturated aqueous sodium chloride solution. The resultant organic layer was dried over anhydrous sodium sulfate, filtered and concentrated under reduced pressure. Thereafter, the residue was purified by silica gel column chromatography (hexane:ethyl acetate=2:1) to obtain the titled compound (colorless oily substance: 0.8 g, 100%).

$^1$H-NMR ($CDCl_3$, 270 MHz) δ ppm: 3.12 (1H, dd, J=14.5, 8.6 Hz), 3.20 (1H, dd, J=14.5, 4.6 Hz), 3.75 (3H, s), 4.51 (1H, dd, J=8.6, 4.6 Hz), 5.67 (2H, s), 7.36 (1H, dd, J=8.2, 1.7 Hz), 7.39-7.50 (2H, m), 7.66 (1H, s), 7.72-7.84 (3H, m).

Synthesis of KOK1169 (Step 5)

Formula 13

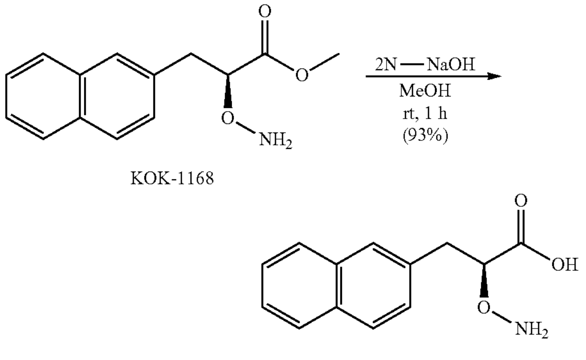

KOK-1168

KOK-1169

KOK1168 (448 mg, 1.81 mmol) obtained in Step 4 was dissolved in methanol (5 ml). To this, a 2N aqueous sodium hydroxide solution (3.6 ml) was added and stirred at room temperature for one hour. To this, 2N hydrochloric acid was added to adjust pH at 4 and concentrated under reduced pressure. Thereafter, the obtained solid substance was suspended in water, filtered off and dried under reduced pressure to obtain the titled compound (white crystal: 391 mg, 93%).

$^1$H-NMR (DMSO-$d_6$, 270 MHz) δ ppm: 3.01 (1H, dd, J=14.5, 8.2 Hz), 3.10 (1H, dd, J=14.5, 4.9 Hz), 4.28 (1H, dd, J=8.2, 5.0 Hz), 7.35-7.52 (3H, m), 7.73 (1H, s), 7.77-7.90 (3H, m), 8.35 (2H, brs).

Synthesis of KOK2015 (Step 6)

Formula 14

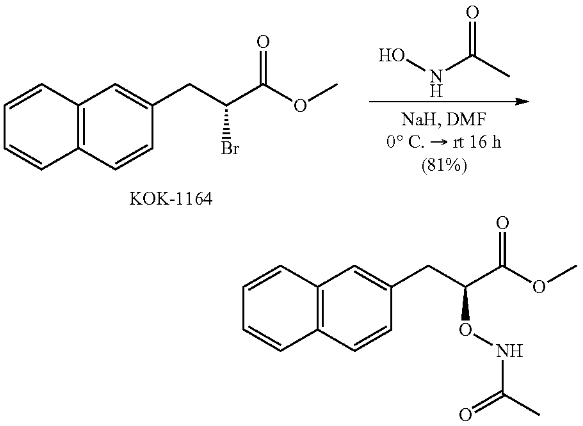

KOK-1164

KOK-2015

Acetohydroxamic acid (31 mg, 0.41 mmol) was dissolved in N,N-dimethylformamide (3 ml). To this, sodium hydride (60%) (16 mg, 0.41 mmol) was added under ice cooling and stirred for 20 minutes. To the mixture, an N,N-dimethylformamide (3 ml) solution containing KOK1164 (100 mg, 0.34 mmol) obtained in Step 2 was added dropwise and stirred at room temperature for 16 hours. To the mixture, water was added and the mixture was extracted three times with ethyl acetate, washed three times with water and then washed with a saturated aqueous sodium chloride solution. The organic layer was dried over anhydrous sodium sulfate. This was filtered and concentrated under reduced pressure. Thereafter, the residue was purified by silica gel column chromatography (hexane:ethyl acetate=1:1) to obtain the titled compound (colorless oily substance: 79 mg, 81%).

$^1$H-NMR (DMSO-$d_6$, 270 MHz) δ ppm: 1.72 (3H, s), 3.21 (2H, d, J=6.3 Hz), 3.61 (3H, s), 4.71 (1H, t, J=6.3 Hz), 7.34-7.54 (3H, m), 7.73-7.92 (4H, m), 11.12 (1H, s).

Synthesis of KOK2016

Formula 15

KOK-2016

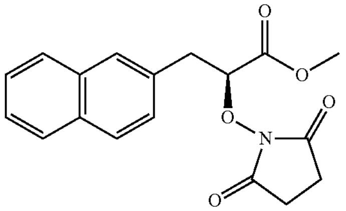

The titled compound was synthesized from compound KOK1164 in the same conditions as in Step 3.

$^1$H-NMR ($CDCl_3$, 270 MHz) δ ppm: 2.55 (4H, s), 3.45 (2H, d, J=6.9 Hz), 3.71 (3H, s), 5.06 (1H, t, J=6.9 Hz), 7.36-7.50 (3H, m), 7.68-7.83 (4H, m). White crystal.

Synthesis of KOK2011

Formula 16

KOK-2011

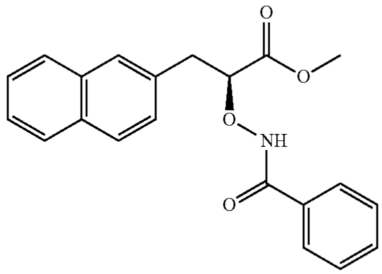

The titled compound was synthesized from compound KOK1164 in the same conditions as in Step 6.

$^1$H-NMR ($CDCl_3$, 270 MHz) δ ppm: 3.39 (1H, dd, J=14.8, 6.6 Hz), 3.49 (1H, dd, J=14.8, 5.3 Hz), 3.71 (3H, s), 5.01 (1H, dd, J=6.9, 5.3 Hz), 7.32-7.54 (6H, m), 7.62-7.72 (2H, m), 7.72-7.85 (4H, m), 9.17 (1H, s). White crystal.

Synthesis of KOK1168 (Step 7)

Formula 17

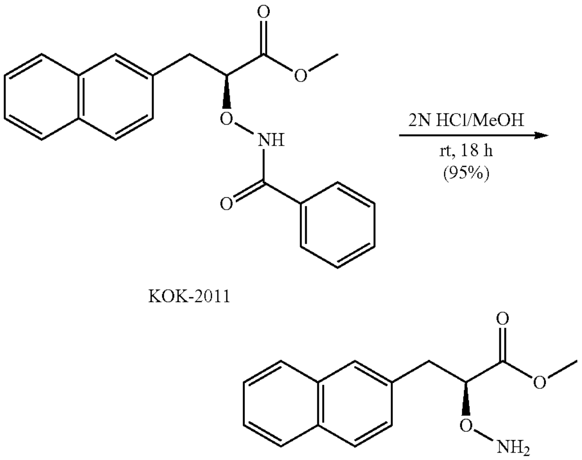

KOK-2011

KOK-1168

To KOK2011 (2.00 g, 5.72 mmol), 2M (2N) hydrochloric acid.methanol (10 ml) was added and suspended. The mixture was stirred at room temperature for 18 hours. The reaction solution was concentrated under reduced pressure. To the residue, water and ethyl acetate were added. The reaction solution was adjusted with a 2N aqueous sodium hydroxide solution at pH4, extracted three times with ethyl acetate and dried over anhydrous sodium sulfate. This was filtered and concentrated under reduced pressure and then the residue was purified by silica gel column chromatography (hexane:ethyl acetate=2:1) to obtain the titled compound (colorless oily substance: 1.33 g, 95%).

$^1$H-NMR ($CDCl_3$, 270 MHz) δ ppm: 3.12 (1H, dd, J=14.5, 8.6 Hz), 3.20 (1H, dd, J=14.5, 4.6 Hz), 3.75 (3H, s), 4.51 (1H, dd, J=8.6, 4.6 Hz), 5.67 (2H, s), 7.36 (1H, dd, J=8.2, 1.7 Hz), 7.39-7.50 (2H, m), 7.66 (1H, s), 7.72-7.84 (3H, m).

Synthesis of KOK1198 (Step 8)

Formula 18

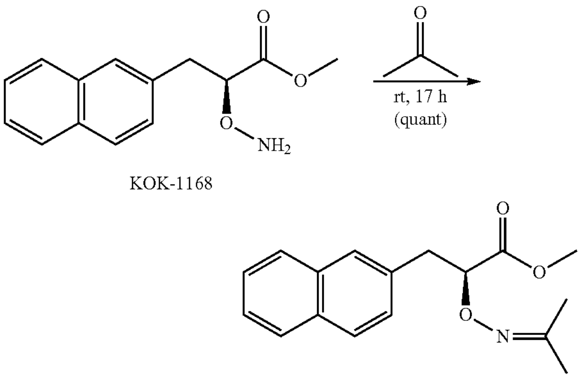

KOK-1168

KOK-1198

To KOK1168 (60 mg, 0.25 mmol) obtained in Step 4 or 7, acetone (3 ml) was added and stirred at room temperature for 17 hours. The mixture was concentrated under reduced pressure to obtain the titled compound (white crystal: 70 mg, 100%).

$^1$H-NMR ($CDCl_3$, 270 MHz) δ ppm: 1.82 (3H, s), 1.87 (3H, s), 3.27 (2H, d, J=6.3 Hz), 3.70 (3H, s), 4.84 (1H, t, J=6.3 Hz), 7.33-7.50 (3H, m), 7.68 (1H, s), 7.71-7.84 (3H, m).

Figures 2, 3:
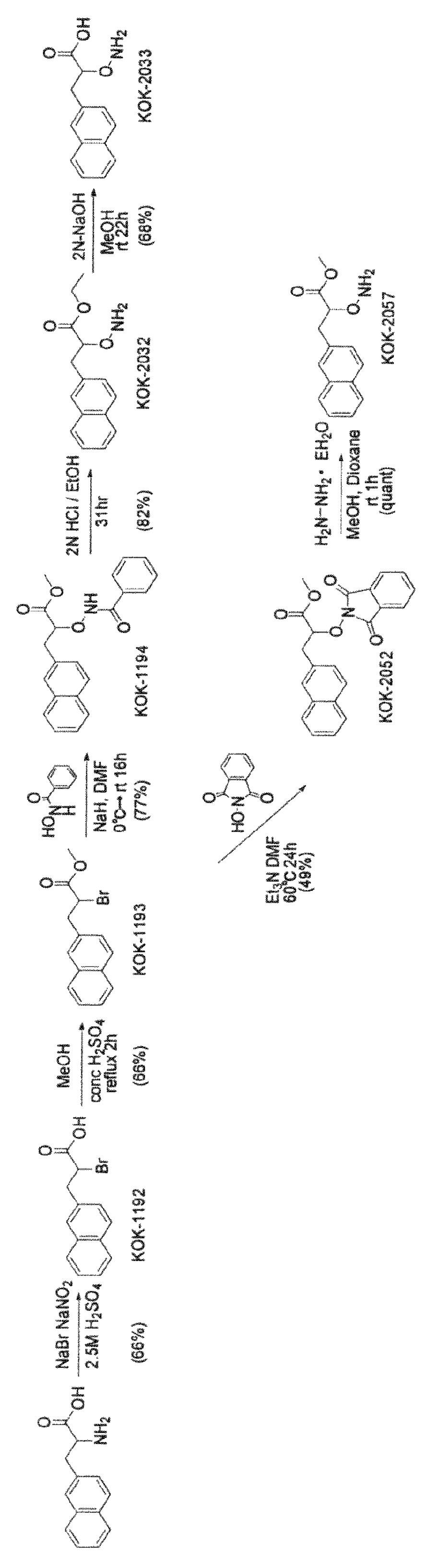

Compounds were synthesized in accordance with FIG. 2-3. KOK1192 was synthesized in the same conditions as used in Step 1, KOK1193 in Step 2, KOK1194 in Step 6, KOK2032 in Step 7, KOK2033 in Step 5, KOK2052 in Step 3 and KOK2057 in Step 4.

KOK1193

Formula 19

KOK-1193

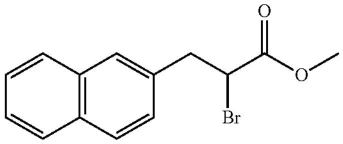

$^1$H-NMR ($CDCl_3$, 270 MHz) δ ppm: 3.40 (1H, dd, J=14.3, 7.3 Hz), 3.63 (1H, dd, J=14.3, 8.6 Hz), 3.71 (3H, s), 4.50 (1H, dd, J=8.6, 7.3 Hz), 7.32 (1H, dd, J=8.6, 1.6 Hz), 7.40-7.51 (2H, m), 7.67 (1H, s), 7.72-7.84 (3H, m). Yellow oily substance.

KOK1194

Formula 20

KOK-1194

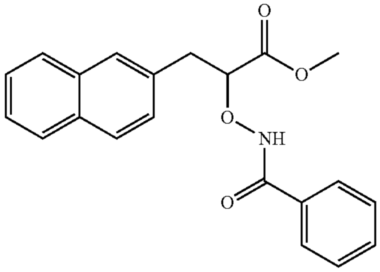

$^1$H-NMR ($CDCl_3$, 270 MHz) δ ppm: 3.39 (1H, dd, J=14.8, 6.6 Hz), 3.49 (1H, dd, J=14.8, 5.3 Hz), 3.71 (3H, s), 5.01 (1H, dd, J=6.9, 5.3 Hz), 7.32-7.54 (6H, m), 7.62-7.72 (2H, m), 7.72-7.85 (4H, m), 9.17 (1H, s). White solid substance.

KOK2032

Formula 21

KOK-2032

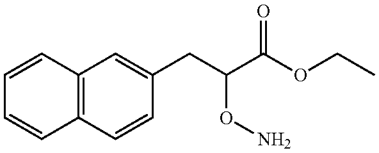

$^1$H-NMR ($CDCl_3$, 270 MHz) δ ppm: 1.23 (1H, t, J=7.3 Hz), 3.07-3.25 (2H, m), 4.21 (2H, q, J=7.3 Hz), 4.49 (1H, dd, J=8.6, 4.6 Hz), 5.68 (2H, brs), 7.32-7.50 (3H, m), 7.67 (1H, s), 7.72-7.84 (3H, m). Light yellow oily substance.

KOK2033

Formula 22

KOK-2033

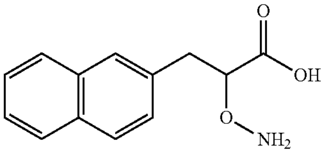

$^1$H-NMR (DMSO-$d_6$, 270 MHz) δ ppm: 3.01 (1H, dd, J=14.5, 8.2 Hz), 3.10 (1H, dd, J=14.5, 4.9 Hz), 4.28 (1H, dd, J=8.2, 5.0 Hz), 7.35-7.52 (3H, m), 7.73 (1H, s), 7.77-7.90 (3H, m), 8.35 (2H, brs). White crystal.

KOK2052

Formula 23

KOK-2052

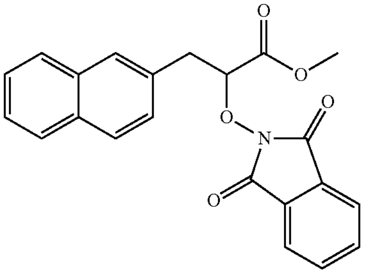

$^1$H-NMR ($CDCl_3$, 270 MHz) δ ppm: 3.41-3.60 (2H, m), 3.72 (3H, s), 5.11 (1H, t, J=6.9 Hz), 7.38-7.50 (3H, m), 7.65-7.83 (8H, m). Brown sticky oily substance.

KOK2057

Formula 24

KOK-2057

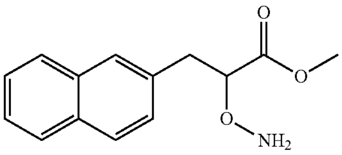

$^1$H-NMR ($CDCl_3$, 270 MHz) δ ppm: 3.12 (1H, dd, J=14.5, 8.6 Hz), 3.20 (1H, dd, J=14.5, 4.6 Hz), 3.75 (3H, s), 4.51 (1H, dd, J=8.6, 4.6 Hz), 5.67 (2H, s), 7.36 (1H, dd, J=8.2, 1.7 Hz), 7.39-7.50 (2H, m), 7.66 (1H, s), 7.72-7.84 (3H, m). Colorless oily substance.

Figures 2, 3, 4:
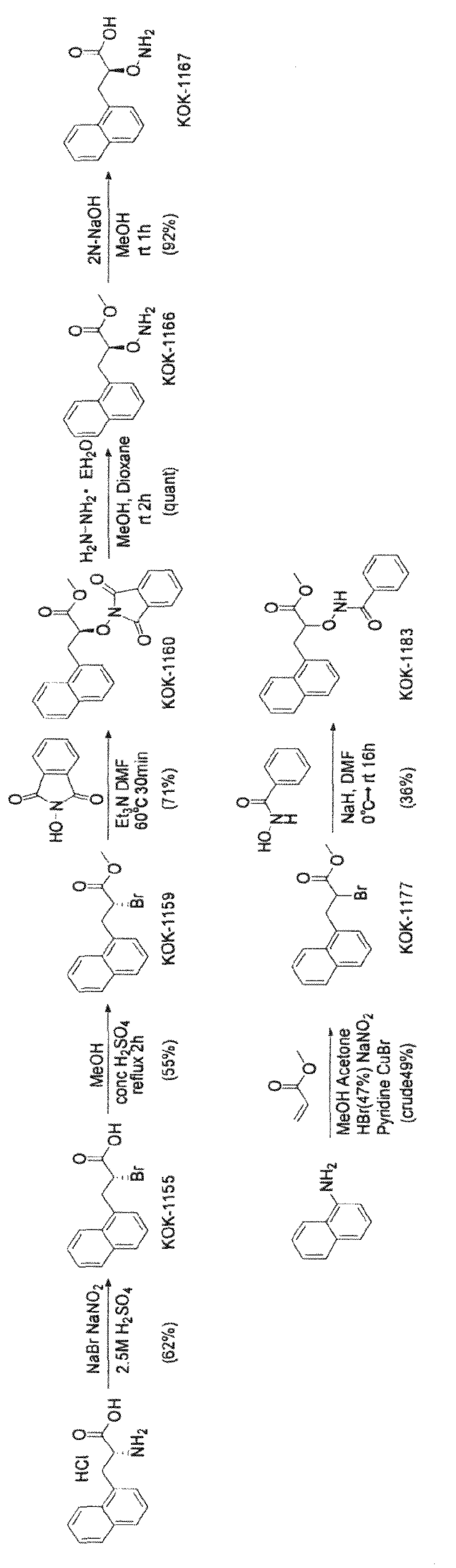

Compounds were synthesized in accordance with FIG. 2-4. KOK1155 was synthesized in the same conditions as used in Step 1, KOK1159 in Step 2, KOK1160 in Step 3, KOK1166 in Step 4, KOK1167 in Step 5 and KOK1183 in Step 6. KOK1177 was synthesized in accordance with Step 9 shown below.

KOK1160

Formula 25

KOK-1160

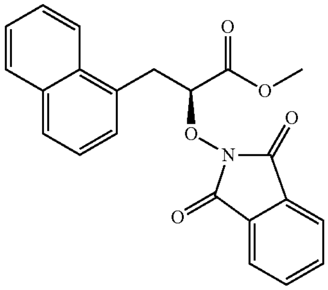

$^1$H-NMR ($CDCl_3$, 270 MHz) δ ppm: 3.67 (3H, s), 3.75 (1H, dd, J=14.5, 8.2 Hz), 3.92 (1H, dd, J=14.5, 6.3 Hz), 5.11 (1H, dd, J=8.2, 6.3 Hz), 7.36-7.63 (4H, m), 7.68-7.90 (6H, m), 8.15 (1H, d, J=8.6 Hz). Light yellow solid substance.

KOK1166

Formula 26

KOK-1166

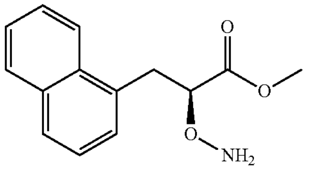

$^1$H-NMR ($CDCl_3$, 270 MHz) δ ppm: 3.37 (1H, dd, J=14.5, 8.9 Hz), 3.53 (1H, dd, J=14.5, 4.6 Hz), 3.74 (3H, s), 4.57 (1H, dd, J=8.9, 4.6 Hz), 5.64 (2H, s), 7.33-7.59 (4H, m), 7.72-7.80 (1H, m), 7.82-7.90 (1H, m), 8.07 (1H, d, J=8.2 Hz). Light yellow oily substance.

KOK1167

Formula 27

KOK-1167

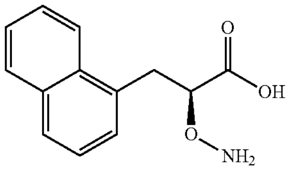

$^1$H-NMR (DMSO-$d_6$, 270 MHz) 5 ppm: 3.28 (1H, dd, J=14.2, 8.2 Hz), 3.41 (1H, dd, J=14.2, 4.6 Hz), 4.29 (1H, dd, J=8.2, 4.6 Hz), 7.34-7.47 (2H, m), 7.47-7.62 (2H, m), 7.81 (1H, d, J=7.6 Hz), 7.93 (1H, d, J=7.6 Hz), 8.08 (1H, d, J=8.6 Hz), 8.42 (2H, brs). White crystal.

Synthesis of KOK1177 (Step 9)

Formula 28

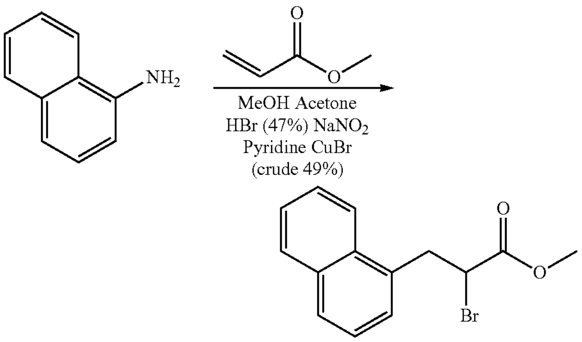

KOK-1177

The titled compound was synthesized in accordance with a method described in WO2010/041538. 1-Naphthylamine (5.00 g, 34.92 mmol) was dissolved in methanol (50 ml) and acetone (50 ml) and cooled to 10° C. To this, hydrobromic acid (47 mass %, 12.26 g) (hydrogen bromide: 71.23 mmol) was added. The reaction solution was cooled to 2° C. While maintaining the temperature of the reaction solution not to exceed 5° C., an aqueous solution (6 ml) containing sodium nitrite (2.75 g, 39.81 mmol) was added dropwise. The resultant mixture was stirred at 2° C. for 20 minutes to synthesize a diazonium salt. In a different vessel, methyl acrylate (6.01 g, 69.84 mmol), pyridine (8.29 ml, 104.76 mmol) and copper bromide (I) (0.63 g, 4.40 mmol) were charged and stirred at 47° C. To the mixture solution, a solution containing the diazonium salt was added dropwise over 30 minutes. Thereafter, the mixture solution was further stirred at 47° C. for 2 hours and then the solvent was evaporated. To the obtained residue, ammonia water (28 mass %) was added. The solution was extracted three times with ethyl acetate, washed with water and dried over anhydrous sodium sulfate. This was filtered and concentrated under reduced pressure. Thereafter, the residue was purified by silica gel column chromatography (hexane:ethyl acetate=10:1) to obtain the titled compound (black oily substance: 4.97 g, crude yield 49%) containing impurities.

KOK1183

Formula 29

KOK-1183

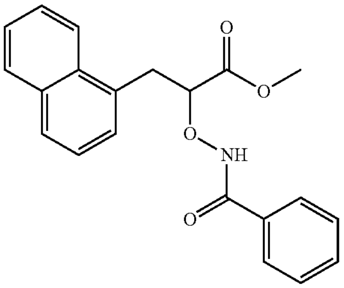

$^1$H-NMR ($CDCl_3$, 270 MHz) δ ppm: 3.58 (3H, s), 3.62-3.72 (2H, m), 5.06 (1H, t, J=6.2 Hz), 7.28-7.58 (7H, m), 7.58-7.70 (2H, m), 7.75 (1H, d, J=7.8 Hz), 7.83 (1H, d, J=7.8 Hz), 7.10 (1H, d, J=8.1 Hz), 9.38 (1H, s). Yellow ocher crystal.

Compounds were synthesized in accordance with FIG. 2-5. KOK2029 was synthesized in the same conditions as used in Step 3, KOK2030 in Step 4 and KOK2031 in Step 5. KOK2019, KOK2025 and KOK2028 were synthesized in accordance with Steps 10, 11 and 12 shown below, respectively.

Synthesis of KOK2019 (Step 10)

Formula 30

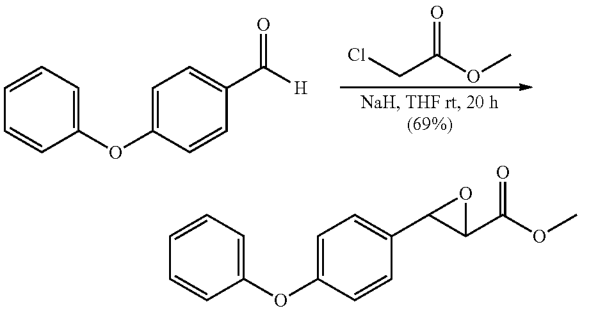

KOK-2019

To sodium hydride (60%) (303 mg, 7.57 mmol), tetrahydrofuran (5 ml) was added and stirred. To this, a mixture solution of 4-phenoxy benzaldehyde (1.00 g, 5.05 mmol), methyl chloroacetate (657 mg, 6.05 mmol) and tetrahydrofuran (10 ml) was added dropwise and stirred at room temperature overnight. The reaction solution was ice-cooled, neutralized with 1M sulfuric acid, extracted three times with dichloromethane, dried over anhydrous sodium sulfate, filtered and concentrated under reduced pressure. Thereafter, the residue was purified by silica gel column chromatography (hexane:ethyl acetate=10:1) to obtain the titled compound (white crystal: 940 mg, 69%).

$^1$H-NMR ($CDCl_3$, 270 MHz) δ ppm: 3.52 (1H, d, J=1.6 Hz), 3.83 (3H, s), 4.08 (1H, d, J=1.6 Hz), 6.94-7.04 (4H, m), 7.08-7.17 (1H, m), 7.20-7.28 (2H, m), 7.28-7.40 (2H, m).

Synthesis of KOK2025 (Step 11)

Formula 31

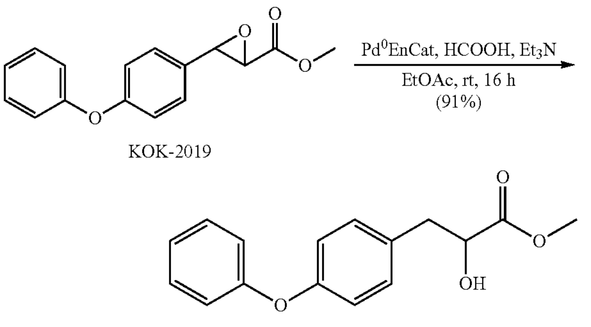

KOK-2019

KOK-2025

The titled compound was synthesized in accordance with a method described in Organic Letters 2003, vol. 5, No. 24, 4665-4668. KOK2019 (940 mg, 3.48 mmol) obtained in Step 10 and Pd$^0$-EnCat® (0.4 mmol/g, 435 mg, 0.17 mmol) were dissolved in ethyl acetate (10 ml). To this, triethyl amine (1.93 ml, 13.91 mmol) and formic acid (0.53 ml, 13.91 mmol) were added. The reaction solution was stirred under an argon atmosphere at room temperature overnight, and then filtered. The filtrate was concentrated under reduced pressure and thereafter the residue was purified by silica gel column chromatography (hexane:ethyl acetate=5:1) to obtain the titled compound (white crystal: 859 mg, 91%).

$^1$H-NMR ($CDCl_3$, 270 MHz) δ ppm: 3.72 (1H, d, J=5.9 Hz), 2.94 (1H, dd, J=14.2, 6.6 Hz), 3.11 (1H, dd, J=14.2, 4.6 Hz), 3.78 (3H, s), 4.38-4.50 (1H, m), 6.88-7.03 (4H, m), 7.03-7.13 (1H, m), 7.13-7.21 (2H, m), 7.27-7.37 (2H, m).

Synthesis of KOK2028 (Step 12)

Formula 32

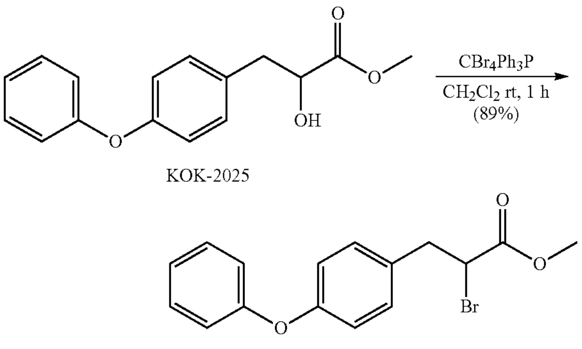

KOK-2025

KOK-2028

KOK2025 (859 mg, 3.16 mmol) obtained in Step 11 and triphenylphosphine (2.482 g, 9.46 mmol) were dissolved in dichloromethane (6 ml). To this, carbon tetrabromide (1.046 g, 4.73 mmol) was added and stirred at room temperature for one hour. To the reaction solution, ice water was added. The reaction solution was extracted three times with dichloromethane. The organic layer was dried over anhydrous sodium sulfate, filtered and concentrated under reduced pressure. The residue was purified by silica gel column chromatography (hexane:ethyl acetate=20:1) to obtain the titled compound (white crystal: 937 mg, 89%).

$^1$H-NMR ($CDCl_3$, 270 MHz) δ ppm: 3.21 (1H, dd, J=14.2, 6.9 Hz), 3.44 (1H, dd, J=14.2, 8.2 Hz), 3.74 (3H, s), 4.37 (1H, dd, J=8.2, 6.9 Hz), 6.88-7.03 (4H, m), 7.06-7.20 (3H, m), 7.27-7.38 (2H, m).

KOK2029

Formula 33

KOK-2029

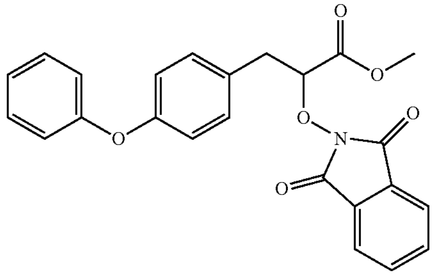

$^1$H-NMR ($CDCl_3$, 270 MHz) δ ppm: 3.23-3.41 (2H, m), 3.74 (3H, s), 4.97 (1H, t, J=6.9 Hz), 6.90-7.02 (4H, m), 7.04-7.13 (1H, m), 7.23-7.36 (4H, m), 7.70-7.86 (2H, m). Colorless sticky oily substance.

KOK2030

Formula 34

KOK-2030

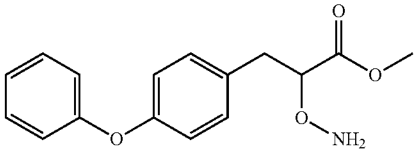

$^1$H-NMR ($CDCl_3$, 270 MHz) δ ppm: 2.88-3.06 (2H, m), 3.75 (3H, s), 4.39 (1H, dd, J=8.2, 5.0 Hz), 5.68 (2H, s), 6.88-7.03 (4H, m), 7.03-7.12 (1H, m), 7.12-7.21 (2H, m), 7.26-7.37 (2H, m). White crystal.

KOK2031

Formula 35

KOK-2031

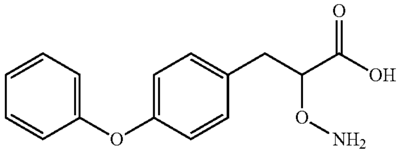

$^1$H-NMR (DMSO-$d_6$, 270 MHz) δ ppm: 2.76-2.97 (2H, m), 4.17 (1H, dd, J=8.2, 5.0 Hz), 6.86-7.02 (4H, m), 7.04-7.18 (1H, m), 7.18-7.30 (2H, m), 7.30-7.43 (2H, m), 8.38 (2H, brs). White crystal.

Compounds were synthesized in accordance with FIG. 2-6. KOK2014 was synthesized in the same conditions as used in Step 10, KOK2018 in Step 11, KOK2020 in Step 12, KOK2021 in Step 3, KOK2026 in Step 4 and KOK2027 in Step 5.

KOK2021

Formula 36

KOK-2021

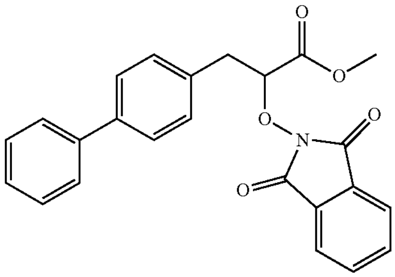

$^1$H-NMR ($CDCl_3$, 270 MHz) 5 ppm: 3.30-3.48 (2H, m), 3.74 (3H, s), 5.05 (1H, t, J=6.9 Hz), 7.26-7.44 (5H, m), 7.48-7.58 (4H, m), 7.65-7.83 (4H, m). Colorless sticky oily substance.

KOK2026

Formula 37

KOK-2026

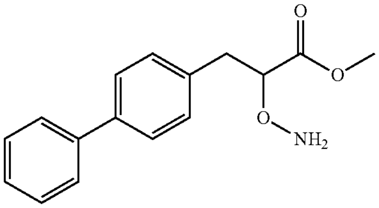

$^1$H-NMR ($CDCl_3$, 270 MHz) δ ppm: 2.92-3.12 (2H, m), 3.75 (3H, s), 4.44 (1H, dd, J=8.5, 4.6 Hz), 5.68 (3H, s), 7.22-7.36 (3H, m), 7.36-7.46 (2H, m), 7.46-7.60 (4H, m). White crystal.

KOK2027

Formula 38

KOK-2027

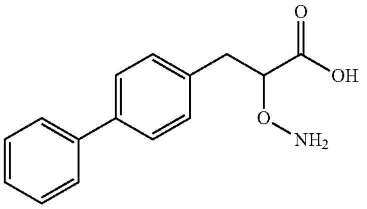

$^1$H-NMR (DMSO-$d_6$, 270 MHz) δ ppm: 2.88 (1H, dd, J=14.2, 8.2 Hz), 2.98 (1H, dd, J=14.2, 4.9 Hz), 4.21 (1H, dd, J=8.2, 4.9 Hz), 7.25-7.39 (3H, m), 7.39-7.50 (2H, m), 7.50-7.68 (4H, m), 8.35 (2H, brs). White crystal.

Compounds were synthesized in accordance with FIG. 2-7. KOK1170 was synthesized in the same conditions as used in Step 1, KOK1171 in Step 2, KOK1174 in Step 3, KOK1175 in Step 4, KOK1176 in Step 5, KOK1184 in Step 9, KOK1185 in Step 3, KOK1186 in Step 4, KOK1187 in Step 5, KOK1173 in Step 9, KOK1178 in Step 3, KOK1179 in Step 4 and KOK1180 in Step 5.

KOK1174

Formula 39

KOK-1174

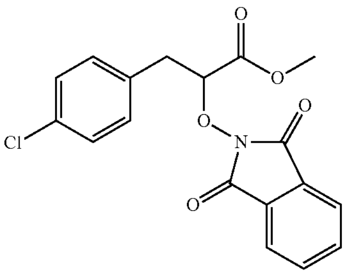

$^1$H-NMR ($CDCl_3$, 270 MHz) δ ppm: 3.22-3.40 (2H, m), 3.74 (3H, s), 4.96 (1H, t, J=6.9 Hz), 7.28 (4H, s), 7.70-7.86 (4H, m). White crystal.

KOK1175

Formula 40

KOK-1175

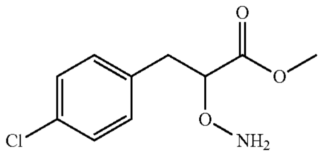

$^1$H-NMR ($CDCl_3$, 270 MHz) δ ppm: 2.87-3.06 (2H, m), 3.75 (3H, s), 4.37 (1H, dd, J=8.2, 4.6 Hz), 5.67 (2H, s), 7.09-7.18 (2H, m), 7.21-7.29 (2H, m). Colorless oily substance.

KOK1176

Formula 41

KOK-1176

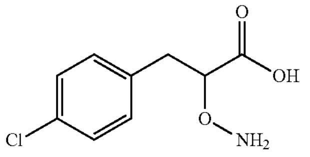

$^1$H-NMR (DMSO-$d_6$, 270 MHz) δ ppm: 2.84 (1H, dd, J=14.2, 8.2 Hz), 2.93 (1H, dd, J=14.2, 5.0 Hz), 4.16 (1H, dd, J=8.2, 5.0 Hz), 7.20-7.36 (4H, m), 8.37 (2H, brs). White crystal.

KOK1185

Formula 42

KOK-1185

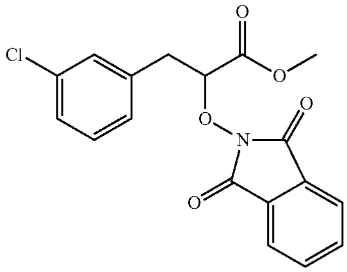

$^1$H-NMR ($CDCl_3$, 270 MHz) δ ppm: 3.28 (1H, dd, J=14.5, 6.6 Hz), 3.35 (1H, dd, J=14.5, 6.9 Hz), 3.75 (3H, s), 4.97 (1H, dd, J=6.9, 6.6 Hz), 7.18-7.26 (3H, m), 7.31-7.36 (1H, m), 7.70-7.86 (4H, m). White crystal.

KOK1186

Formula 43

KOK-1186

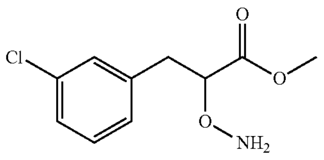

$^1$H-NMR ($CDCl_3$, 270 MHz) δ ppm: 2.93 (1H, dd, J=14.5, 8.6 Hz), 3.02 (1H, dd, J=14.5, 5.0 Hz), 3.76 (3H, s), 4.39 (1H, dd, J=8.6, 5.0 Hz), 5.68 (2H, s), 7.04-7.14 (1H, m), 7.16-7.24 (3H, m). Yellow oily substance.

KOK1187

Formula 44

KOK-1187

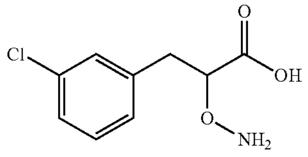

$^1$H-NMR (DMSO-$d_6$, 270 MHz) δ ppm: 2.86 (1H, dd, J=14.5, 5.0 Hz), 2.96 (1H, dd, J=14.5, 8.2 Hz), 4.19 (1H, dd, J=8.2, 5.0 Hz), 7.15-7.34 (4H, m), 8.43 (2H, brs). White crystal.

KOK1178

Formula 45

KOK-1178

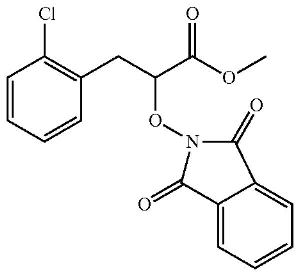

$^1$H-NMR ($CDCl_3$, 270 MHz) δ ppm: 3.42 (1H, dd, J=14.2, 6.9 Hz), 3.52 (1H, dd, J=14.2, 7.6 Hz), 3.75 (3H, s), 5.07 (1H, dd, J=7.6, 6.9 Hz), 7.06-7.27 (2H, m), 7.33-7.44 (2H, m), 7.67-7.85 (4H, m). White crystal.

KOK1179

Formula 46

KOK-1179

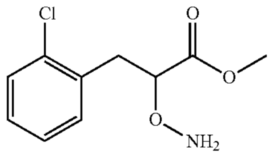

$^1$H-NMR ($CDCl_3$, 270 MHz) δ ppm: 3.09 (1H, dd, J=14.2, 8.9 Hz), 3.21 (1H, dd, J=14.2, 5.0 Hz), 3.75 (3H, s), 4.51 (1H, dd, J=8.9, 5.0 Hz), 5.66 (2H, s), 7.13-7.28 (3H, m), 7.30-7.40 (1H, m). Colorless oily substance.

KOK1180

Formula 47

KOK-1180

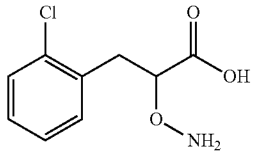

$^1$H-NMR (DMSO-$d_6$, 270 MHz) δ ppm: 2.87 (1H, dd, J=14.2, 8.9 Hz), 3.06 (1H, dd, J=14.2, 5.0 Hz), 4.23 (1H, dd, J=8.9, 5.0 Hz), 7.17-7.46 (4H, m), 8.45 (2H, brs). White crystal.

Compounds were synthesized in accordance with FIG. 2-8. KOK1152 was synthesized in the same conditions as used in Step 2, KOK1161 in Step 3, KOK1153 in Step 2, KOK1172 in Step 3, KOK1151 in Step 2, KOK1157 in Step 6, and KOK1162 in Step 6.

KOK1172

Formula 48

KOK-1172

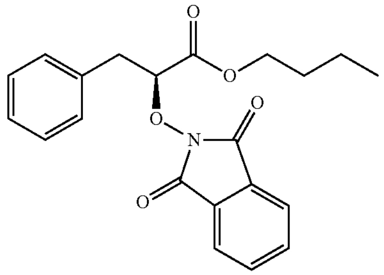

$^1$H-NMR ($CDCl_3$, 270 MHz) δ ppm: 0.85 (3H, t, J=7.3 Hz), 1.15-1.33 (2H, m), 1.45-1.60 (2H, m), 3.24-3.44 (2H, m), 4.10 (2H, t, J=6.5 Hz), 5.00 (1H, t, J=7.3 Hz), 7.18-7.37 (5H, m), 7.67-7.85 (4H, m). Colorless oily substance.

KOK1157

Formula 49

KOK-1157

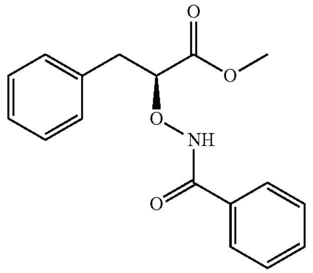

$^1$H-NMR ($CDCl_3$, 270 MHz) δ ppm: 3.23 (1H, dd, J=14.5, 6.6 Hz), 3.32 (1H, dd, J=14.5, 5.3 Hz), 3.72 (3H, s), 4.93 (1H, dd, J=6.6, 5.3 Hz), 7.20-7.55 (8H, m), 7.62-7.71 (2H, m), 7.62-7.71 (2H, m), 9.14 (1H, brs). White crystal.

KOK1162

Formula 50

KOK-1162

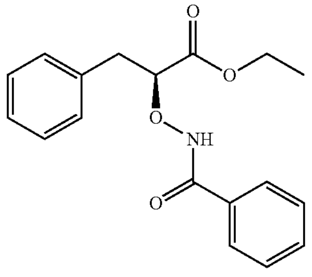

$^1$H-NMR ($CDCl_3$, 270 MHz) δ ppm: 1.15 (3H, t, J=6.9 Hz), 3.23 (2H, d, J=5.6 Hz), 4.11 (2H, q, J=6.9 Hz), 4.91 (1H, t, J=5.6 Hz), 7.12-7.48 (8H, m), 7.60-7.75 (2H, m), 9.63 (1H, s). White crystal.

Compounds were synthesized in accordance with FIG. 2-9. KOK1118 and KOK1141 were synthesized in the same conditions as used in Step 11, KOK1136 and KOK1146 in Step 12, KOK1145 and KOK1148 in Step 6, KOK1149 in Step 4, and KOK1154 in Step 5.

KOK1148

Formula 51

KOK-1148

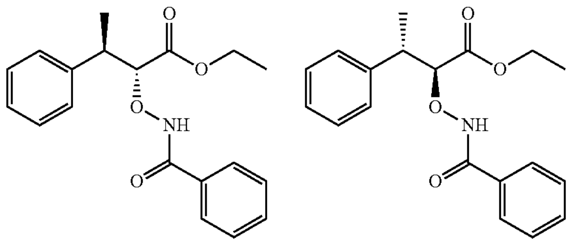

anti type $^1$H-NMR ($CDCl_3$, 270 MHz) δ ppm: 1.18 (3H, t, J=7.3 Hz), 1.59 (3H, d, J=7.3 Hz), 3.35-3.52 (1H, m), 4.03-4.20 (2H, m), 4.82 (1H, d, J=5.1 Hz), 7.15-7.53 (8H, m), 7.60-7.70 (2H, m), 9.31 (1H, s). Colorless oily substance.

KOK1149

Formula 52

KOK-1149

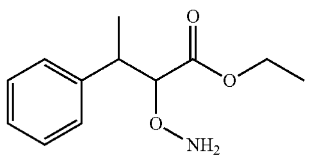

anti type $^1$H-NMR ($CDCl_3$, 270 MHz) δ ppm: 1.23 (3H, t, J=7.3 Hz), 1.31 (3H, d, J=7.3 Hz), 3.06-3.20 (1H, m), 4.10-4.24 (2H, m), 4.29 (1H, d, J=7.3 Hz), 5.57 (2H, brs), 7.15-7.32 (5H, m). Colorless oily substance.

KOK1154

Formula 53

KOK-1154

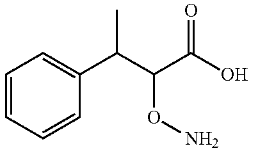

anti type $^1$H-NMR (DMSO-$d_6$, 270 MHz) δ ppm: 1.20 (3H, d, J=7.3 Hz), 2.94-3.08 (1H, m), 4.12 (1H, d, J=7.6 Hz), 7.12-7.32 (5H, m), 8.51 (2H, brs). White crystal.

Compounds were synthesized in accordance with FIG. 2-10. KOK1188 was synthesized in the same conditions as used in Step 9, KOK1190 in Step 6, KOK2022 in Step 7, and KOK2036 in Step 5.

KOK1188

Formula 54

KOK-1188

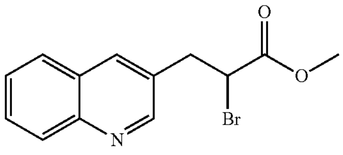

$^1$H-NMR ($CDCl_3$, 270 MHz) δ ppm: 3.45 (1H, dd, J=14.5, 7.6 Hz), 3.66 (1H, dd, J=14.5, 7.9 Hz), 3.75 (3H, s), 4.50 (1H, dd, J=7.9, 7.6 Hz), 7.50-7.60 (1H, m), 7.65-7.75 (1H, m), 7.75-7.85 (1H, m), 7.98-8:05 (1H, m), 8.05-8.14 (1H, m), 8.80 (1H, d, J=2.3 Hz). Brown oily substance.

KOK1190

Formula 55

KOK-1190

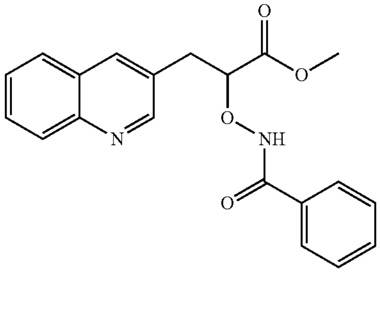

$^1$H-NMR ($CDCl_3$, 270 MHz) δ ppm: 3.40 (1H, dd, J=15.2, 6.6 Hz), 3.51 (1H, dd, J=15.2, 4.6 Hz), 3.74 (3H, s), 5.02 (1H, dd, J=6.6, 4.6 Hz), 7.33-7.44 (2H, m), 7.44-7.58 (2H, m), 7.60-7.75 (3H, m), 7.75-7.86 (1H, m), 8.06 (1H, d, J=8.6 Hz), 8.26 (1H, s), 8.79 (1H, d, J=2.3 Hz), 9.49 (1H, s). White crystal.

KOK2022

Formula 56

KOK-2022

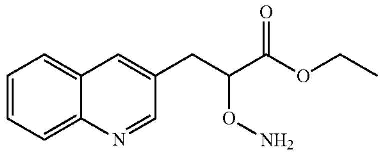

$^1$H-NMR ($CDCl_3$, 270 MHz) δ ppm: 1.25 (3H, t, J=7.3 Hz), 3.10-3.29 (2H, m), 4.23 (2H, q, J=7.3 Hz), 4.46 (1H, dd, J=8.2, 5.0 Hz), 5.72 (2H, brs), 7.48-7.57 (1H, m), 7.62-7.72 (1H, m), 7.72-7.82 (1H, m), 8.01 (1H, d, J=2.0 Hz), 8.08 (1H, d, J=8.6 Hz), 8.80 (1H, d, J=2.0 Hz). Light brown oily substance.

KOK2036

Formula 57

KOK-2036

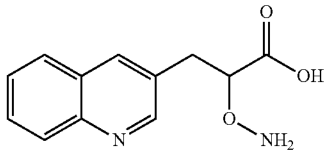

$^1$H-NMR (DMSO-$d_6$, 270 MHz) δ ppm: 3.06 (1H, dd, J=14.6, 8.4 Hz), 3.19 (1H, dd, J=14.6, 4.3 Hz), 4.24 (1H, dd, J=8.4, 4.3 Hz), 7.53-7.63 (1H, m), 7.63-7.75 (1H, m), 7.84-8.02 (2H, m), 8.17 (1H, d, J=2.2 Hz), 8.78 (1H, d, J=2.2 Hz). White crystal.

In accordance with FIG. 2-11, KOK2017 was synthesized in the same conditions as used in Step 6.

KOK2017

Formula 58

KOK-2017

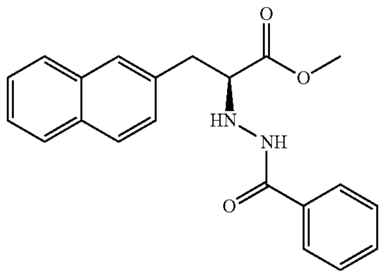

$^1$H-NMR (DMSO-$d_6$, 270 MHz) δ ppm: 3.15 (2H, d, J=6.9 Hz), 3.54 (3H, s), 3.92-4.06 (1H, m), 5.57-5.67 (1H, m), 7.35-7.60 (6H, m), 7.67-7.93 (6H, m), 10.13 (1H, d, J=5.9 Hz). Light yellow sticky oily substance.

Compounds were synthesized in accordance with FIG. 2-12. KOK2043 was synthesized in the same conditions as used in Step 9, KOK2044 in Step 3, KOK2087 in Step 4 and KOK2090 in Step 5.

KOK2043

Formula 59

KOK-2043

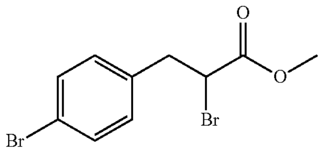

$^1$H-NMR ($CDCl_3$, 270 MHz) δ ppm: 3.19 (1H, dd, J=14.2, 7.1 Hz), 3.42 (1H, dd, J=14.2, 8.2 Hz), 3.73 (3H, s), 4.36 (1H, dd, J=8.2, 7.1 Hz), 7.04-7.13 (2H, m), 7.39-7.48 (2H, m). White crystal.

KOK2044

Formula 60

KOK-2044

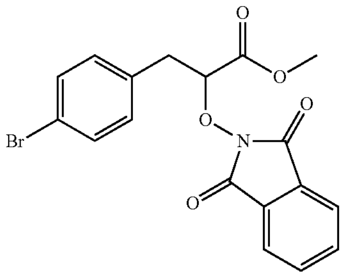

$^1$H-NMR ($CDCl_3$, 270 MHz) 5 ppm: 3.21-3.38 (2H, m), 3.74 (3H, s), 4.96 (1H, t, J=6.9 Hz), 7.18-7.25 (2H, m), 7.40-7.47 (2H, m), 7.70-7.86 (4H, m). White crystal.

KOK2087

Formula 61

KOK-2087

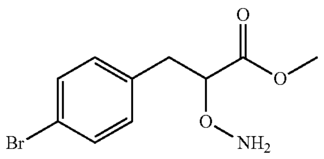

$^1$H-NMR ($CDCl_3$, 270 MHz) δ ppm: 2.86-3.04 (2H, m), 3.75 (3H, s), 4.37 (1H, dd, J=8.2, 4.8 Hz), 5.67 (2H, s), 7.04-7.12 (2H, m), 7.37-7.44 (2H, m). White crystal.

KOK2090

Formula 62

KOK-2090

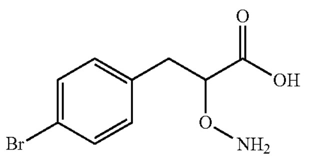

$^1$H-NMR (DMSO-$d_6$, 270 MHz) δ ppm: 2.82 (1H, dd, J=14.3, 8.2 Hz), 2.91 (1H, dd, J=14.3, 5.1 Hz), 4.15 (1H, dd, J=8.2, 5.1 Hz), 7.13-7.22 (2H, m), 7.40-7.49 (2H, m), 8.34 (2H, brs). White crystal.

Compounds were synthesized in accordance with FIG. 2-13. KOK2067 was synthesized in the same conditions as used in Step 3, KOK2110 in Step 4 and KOK2111 in Step 5. KOK2066 was synthesized in accordance with Step 13 shown below.

Synthesis of KOK2066 (Step 13)

Formula 63

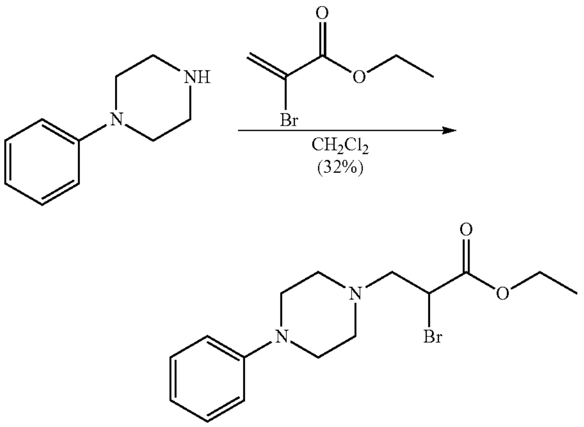

KOK-2066

1-Phenylpiperazine (216 mg, 1.34 mmol) and ethyl 2-bromoacrylate (239 mg, 1.34 mmol) were dissolved in dichloromethane (5 ml) and stirred at room temperature 16 hours. The reaction solution was directly purified by silica gel column chromatography (hexane:ethyl acetate=3:1) to obtain the titled compound (colorless oily substance: 145 mg, 32%).

$^1$H-NMR ($CDCl_3$, 270 MHz) δ ppm: 1.30 (3H, t, J=7.1 Hz), 2.58-2.90 (5H, m), 3.07-3.21 (5H, m), 4.18-4.31 (3H, m), 6.80-6.95 (3H, m), 7.18-7.30 (2H, m).

KOK2067

Formula 64

KOK-2067

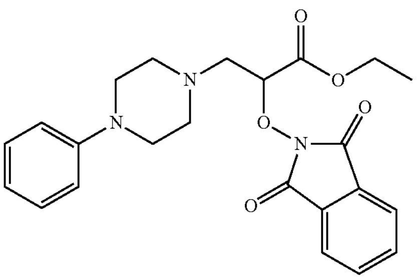

$^1$H-NMR ($CDCl_3$, 270 MHz) δ ppm: 1.30 (3H, t, J=7.1 Hz), 2.64-2.87 (4H, m), 2.95 (1H, dd, J=13.9, 4.1 Hz), 3.03-3.23 (5H, m), 4.16-4.36 (2H, m), 5.05 (1H, dd, J=7.6, 4.1 Hz), 6.78-6.92 (3H, m), 7.18-7.29 (2H, m), 7.68-7.78 (2H, m), 7.78-7.87 (2H, m). Yellow oily substance.

KOK2110

Formula 65

KOK-2110

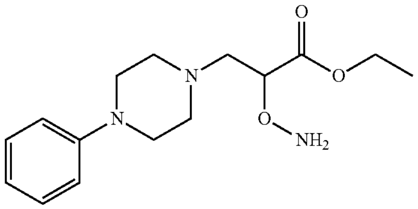

$^1$H-NMR ($CDCl_3$, 270 MHz) δ ppm: 1.30 (3H, t, J=7.1 Hz), 2.54-2.88 (6H, m), 3.18 (4H, t, J=5.0 Hz), 4.12-4.34 (2H, m), 4.42 (1H, dd, J=7.8, 3.1 Hz), 5.78 (2H, brs), 6.77-6.96 (3H, m), 7.16-7.31 (2H, m). White crystal.

KOK2111

Formula 66

KOK-2111

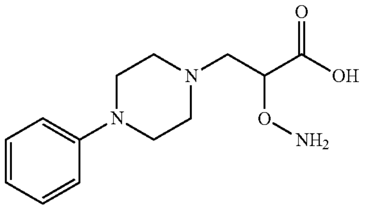

$^1$H-NMR ($CD_3OH$, 270 MHz) δ ppm: 2.98-3.10 (6H, m), 3.22-3.34 (4H, m), 4.30 (1H, dd, J=7.8, 4.2 Hz), 6.80-6.91 (1H, m), 6.91-7.02 (2H, m), 7.18-7.28 (2H, m). White crystal.

Compounds were synthesized in accordance with FIG. 2-14. KOK2115 was synthesized in the same conditions as used in Step 9, KOK2116 in Step 3, KOK2117 in Step 4 and KOK2118 in Step 5.

KOK2115

Formula 67

KOK-2115

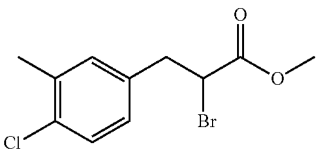

$^1$H-NMR ($CDCl_3$, 270 MHz) δ ppm: 2.35 (3H, s), 3.17 (1H, dd, J=14.0, 7.1 Hz), 3.42 (1H, dd, J=14.0, 8.2 Hz), 3.73 (3H, s), 4.36 (1H, dd, J=8.2, 7.1 Hz), 6.97 (1H, dd, J=8.2, 2.3 Hz), 7.07 (1H, d, J=2.3 Hz), 7.26 (1H, d, J=8.2 Hz). Brown oily substance.

KOK2116

Formula 68

KOK-2116

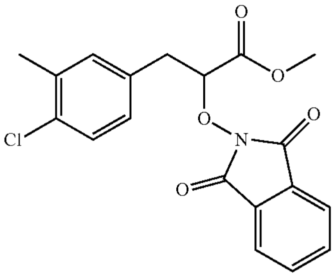

$^1$H-NMR ($CDCl_3$, 270 MHz) δ ppm: 2.34 (3H, s), 3.20-3.36 (2H, m), 3.74 (3H, s), 4.97 (1H, t, J=6.9 Hz), 7.08 (1H, dd, J=8.2, 2.1 Hz), 7.20 (1H, d, J=2.1 Hz), 7.26 (1H, d, J=8.2 Hz), 7.70-7.86 (4H, m). Colorless oily substance.

KOK2117

Formula 69

KOK-2117

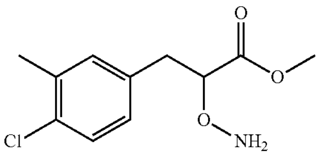

$^1$H-NMR ($CDCl_3$, 270 MHz) δ ppm: 2.34 (3H, s), 2.89 (1H, dd, J=14.3, 8.4 Hz), 2.98 (1H, dd, J=14.3, 4.6 Hz), 3.75 (3H, s), 4.37 (1H, dd, J=8.4, 4.6 Hz), 5.67 (2H, s), 6.97 (1H, dd, J=8.1, 2.1 Hz), 7.07 (1H, d, J=2.1 Hz), 7.25 (1H, d, J=8.1 Hz). White crystal.

KOK2118

Formula 70

KOK-2118

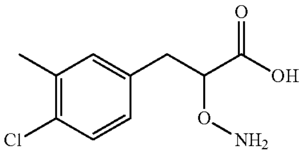

$^1$H-NMR (DMSO-$d_6$, 270 MHz) δ ppm: 2.28 (3H, s), 2.73 (1H, dd, J=14.3, 9.1 Hz), 2.94 (1H, dd, J=14.3, 3.6 Hz), 3.98 (1H, dd, J=9.1, 3.6 Hz), 7.07 (1H, d, J=8.1, 2.0 Hz), 7.19 (1H, d, J=2.0 Hz), 7.26 (1H, d, J=8.1 Hz). White crystal.

KOK1114 was synthesized in accordance with FIG. 2-1 (Step 14).

KOK1114

Formula 71

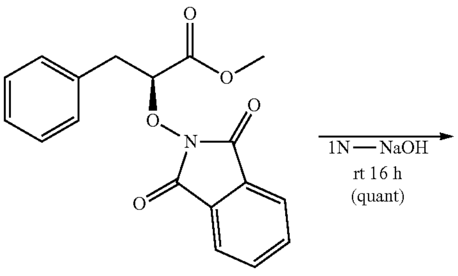

KOK-1101

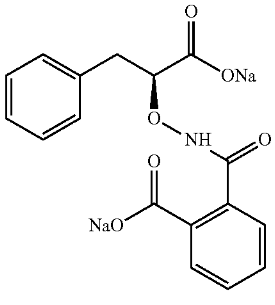

KOK-1114

KOK1101 (100 mg, 0.307 mmol) was suspended in a 1N aqueous sodium hydroxide solution (0.6 ml) and stirred at room temperature for 16 hours. Insoluble material was filtered off and the filtrate was concentrated under reduced pressure, then dried to obtain the titled compound (white crystal: 115 mg, 100%).

$^1$H-NMR ($D_2O$, 270 MHz) δ ppm: 3.04 (2H, d, J=5.6 Hz), 4.48 (1H, t, J=5.6 Hz), 7.10-7.50 (10H, m). White crystal.

Compounds were synthesized in accordance with FIG. 2-15. KOK2120 was synthesized in the same conditions as used in Step 3, KOK2121 in Step 4 and KOK2122 in Step 5.

KOK2120

Formula 72

KOK-2120

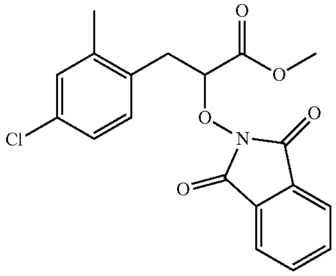

$^1$H-NMR ($CDCl_3$, 270 MHz) δ ppm: 2.38 (3H, s), 3.26 (1H, dd, J=14.5, 7.3 Hz), 3.37 (1H, dd, J=14.5, 7.3 Hz), 3.74 (3H, s), 4.93 (1H, t, J=7.3 Hz), 7.08-7.23 (3H, m), 7.70-7.86 (4H, m). White crystal.

KOK2121

Formula 73

KOK-2121

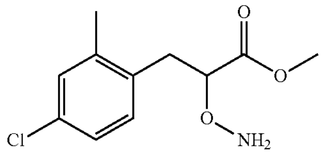

$^1$H-NMR ($CDCl_3$, 270 MHz) δ ppm: 2.30 (3H, s), 2.82-3.02 (2H, m), 3.74 (3H, s), 4.35 (1H, dd, J=8.4, 5.3 Hz), 5.67 (2H, s), 7.03-7.15 (3H, m). Light brown oily substance.

KOK2122

Formula 74

KOK2122

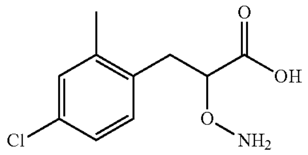

$^1$H-NMR (DMSO-$d_6$, 270 MHz) δ ppm: 2.26 (3H, s), 2.75-2.94 (2H, m), 4.14 (1H, dd, J=8.2, 5.3 Hz), 7.08-7.22 (3H, m). White crystal.

Compounds were synthesized in accordance with FIG. 2-16. KOK2153 was synthesized in the same conditions as used in Step 3, KOK2154 in Step 4 and KOK2155 in Step 5.

KOK2153

Formula 75

KOK-2153

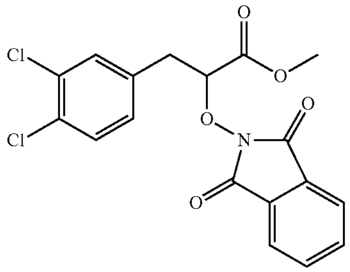

$^1$H-NMR ($CDCl_3$, 270 MHz) δ ppm: 3.20-3.38 (2H, m), 3.76 (3H, s), 4.96 (1H, t, J=6.4 Hz), 7.21 (1H, dd, J=8.2, 2.1 Hz), 7.39 (1H, d, J=8.2 Hz), 7.47 (1H, d, J=2.1 Hz), 7.70-7.88 (4H, m). White crystal.

KOK2154

Formula 76

KOK-2154

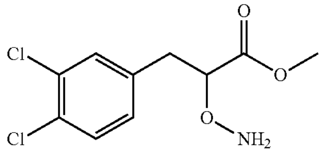

$^1$H-NMR ($CDCl_3$, 270 MHz) δ ppm: 2.80-3.10 (2H, m), 2.76 (3H, s), 4.27-4.45 (1H, m), 5.69 (2H, s), 6.98-7.13 (1H, m), 7.20-7.43 (2H, m). Yellow oily substance.

KOK2155

Formula 77

KOK-2155

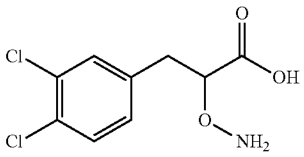

$^1$H-NMR (DMSO-$d_6$, 270 MHz) δ ppm: 2.80-3.02 (2H, m), 4.18 (1H, dd, J=8.4, 4.6 Hz), 7.23 (1H, dd, J=8.2, 2.0 Hz), 7.50 (1H, d, J=2.0 Hz), 7.53 (1H, d, J=8.2 Hz). White crystal.

Compounds were synthesized in accordance with FIG. 2-17. KOK2157 was synthesized in the same conditions as used in Step 10, KOK2166 in Step 11, KOK2168 in Step 12, KOK2169 in Step 3, KOK2172 in Step 4 and KOK2173 in Step 5.

KOK2157

Formula 78

KOK-2157

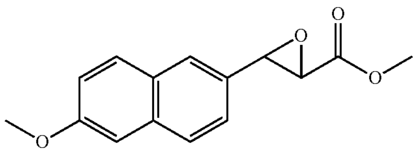

$^1$H-NMR ($CDCl_3$, 270 MHz) δ ppm: 3.62 (1H, d, J=1.8 Hz), 3.84 (3H, s), 3.91 (3H, s), 4.23 (1H, d, J=1.8 Hz), 7.08-7.19 (2H, m), 7.27 (1H, dd, J=8.4, 1.8 Hz), 7.66-7.76 (3H, m). White crystal.

KOK2166.

Formula 79

KOK-2166

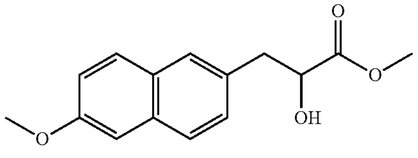

$^1$H-NMR ($CDCl_3$, 270 MHz) δ ppm: 2.75 (1H, brs), 3.02 (1H, dd, J=14.7, 4.5 Hz), 3.18 (1H, dd, J=14.7, 4.5 Hz), 3.69 (3H, s), 3.83 (3H, s), 4.40-4.49 (1H, m), 7.00-7.10 (2H, m), 7.23 (1H, dd, J=8.4, 1.8 Hz), 7.52 (1H, s), 7.60 (2H, d, J=8.4 Hz). White crystal.

KOK2168

Formula 80

KOK-2168

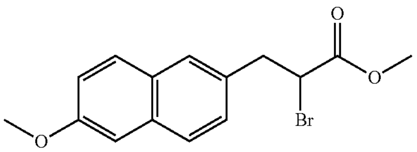

$^1$H-NMR ($CDCl_3$, 270 MHz) δ ppm: 3.35 (1H, dd, J=14.0, 6.9 Hz), 3.58 (1H, dd, J=14.0, 8.6 Hz), 3.69 (3H, s), 3.89 (3H, s), 4.48 (1H, dd, J=8.6, 6.9 Hz), 7.07-7.16 (2H, m), 7.27 (1H, dd, J=8.4, 1.7 Hz), 7.58 (1H, s), 7.67 (2H, d, J=7.9 Hz). Light yellow oily substance.

KOK2169

Formula 81

KOK-2169

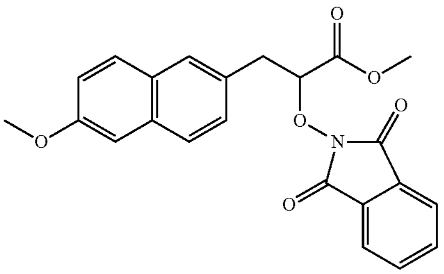

$^1$H-NMR ($CDCl_3$, 270 MHz) δ ppm: 3.38-3.55 (2H, m), 3.70 (3H, s), 3.86 (3H, s), 5.08 (1H, t, J=6.9 Hz), 7.04-7.13 (2H, m), 7.40 (1H, dd, J=8.4, 1.7 Hz), 7.61-7.79 (7H, m). White crystal.

KOK2172

Formula 82

KOK-2172

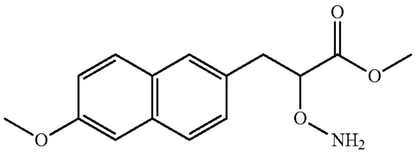

$^1$H-NMR ($CDCl_3$, 270 MHz) δ ppm: 3.02-3.21 (2H, m), 3.73 (3H, s), 3.90 (3H, s), 4.48 (1H, dd, J=8.4, 5.0 Hz), 5.67 (2H, s), 7.07-7.15 (2H, m), 7.31 (1H, dd, J=8.4, 1.7 Hz), 7.58 (1H, s), 7.67 (2H, d, J=8.4 Hz). White crystal.

KOK2173

Formula 83

KOK-2173

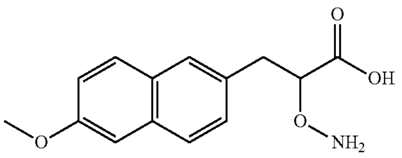

$^1$H-NMR (DMSO-$d_6$, 270 MHz) δ ppm: 2.96 (1H, dd, J=14.2, 8.4 Hz), 3.07 (1H, dd, J=14.2, 4.8 Hz), 3.85 (3H, s), 4.25 (1H, dd, J=8.4, 4.8 Hz), 7.12 (1H, dd, J=8.9, 2.6 Hz), 7.27 (1H, d, J=2.5 Hz), 7.35 (1H, dd, J=8.6, 1.4 Hz), 7.64 (1H, s), 7.67-7.78 (2H, m). White crystal.

Compounds were synthesized in accordance with FIG. 2-18.

Synthesis of KOK3045 (Step 15)

Formula 84

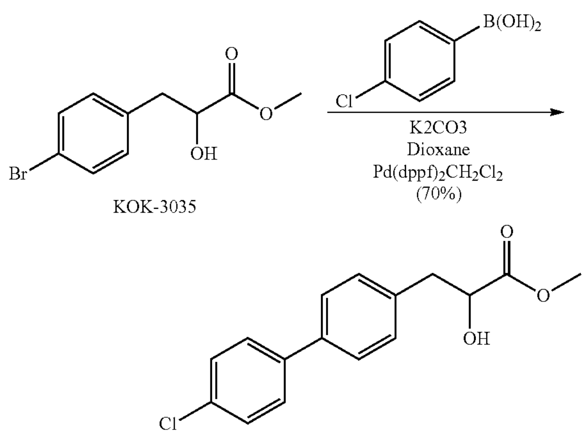

KOK-3035

KOK-3045

Methyl 3-(4-bromophenyl)-2-hydroxy propionate (360 mg, 1.389 mmol), p-chlorophenylboronic acid (326 mg, 2.084 mmol), [1,1'-bis(diphenylphosphino)ferrocene]dichloropalladium (II), dichloromethane adduct (57 mg, 0.07 mmol), potassium carbonate (288 mg, 2.084 mmol) and dioxane (5 ml) were stirred under a nitrogen atmosphere at 90° C. for 3 hours. The reaction solution was concentrated under reduced pressure and directly purified by silica gel chromatography (hexane:ethyl acetate=4:1) to obtain the titled compound (white crystal: 284 mg, 70%).

$^1$H-NMR ($CDCl_3$, 270 MHz) δ ppm: 2.75 (1H, d, J=6.1 Hz), 3.00 (1H, dd, J=14.0, 6.9 Hz), 3.18 (1H, dd, J=14.0, 4.3 Hz), 3.80 (3H, s), 4.44-4.53 (1H, m), 7.25-7.32 (2H, m), 7.35-7.42 (2H, m), 7.45-7.52 (4H, m). White crystal.

KOK3049 was synthesized in the same conditions as used in Step 12, KOK3050 in Step 3, KOK3052 in Step 4 and KOK3053 in Step 5.

KOK3049

Formula 85

KOK-3049

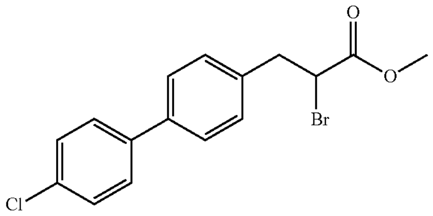

$^1$H-NMR ($CDCl_3$, 270 MHz) δ ppm: 3.28 (1H, dd, J=14.0, 7.1 Hz), 3.51 (1H, dd, J=14.0, 8.2 Hz), 3.75 (3H, s), 4.43 (1H, dd, J=8.2, 7.1 Hz), 7.20-7.56 (8H, m). Colorless oily substance.

KOK3050

Formula 86

KOK-3050

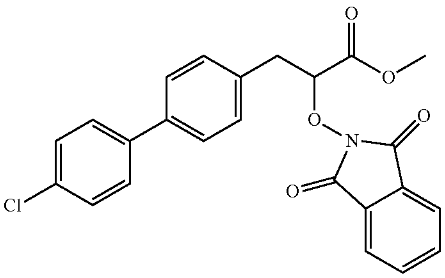

$^1$H-NMR ($CDCl_3$, 270 MHz) δ ppm: 3.30-3.47 (2H, m), 3.75 (3H, s), 5.05 (1H, t, J=6.9 Hz), 7.34-7.44 (4H, m), 7.44-7.53 (4H, m), 7.70-7.86 (4H, m). White solid substance.

KOK3052

Formula 87

KOK-3052

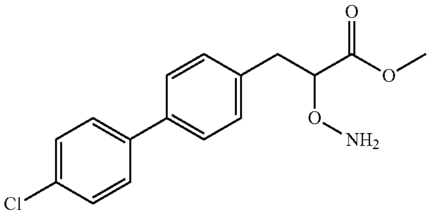

$^1$H-NMR ($CDCl_3$, 270 MHz) δ ppm: 2.95-3.13 (2H, m), 3.77 (3H, s), 4.45 (1H, dd, J=8.4, 4.8 Hz), 5.69 (2H, s), 7.25-7.32 (2H, m), 7.35-7.42 (2H, m), 7.44-7.53 (4H, m). White crystal.

KOK3053

Formula 88

KOK-3053

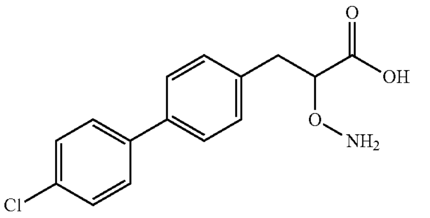

$^1$H-NMR (DMSO-$d_6$, 270 MHz) δ ppm: 2.81-3.03 (2H, m), 4.22 (1H, dd, J=8.2, 5.0 Hz), 7.28-7.36 (2H, m), 7.45-7.53 (2H, m), 7.53-7.62 (2H, m), 7.62-7.72 (2H, m). White crystal.

KOK2165 was synthesized in accordance with FIG. 2-19. KOK2165 was synthesized in the same conditions as used in Step 6.

Formula 89

KOK-2165

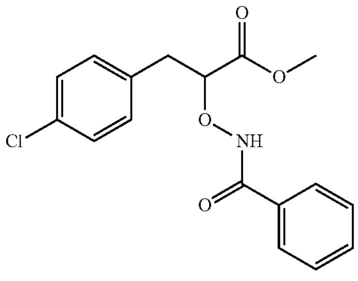

$^1$H-NMR ($CDCl_3$, 270 MHz) δ ppm: 3.05-3.25 (2H, m), 3.63 (3H, s), 4.89 (1H, t, J=6.1 Hz), 7.19 (4H, s), 7.27-7.38 (2H, m), 7.38-7.50 (1H, m), 7.63-7.75 (2H, m), 10.07 (1H, s). Brown oily substance.

2. Use Examples

(1) Quantification of Endogenous IAA Amount

*Arabidopsis*

*Arabidopsis* (col-0) was cultured in a plate horizontally set and using ½ MS medium containing 1.0% sucrose and 0.8% agar under continuous white light at 22° C. for 6 days, and thereafter subjected to liquid shaking culture in ½ MS medium containing 1.0% sucrose under continuous white light at 22° C. for 24 hours. Subsequently, the compound of the present invention (30 μM) was added to the medium and subjected to liquid shaking culture under continuous white light at 22° C. for 3 hours to quantify IAA endogenous amount. The IAA endogenous amount was measured by use of LC-MS/MS in accordance with the method of Soeno et al. (Plant Cell Physiology 51: 524-536 (2010)). The results are shown in FIG. 3.

(2-1) Growth Test

*Arabidopsis*

*Arabidopsis* was cultured in a plate vertically set and using ½ MS medium containing 1.5% sucrose, 0.8% agar and the compound of the present invention (30 μM) under continuous white light at 22° C. for 8 days. Morphology of *arabidopsis* was observed to evaluate the effect of the compound of the present invention.

The results are shown in Table 1. Morphologies of *arabidopsis* whose growth was inhibited compared to DMSO control plant are shown in FIG. 4.

TABLE 1

| Inhibitor | Growth inhibitory effect |
|---|---|
| L-AOPP | |
| KOK 1101 | ○ |
| KOK 1108 | ○ |
| KOK 1114 | |
| KOK 1145 | |
| KOK 1148 | |
| KOK 1149 | |
| KOK 1154 | |
| KOK 1157 | ○ |
| KOK 1160 | ○ |
| KOK 1161 | ○ |
| KOK 1162 | ○ |
| KOK 1165 | ○ |
| KOK 1166 | ○ |
| KOK 1167 | ○ |
| KOK 1168 | ○ |
| KOK 1169 | ○ |
| KOK 1172 | ○ |
| KOK 1174 | ○ |
| KOK 1175 | ○ |
| KOK 1176 | ○ |
| KOK 1178 | ○ |
| KOK 1179 | ○ |
| KOK 1180 | |
| KOK 1183 | ○ |
| KOK 1185 | ○ |
| KOK 1186 | ○ |
| KOK 1187 | ○ |
| KOK 1190 | |
| KOK 1194 | ○ |
| KOK 1198 | ○ |
| KOK 2011 | ○ |
| KOK 2015 | ○ |
| KOK 2016 | ○ |
| KOK 2017 | ○ |
| KOK 2021 | ○ |
| KOK 2022 | |
| KOK 2026 | ○ |
| KOK 2027 | ○ |
| KOK 2029 | ○ |
| KOK 2030 | ○ |
| KOK 2031 | ○ |
| KOK 2036 | |
| KOK 2044 | ○ |
| KOK 2067 | |
| KOK 2087 | |
| KOK 2090 | |
| KOK 2110 | |
| KOK 2111 | |
| KOK 2116 | ○ |
| KOK 2117 | |
| KOK 2118 | |
| KOK 2120 | ○ |
| KOK 2121 | |
| KOK 2122 | ○ |
| KOK 2153 | ○ |
| KOK 2154 | ○ |
| KOK 2155 | ○ |
| KOK 2165 | ○ |
| KOK 2169 | ○ |
| KOK 2172 | ○ |
| KOK 2173 | |
| KOK 3050 | |
| KOK 3052 | ○ |
| KOK 3053 | ○ |

○: Growth inhibition was observed compared to DMSO control plant

(2-2) Growth Test

*Arabidopsis*

*Arabidopsis* was cultured in a plate vertically set and using ½ MS medium containing 1.5% sucrose, 0.8% agar and the compound of the present invention (100 μM) under continuous white light at 22° C. for 8 days. Morphology of *arabidopsis* was observed to evaluate the effect of the compound of the present invention.

Compounds in the presence of which *arabidopsis* rarely grew are shown in Table 2.

TABLE 2

| |
|---|
| KOK 1157 |
| KOK 1162 |
| KOK 1174 |
| KOK 1178 |
| KOK 1183 |
| KOK 1185 |
| KOK 1186 |
| KOK 1194 |
| KOK 1198 |
| KOK 2011 |
| KOK 2017 |
| KOK 2044 |
| KOK 2165 |
| KOK 2172 |

(3) Growth Recovery Test

*Arabidopsis*

*Arabidopsis* was cultured in a plate vertically set and using ½ MS medium containing 1.5% sucrose, 0.8% agar (0.6% Gelrite in the case of KOK1169), the compound of the present invention and IAA under continuous white light at 22° C. for 8 days. Morphology of *arabidopsis* was observed to evaluate the recovery of the plant growth suppressed by the compound of the present invention.

Figures 2, 3, 4, 5:
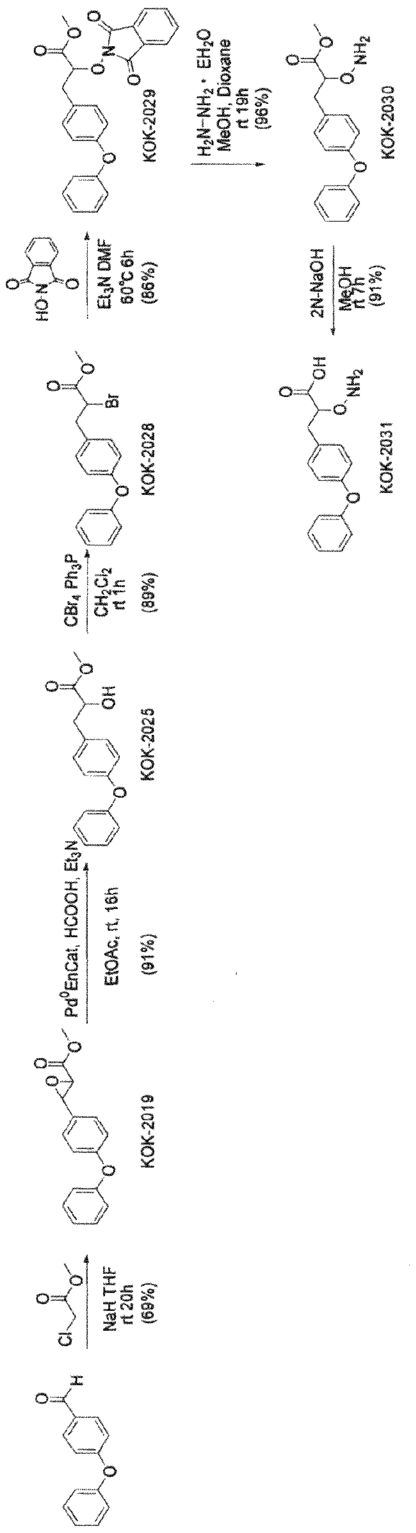

In the test, KOK1101 (30 μM), KOK1160 (30 μM), KOK1165 (30 μM), and KOK1169 (100 μM) were studied. The morphologies of *arabidopsis* cultured are shown in FIG. 5.

In the case of growth inhibition by KOK1101 (30 μM), main root elongation was recovered by simultaneous application with IAA (10 nM) and growth of an aerial part was recovered by simultaneous application with IAA (100 nM).

In the case of growth inhibition by KOK1160 (30 μM), growth of an aerial part and main root elongation were recovered by simultaneous application with IAA (10 nM).

In the case of growth inhibition by KOK1165 (30 μM), growth of an aerial part and main root elongation were recovered by simultaneous application with IAA (10 nM)

In the case of growth inhibition by KOK1169 (100 μM), growth of an aerial part and main root elongation were recovered by simultaneous application with IAA (10 nM).

(4) Growth Test

Tobacco

Tobacco was cultured in a plate vertically set and using ½ MS medium containing 1.5% sucrose and 0.8% agar under continuous white light at 25° C. for 7 days. Thereafter, tobacco was transferred to a plate vertically set and using ½ MS medium containing 1.5% sucrose, 0.8% agar and the compound of the present invention (100 μM) and cultured under continuous white light at 25° C. for 7 days. Morphology of tobacco was observed to evaluate plant growth inhibitory effect of the compound of the present invention.

Figures 2, 3, 4, 5, 6:
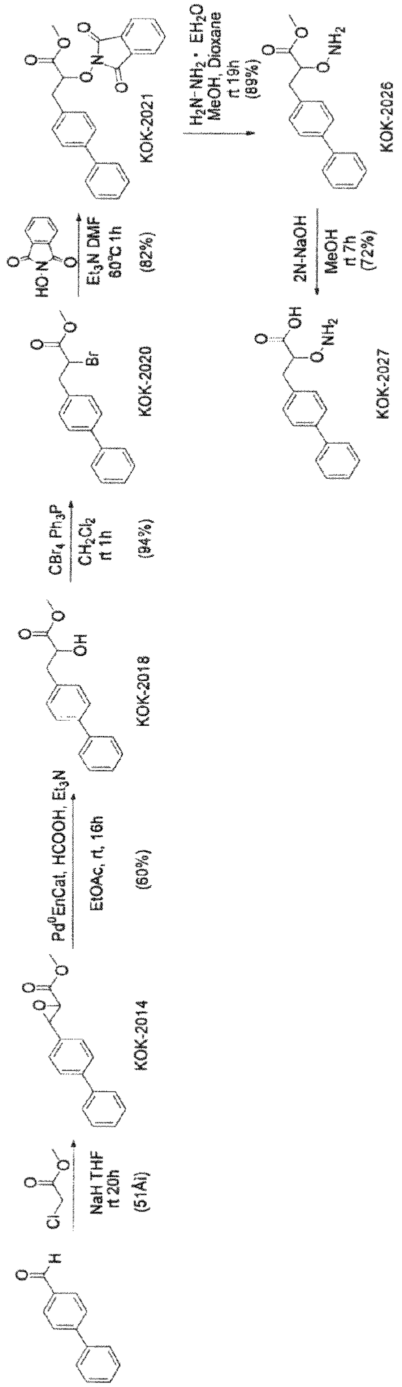

The results are shown in Table 3. Morphologies of tobacco whose growth is inhibited compared to DMSO control plant are shown in FIG. 6 (in FIG. 6, "preculture" shows seedling right before transplant).

TABLE 3

| Inhibitor | Growth inhibitory effect | Note |
|---|---|---|
| L-AOPP | X | |
| KOK 1101 | ○ | |
| KOK 1108 | ○ | |
| KOK 1145 | X | |
| KOK 1157 | ○ | |
| KOK 1160 | ○ | |
| KOK 1165 | ○ | |
| KOK 1167 | ○ | Auxin-excess like morphology |
| KOK 1168 | ○ | |
| KOK 1169 | X | |
| KOK 1174 | ○ | |
| KOK 1176 | X | |
| KOK 1178 | ○ | |
| KOK 1180 | X | |
| KOK 1183 | ○ | |
| KOK 1185 | ○ | |
| KOK 1187 | ○ | Auxin-excess like morphology |
| KOK 1190 | ○ | |
| KOK 2011 | ○ | |
| KOK 2029 | X | |
| KOK 2031 | ○ | |

○: Growth inhibition was observed compared to DMSO control plant (5) Growth Test Lettuce Lettuce was cultured in a plate vertically set and using ½ MS medium containing 1.5% sucrose, 0.8% agar and KOK1101 (30 μM) under continuous white light at 25° C. for 6 days. Morphology of lettuce was observed to evaluate plant growth inhibitory effect of the compound of the present invention.

Figures 2, 3, 4, 5, 6, 7:
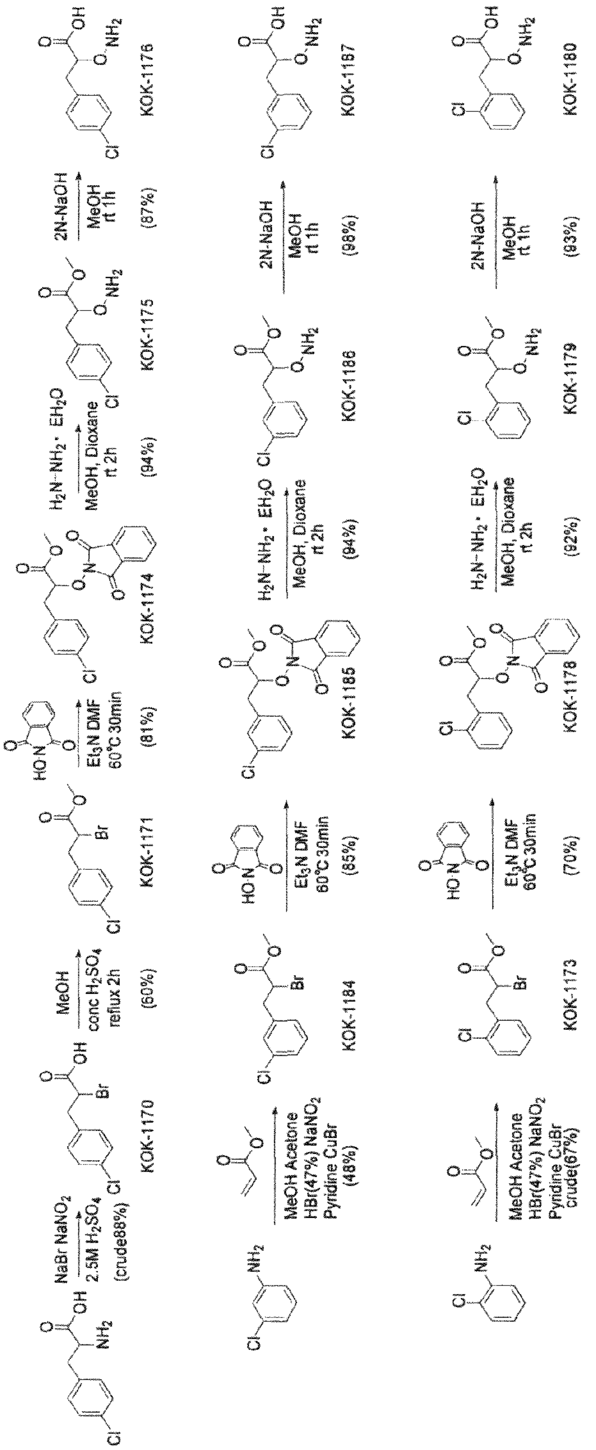

Morphologies of lettuce cultured by use of KOK1101 are shown in FIG. 7. Apparent growth inhibition was observed in the aerial part, whereas, in an underground part, promotion of main root elongation and inhibition of root hair formation were observed.

(6) Protein Activity Inhibitory Test

The inhibitory activities of the compound of the present invention against an IAA biosynthesis enzyme, tryptophan aminotransferase (TAA1), and phenylalanineammonia-lyase (PAL) of *arabidopsis* were evaluated.

(i) TAA1 Inhibitory Test

The test was carried out in accordance with a method described in Cell (2008); 133: pp. 164-176. Specifically, borate buffer (pH 8.5) of a final concentration of 0.5 M, L-Trp (0.3 mM), sodium pyruvate (1 mM), PLP (10 μM), TAA1 (1 μg) and the compound of the present invention (1 μM) were reacted at 35° C. for 30 minutes. Thereafter, 6N HCl (20 μL) was added to terminate the reaction, A330 was measured.

Blank=(−) TAA1 (0.5M Borate buffer (pH 8.5) was used as blank in spectrophotometry).

Figures 2, 3, 4, 5, 6, 7, 8:
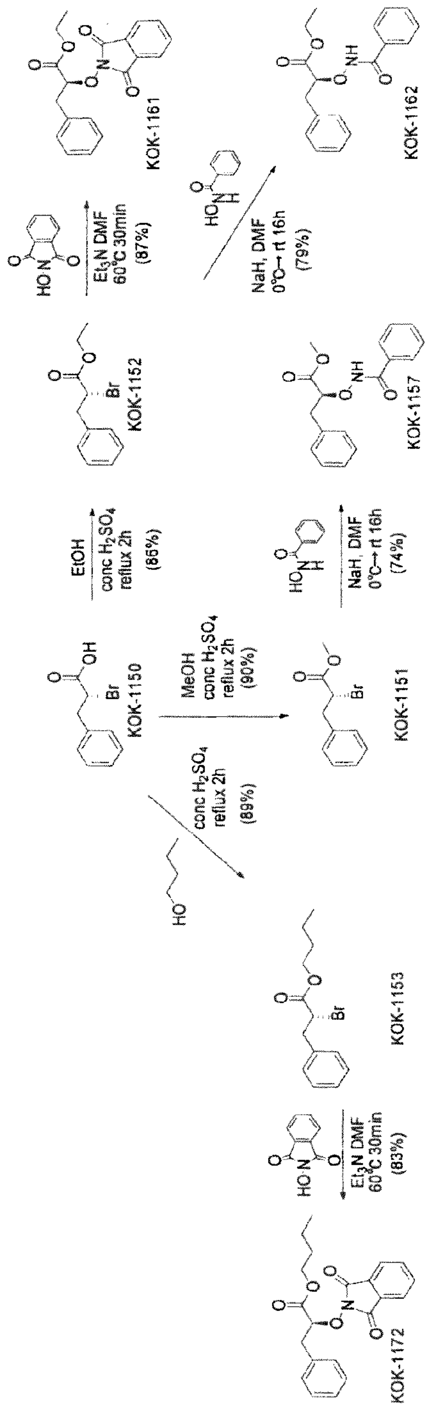

The results are shown in FIG. 8. In the test (in vitro), it was observed that a compound having a free carboxylic acid and a free amine as the carboxyl group and the amino group, respectively, tends to strongly inhibit TAA1. It is presumed that, even a compound having a protected carboxyl group and a protected amino group may inhibit TAA 1 due to removing the protecting groups in the plant body.

(ii) AtPAL2 Inhibitory Test

The test was carried out in accordance with a method described in Phytochem. (2004); 65: pp. 1557-1564, and J. Plant Physiol. (2008); 165: pp. 1491-1499. Specifically, borate buffer (pH 8.5) of a final concentration of 0.1 M, L-Phe (0.06 mM (or 60 μM)), PAL2 (0.5 μg) and the compound of the present invention (15 nM, volume: 500 μL (1% DMSO)) were reacted at 35° C. for 15 minutes. Thereafter, 1N HCl (20 μL) was added to terminate the reaction, A290 was measurement.

Blank=0.1M Borate buffer (pH 8.5) (no change in value at (+) the compound (−) PAL2. No change in value at (+) heat inactivated enzyme).

Figures 2, 3, 4, 5, 6, 7, 8, 9:
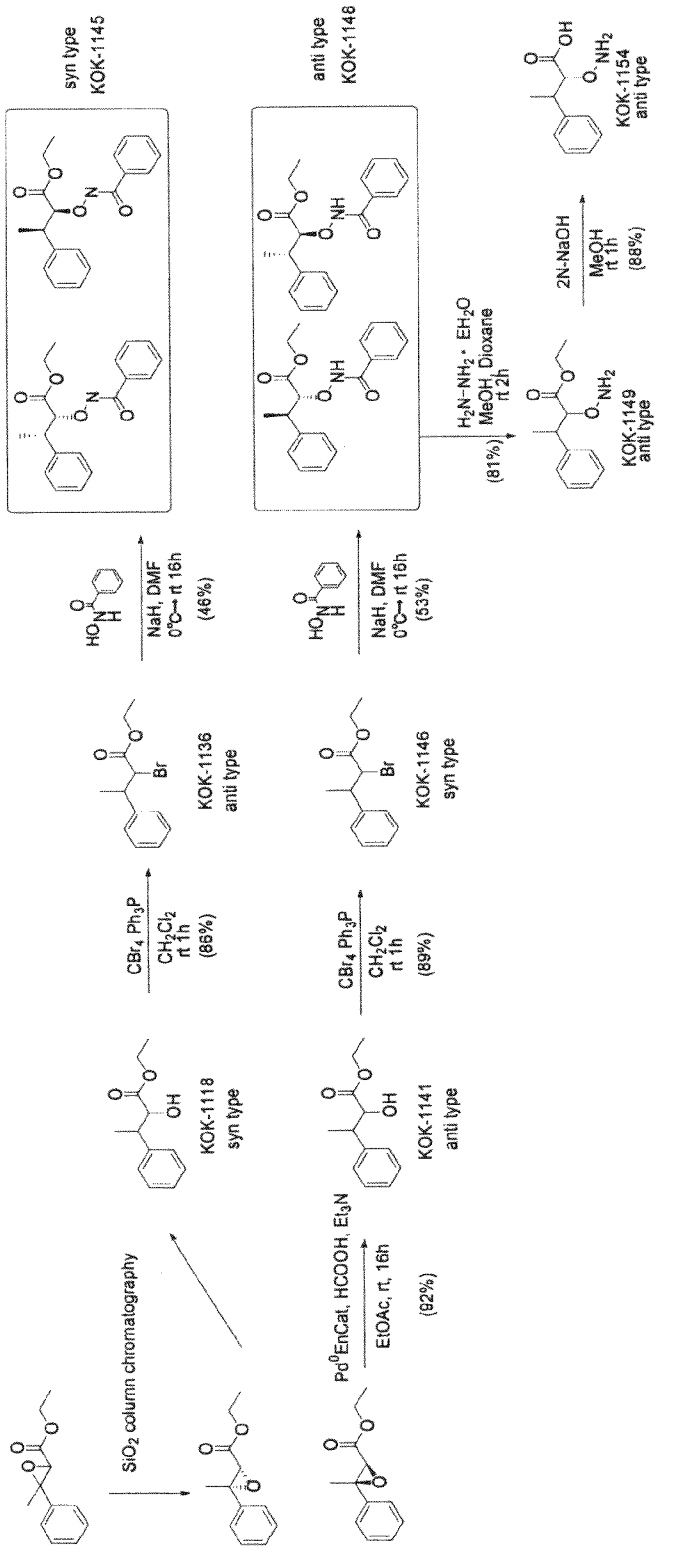

The results are shown in FIG. 9. In the case where the phenyl group of L-AOPP has a large substituent or is modified to a larger ring, it was observed that PAL2 inhibitory activity tends to be low.

(7) Growth Test

Rice

Figures 2, 3, 4, 5, 6, 7, 8, 9, 10:
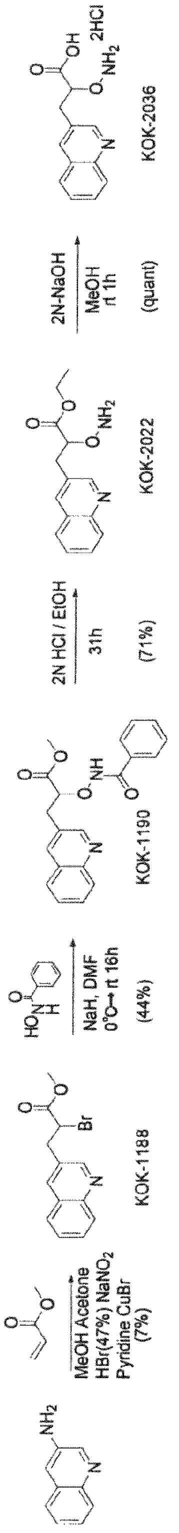

Rice (Nipponbare) at the 6th day after transferred to a KOK1168 (50 μM)-containing medium is shown in FIG. 10 (right figure) (left figure shows DMSO control plant). Growth of seedling treated by KOK1168 was remarkably inhibited.

(8) Growth Test

Tomato

Figures 2, 3, 4, 5, 6, 7, 8, 9, 10, 11:
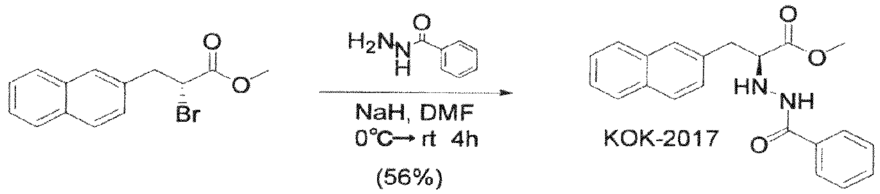

Tomato (Momotaro) at the 6th day after transferred to a plate containing KOK1168 (100 μM) is shown in FIG. 11 (right figure) (left figure shows DMSO control plant). Growth of seedling treated by KOK1168 was remarkably inhibited.

(9) Growth Test

*Physcomitrella patens* Subsp. *Patens*

Figures 2, 3, 4, 5, 6, 7, 8, 9, 10, 11, 12:
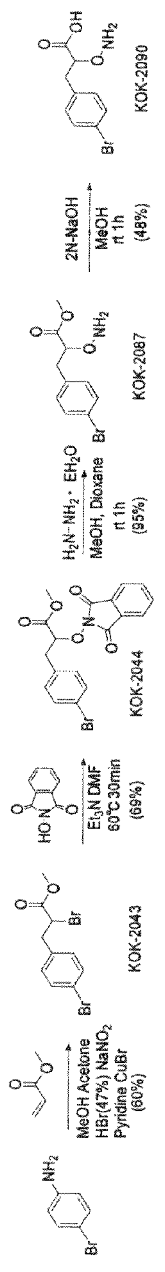
Figures 2, 3, 4, 5, 6, 7, 8, 9, 10, 11, 12, 13:
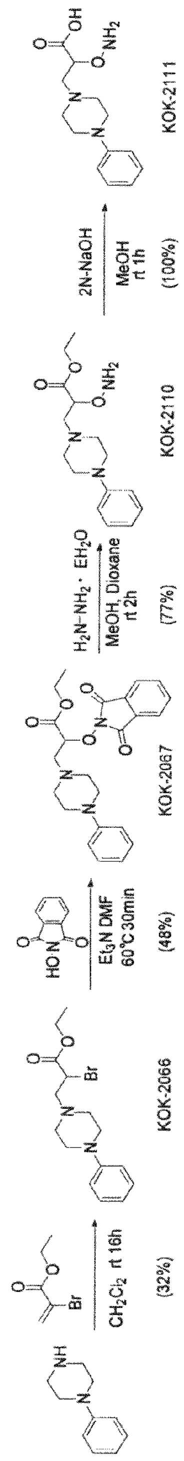
Figures 2, 3, 4, 5, 6, 7, 8, 9, 10, 11, 12, 13, 14:
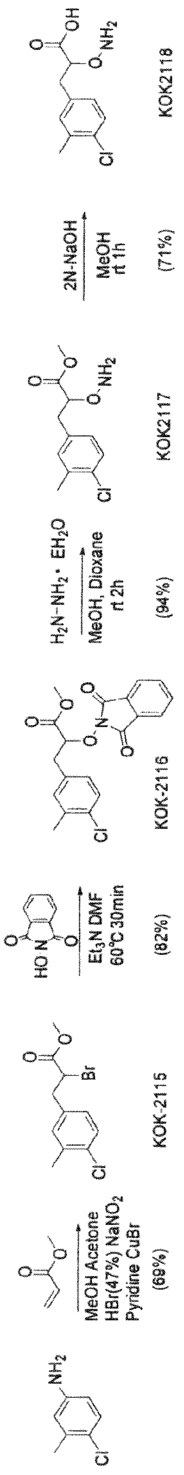
Figures 2, 3, 4, 5, 6, 7, 8, 9, 10, 11, 12, 13, 14, 15:
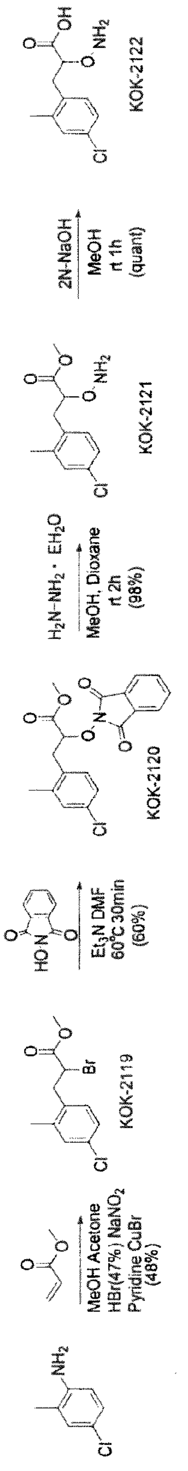
Figures 2, 3, 4, 5, 6, 7, 8, 9, 10, 11, 12, 13, 14, 15, 16:
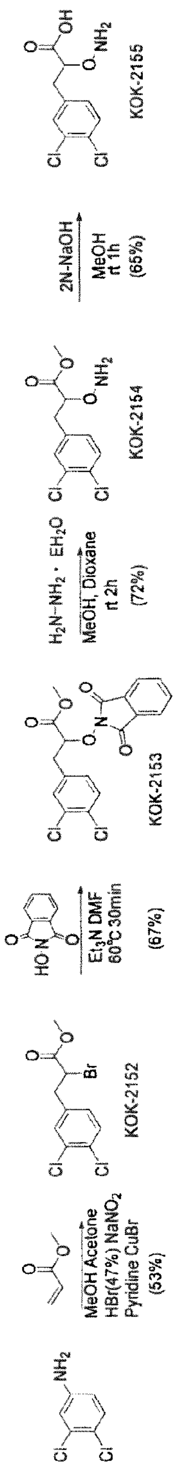
Figures 2, 3, 4, 5, 6, 7, 8, 9, 10, 11, 12, 13, 14, 15, 16, 17:
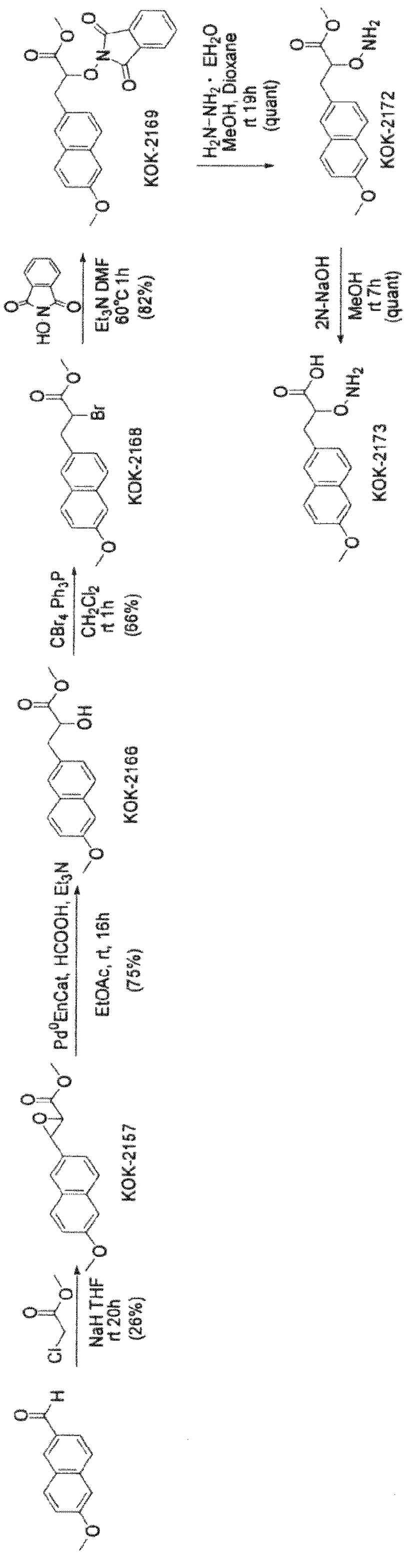
Figures 2, 3, 4, 5, 6, 7, 8, 9, 10, 11, 12, 13, 14, 15, 16, 17, 18:
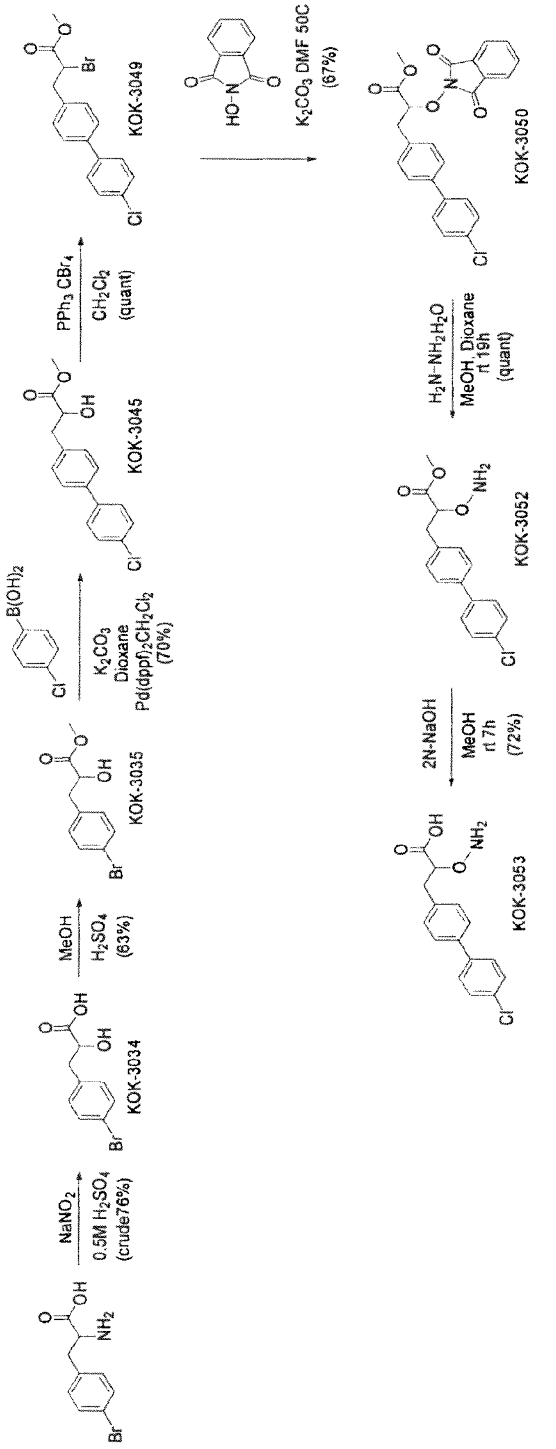
Figures 2, 3, 4, 5, 6, 7, 8, 9, 10, 11, 12, 13, 14, 15, 16, 17, 18, 19:
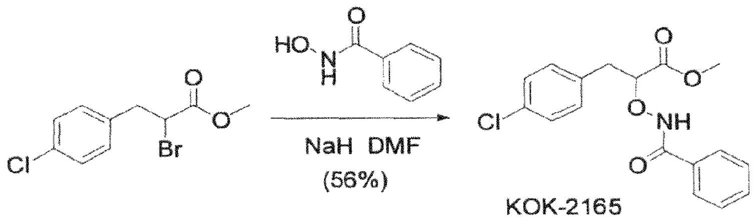
Figure 3:
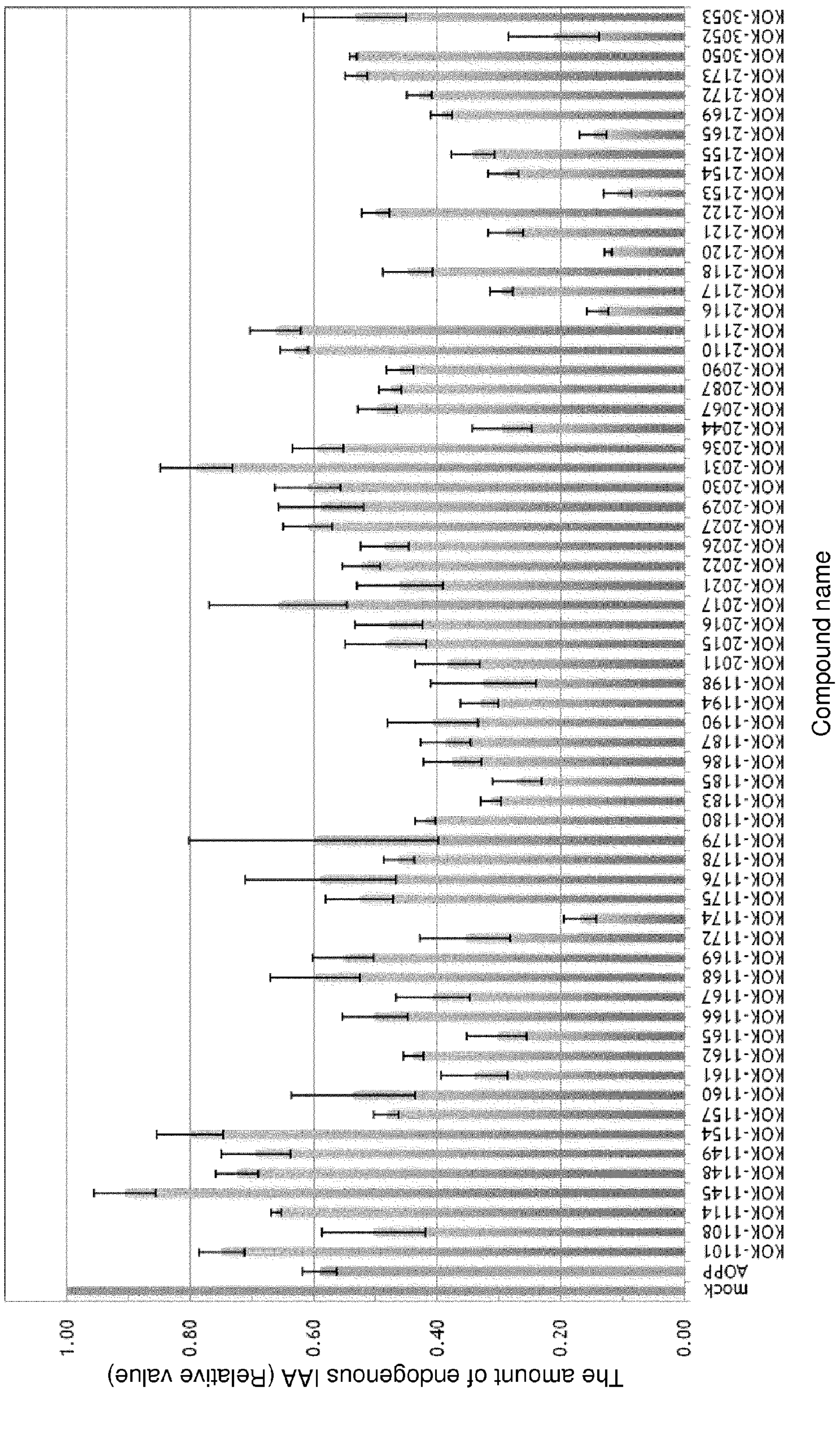
Figures 1, 4:
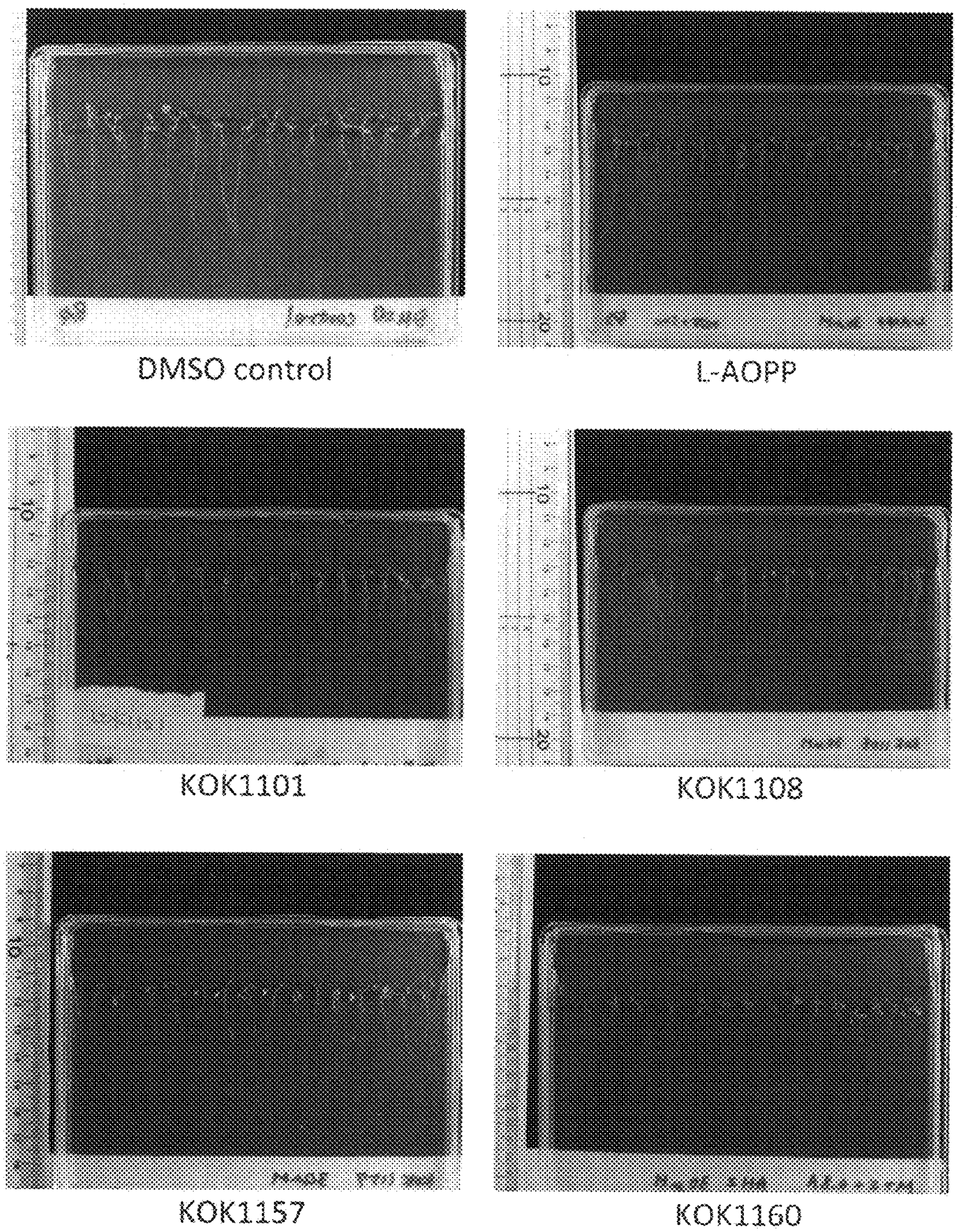
Figure 4:
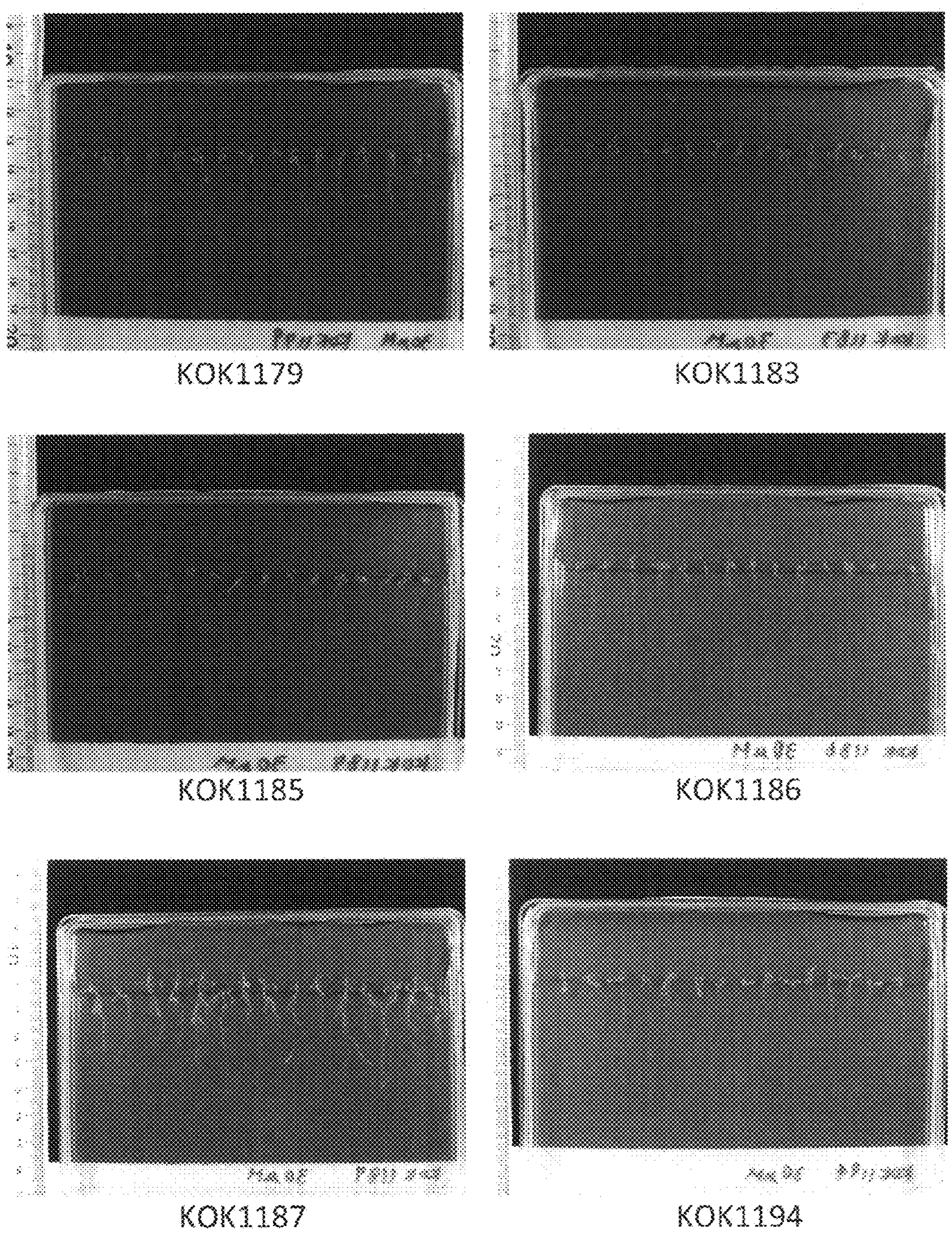
Figures 1, 5:
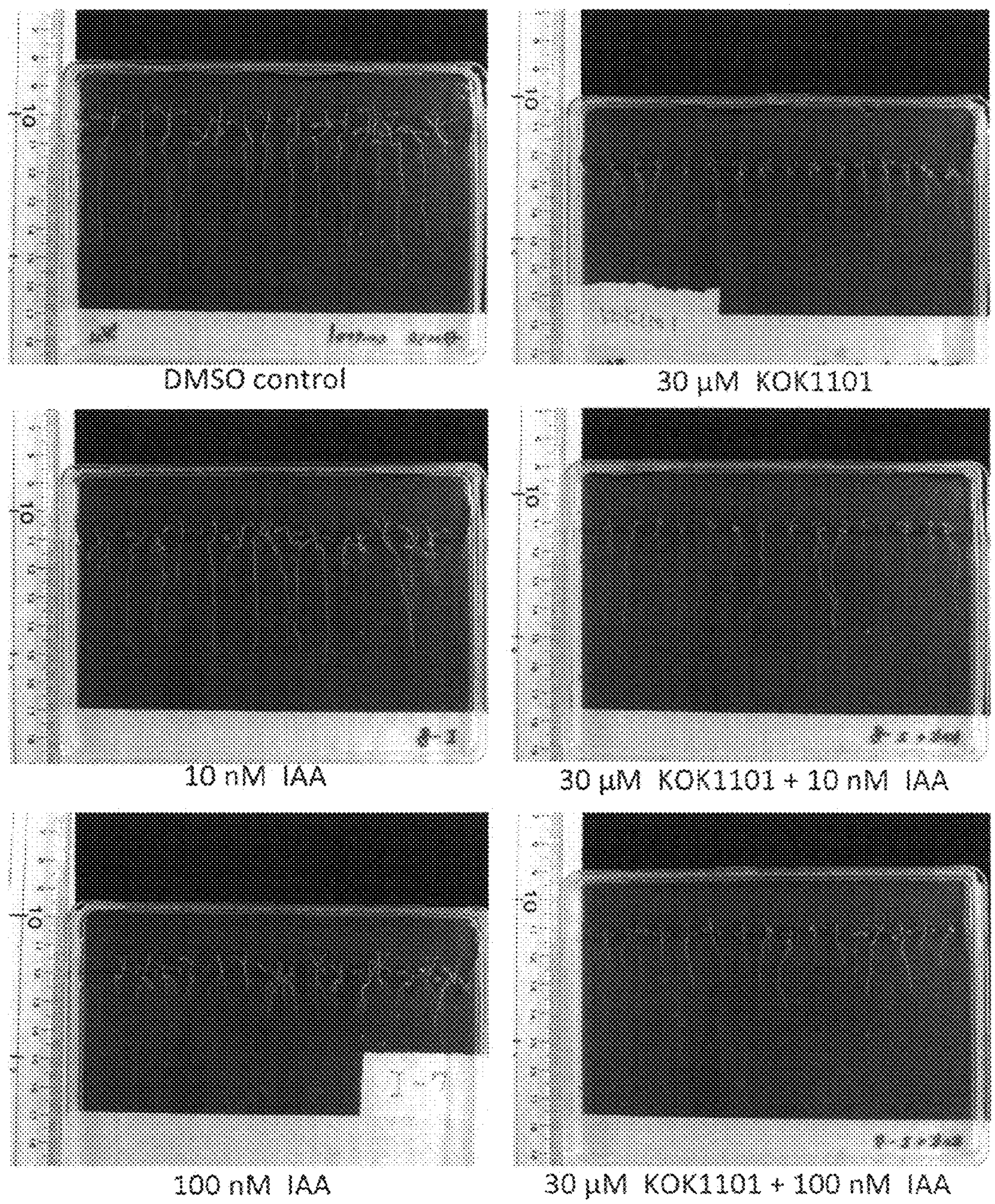
Figures 4, 6:
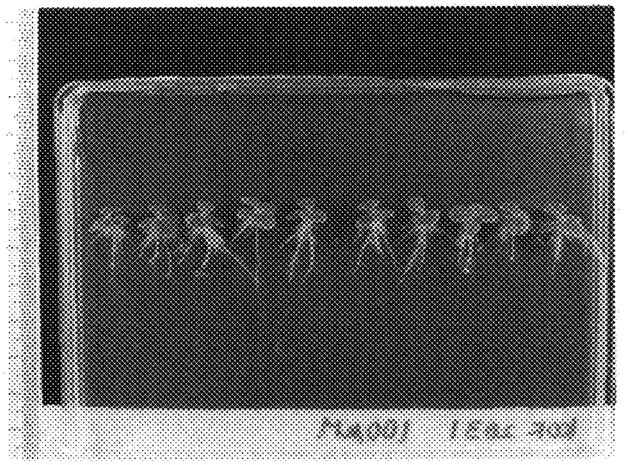
Figure 7:
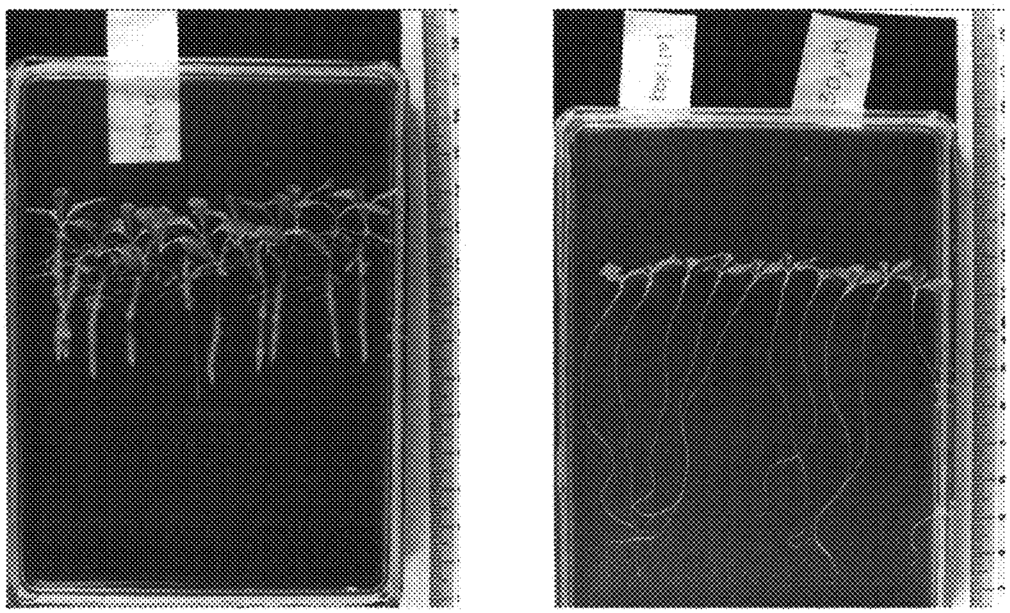
Figure 8:
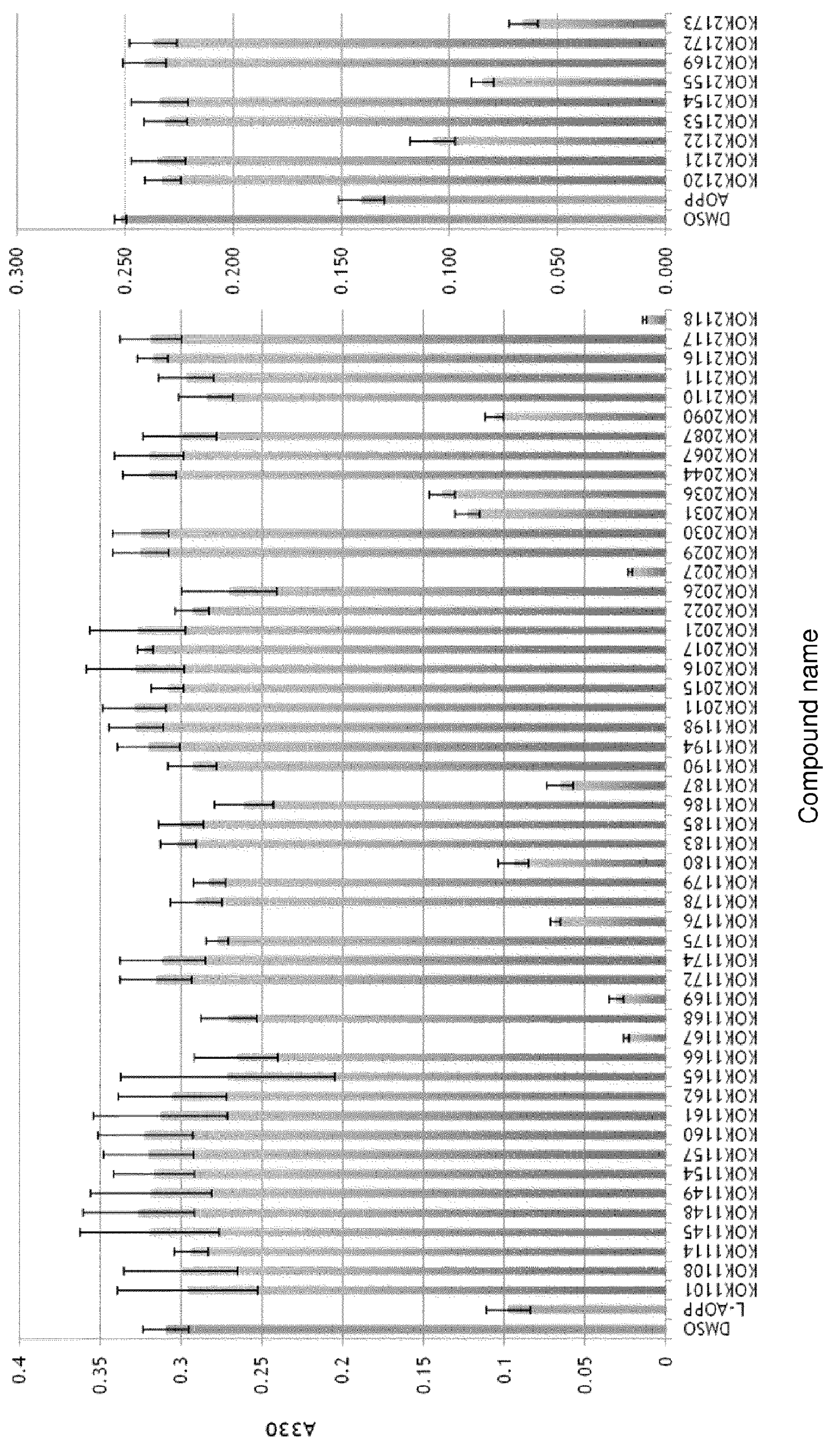
Figure 9:
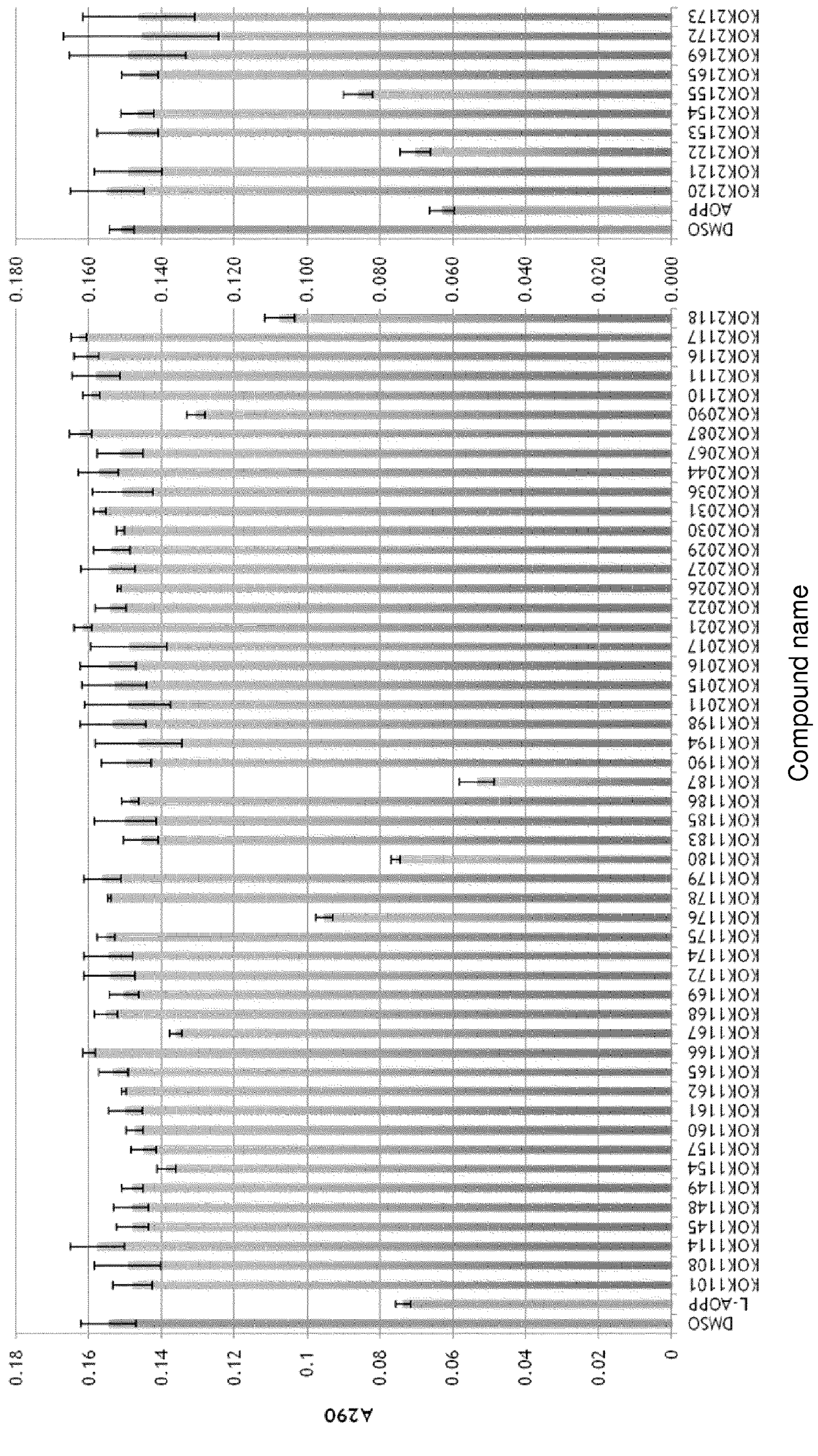
Figure 10:
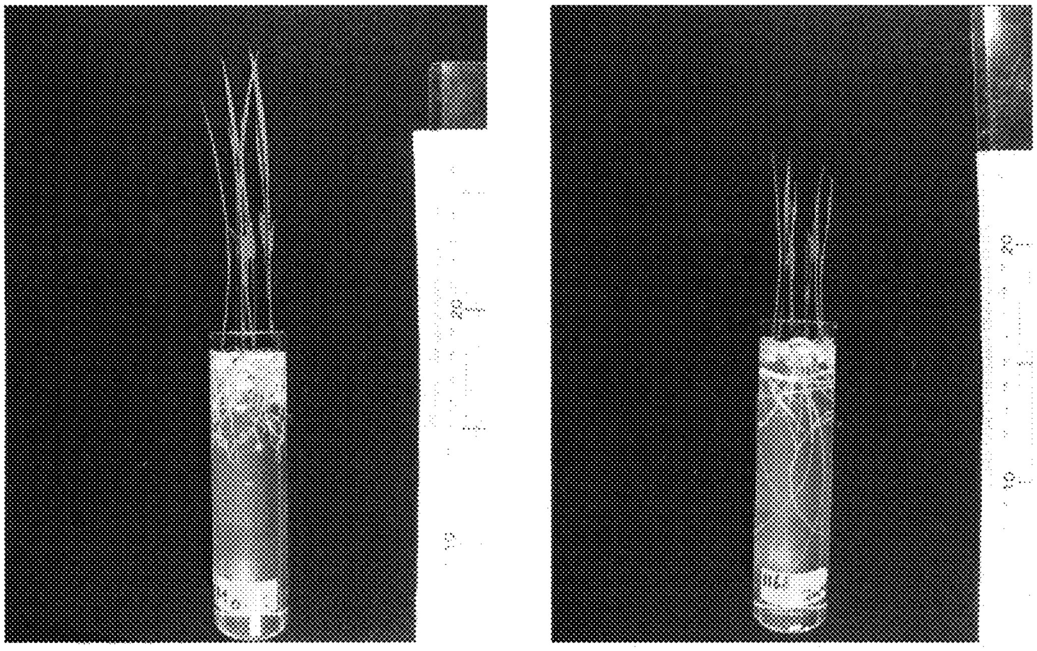
Figure 11:
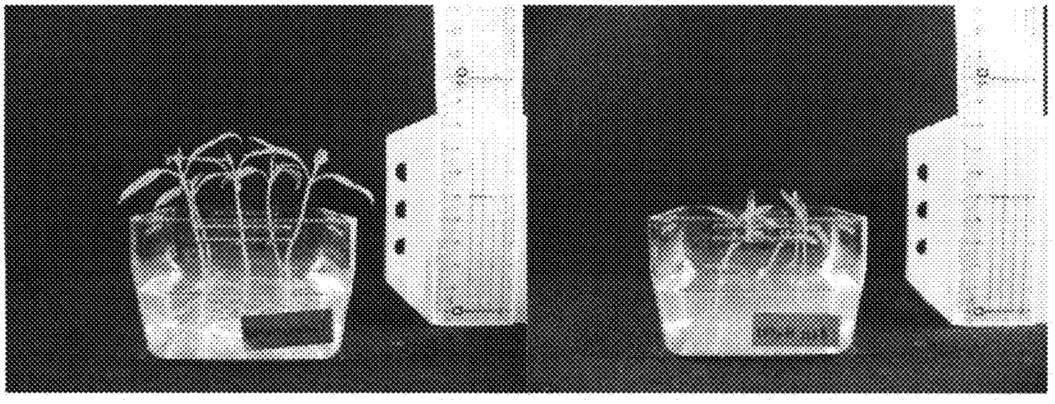
Figure 12:
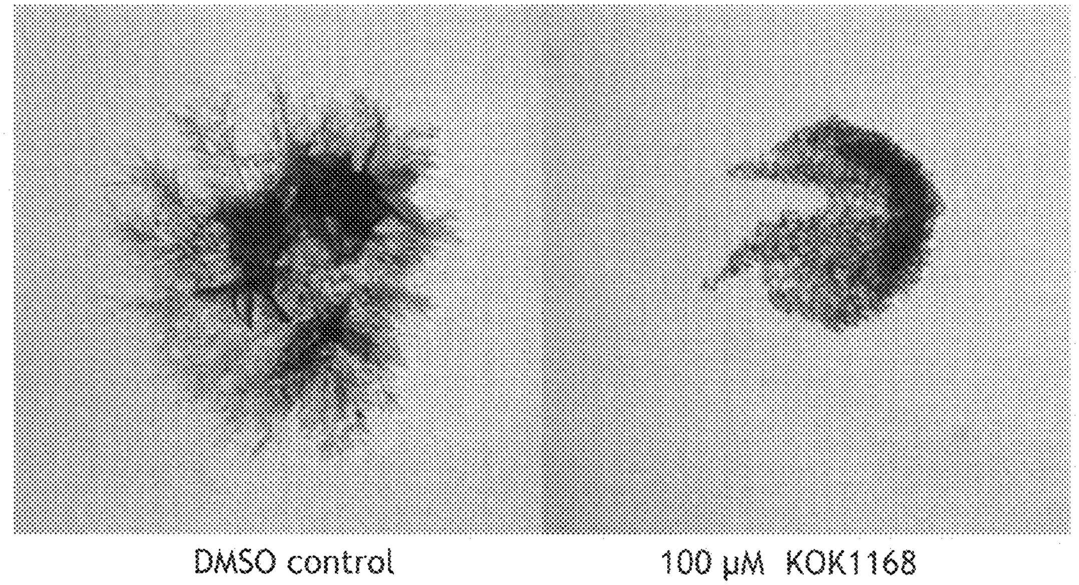

*Physcomitrella patens* subsp. *patens* at the 7th day after transferred to a plate containing KOK1168 (100 μM) is shown in FIG. 12 (right figure) (left figure shows DMSO control plant). Growth of protonemata was remarkably inhibited and differentiation into forage was also inhibited by the treatment with KOK1168.

INDUSTRIAL APPLICABILITY

According to the present invention, an auxin biosynthesis inhibitor superior to L-AOPP can be provided.

All publications, patents and patent applications cited in the specification are incorporated herein in their entirety.

The invention claimed is:

1. A compound represented by general formula (I):

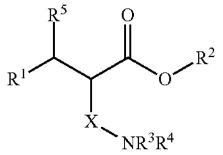

(I)

wherein $R^1$ is chlorophenyl, bromophenyl, biphenyl, phenoxyphenyl, 4-chloro-3-methylphenyl, 4-chloro-2-methylphenyl, dichlorophenyl, 6-methoxy-2-naphthyl, naphthyl or quinolinyl;

$R^2$ is a $C_{1-6}$ alkyl group;

$R^3$ and $R^4$ are each hydrogen, or $R^3$ is hydrogen and $R^4$ is acetyl or benzoyl, or $R^3$ and $R^4$ together form propan-2-ylidene or $R^3$ and $R^4$, together with a nitrogen atom to which $R^3$ and $R^4$ are bound, form phthalimide or succinimide;

$R^5$ is hydrogen; and

X is O, or a salt or solvate thereof.

2. The compound according to claim 1, wherein $R^1$ is 2-naphthyl, $R^2$ is methyl, $R^3$ and $R^4$ are each hydrogen or $R^3$ and $R^4$, together with a nitrogen atom to which $R^3$ and $R^4$ are bound, form phthalimide, $R^5$ is hydrogen, and X is O.

3. A method for inhibiting biosynthesis of auxin in a plant, comprising applying the compound according to claim 1 to the plant.

4. A method for inhibiting tryptophan aminotransferase in a plant, comprising applying the compound according to claim 1 to the plant.

5. A method for inhibiting tryptophan aminotransferase, comprising bringing the compound according to claim 1 into contact with the tryptophan aminotransferase in vitro.

6. A method for regulating growth of a plant, comprising applying the compound according to claim 1 to the plant.

7. A method for weeding a plant, comprising applying the compound according to claim 1 to the plant.

* * * * *